US012590296B2

(12) United States Patent
Baffet et al.

(10) Patent No.: US 12,590,296 B2
(45) Date of Patent: Mar. 31, 2026

(54) METHOD OF CULTURING IMMORTALIZED HUMAN HEPATIC PROGENITORS OR CELLS

(71) Applicants:INSERM (INSTITUT NATIONAL DE LA SANTÉ ET DE LA RECHERCHE MÉDICALE), Paris (FR); UNIVERSITÉ DE RENNES 1, Rennes (FR); ÉCOLE DES HAUTES ÉTUDES EN SANTÉ PUBLIQUE (EHESP), Rennes (FR)

(72) Inventors: Georges Baffet, Le Rheu (FR); Marie Cuvellier, Rennes (FR); Frédéric Ezan, Rennes (FR); Sophie Rose, Rennes (FR)

(73) Assignees: INSERM (INSTITUT NATIONAL DE LA SANTÉ ET DE LA RECHERCHE MÉDICALE), Paris (FR); UNIVERSITÉ DE RENNES 1, Rennes (FR); ÉCOLE DES HAUTES ÉTUDES EN SANTÉ PUBLIQUE (EHESP), Rennes (FR)

( * ) Notice: Subject to any disclaimer, the term of this patent is extended or adjusted under 35 U.S.C. 154(b) by 799 days.

(21) Appl. No.: 17/776,053

(22) PCT Filed: Nov. 13, 2020

(86) PCT No.: PCT/EP2020/082088
§ 371 (c)(1),
(2) Date: May 11, 2022

(87) PCT Pub. No.: WO2021/094555
PCT Pub. Date: May 20, 2021

(65) Prior Publication Data
US 2022/0396773 A1 Dec. 15, 2022

(30) Foreign Application Priority Data
Nov. 15, 2019 (EP) .................................... 19306473

(51) Int. Cl.
*C12N 5/071* (2010.01)
*G01N 33/50* (2006.01)
(52) U.S. Cl.
CPC ....... *C12N 5/0671* (2013.01); *G01N 33/5067* (2013.01); *C12N 2501/33* (2013.01); *C12N 2501/39* (2013.01); *C12N 2513/00* (2013.01); *C12N 2533/30* (2013.01); *C12N 2533/54* (2013.01)
(58) Field of Classification Search
None
See application file for complete search history.

(56) References Cited

U.S. PATENT DOCUMENTS 7,456,018 B2 11/2008 Gripon et al.

FOREIGN PATENT DOCUMENTS

WO 2013/087843 A1 6/2013
WO 2019/219828 A1 11/2019

OTHER PUBLICATIONS

Bhise, N. S., et al. "A liver-on-a-chip platform with bioprinted hepatic spheroids. Biofabrication 8 (1): 014101." 2016, (Year: 2016).*
Grix, Tobias, et al. "Bioprinting perfusion-enabled liver equivalents for advanced organ-on-a-chip applications." Genes 9.4 (2018): 176. (Year: 2018).*
Millicell® Ultra-low Attachment Plates. Millipore product information sheet. (Year: 2023).*
Ingram, Patrick, et al. "Spheroid cell culture on PDMS hydrophobic surfaces and integration into microfludic devices." Proceedings of the International Conference on Miniaturized Systems for Chemistry and Life Sciences (MicroTAS'11). 2011. (Year: 2011).*
Ma, Xuanyi, et al. "Deterministically patterned biomimetic human iPSC-derived hepatic model via rapid 3D bioprinting." Proceedings of the National Academy of Sciences 113.8 (2016): 2206-2211. (Year: 2016).*
Fu, Gong-Bo, et al. "Expansion and differentiation of human hepatocyte-derived liver progenitor-like cells and their use for the study of hepatotropic pathogens." Cell Research 29.1 (2019): 8-22. (Year: 2019).*
Corning"Spheroid formation protocol". (Year: 2025).*
Lee et al., "Colloidal templating of highly ordered gelatin methacryloyl-based hydrogel platforms for three-dimensional tissue analogues", NPG Asia Materials, 2017, vol. 9, No. e412, 11 pages.
International Search Report issued on Apr. 16, 2021, in connection with corresponding International Patent Application No. PCT/EP2020/082088; 8 pages.

(Continued)

*Primary Examiner* — Tracy Vivlemore
*Assistant Examiner* — Fatimah Khalaf Matalkah
(74) *Attorney, Agent, or Firm* — Maier & Maier, PLLC

(57) ABSTRACT

A method of obtaining 3D cell structures including differentiated human hepatic cells. The method includes: a first step of culturing stem cell-derived or immortalized human hepatic progenitors in a non-adherent culture vessel, preferably a low or ultra-low attachment culture vessel; a second step of transferring the stem cell-derived or immortalized human hepatic progenitors to a culture medium including methacrylated gelatin (GelMa), thereby embedding the stem cell-derived or immortalized human hepatic progenitors in a GelMa matrix; and a third step of covering the GelMa matrix with culture medium and culturing the stem cell-derived or immortalized human hepatic progenitors embedded in the GelMa matrix, thereby obtaining 3D cell structures including differentiated human hepatic cells. Also, methods for engineering an artificial liver model or an artificial liver organ, and for assessing in vitro the metabolism, toxicity and/or therapeutic effects of a compound.

15 Claims, 21 Drawing Sheets
Specification includes a Sequence Listing.

(56)          References Cited

OTHER PUBLICATIONS

Grix et al., "Bioprinting Perfusion-Enabled Liver Equivalents for Advanced Organ-on-a-Chip Applications", Genes (Basel), Mar. 22, 2018; 9(4), 176, p. 1-15.

Bhise et al., "A liver-on-a-chip platform with bioprinted hepatic spheroids. Biofabrication", Jan. 12, 2016, 8(1), 014101 p. 1-13.

Cui et al., "Multicellular Co-Culture in Three-Dimensional Gelatin Methacryloyl Hydrogels for Liver Tissue Engineering Molecules", May 7, 2019; 24(9), 1762, p. 1-10.

Guillouzo et al., "The human hepatoma HepaRG cells: a highly differentiated model for studies of liver metabolism and toxicity of xenobiotics", Chem Biol Interact, May 20, 2007, 168(1), p. 66-73.

Ramaiahgari et al., "Organotypic 3D HepaRG Liver Model for Assessment of Drug-Induced Cholestasis", Methods Mol Biol., 2019, 1981, p. 313-323.

Takahashi et al., "Formation of hepatocyte spheroids with structural polarity and functional bile canaliculi using nanopillar sheets", Tissue Eng Part A. Jun. 2010, 16(6), p. 1983-1995.

Kyffin et al., "Characterisation of a functional rat hepatocyte spheroid model. Toxicol In Vitro", Mar. 2019, 55, p. 160-172.

Wang et al., "Generation of hepatic spheroids using human hepatocyte-derived liver progenitor-like cells for hepatotoxicity screening", Theranostics, Sep. 18, 2019, 9(22), p. 6690-6705.

Bell et al., "Characterization of primary human hepatocyte spheroids as a model system for drug-induced liver injury, liver function and disease". Sci Rep. May 4, 2016, 6, 25187, p. 1-13.

Guo et al., "Similarities and differences in the expression of drug-metabolizing enzymes between human hepatic cell lines and primary human hepatocytes", Drug Metab Dispos., Mar. 2011, 39(3), p. 528-538.

Yokoyama et al., "Comparison of Drug Metabolism and Its Related Hepatotoxic Effects in HepaRG, Cryopreserved Human Hepatocytes, and HepG2 Cell Cultures", Biol Pharm Bull., May 1, 2018, 41(5), p. 722-732.

Josse et al., "Long-term functional stability of human HepaRG hepatocytes and use for chronic toxicity and genotoxicity studies", Drug Metab Dispos., Jun. 2008, 36(6), p. 1111-1118.

Nishimura et al., "Effects of dimethyl sulfoxide on the gene induction of cytochrome P450 isoforms, UGT-dependent glucuronosyl transferase isoforms, and ABCB1 in primary culture of human hepatocytes", Biol Pharm Bull., Jul. 2003, 26(7), p. 1052-1056.

Zanger et al., "Cytochrome P450 enzymes in drug metabolism: regulation of gene expression, enzyme activities, and impact of genetic variation", Pharmacol Ther., Apr. 2013, 138(1), p. 103-141.

Murphy et al., "3D bioprinting of tissues and organs, Nat Biotechnol". Aug. 2014, 32(8), p. 773-785.

Yue et al., "Synthesis, properties, and biomedical applications of gelatin methacryloyl (GelMA) hydrogels", Biomaterials, Dec. 2015, 73, p. 254-271.

Aninat et al., "Expression of cytochromes P450, conjugating enzymes and nuclear receptors in human hepatoma HepaRG cells", Drug Metab Dispos, Jan. 2006, 34(1), p. 75-83.

Kim et al., "A liver-specific gene expression panel predicts the differentiation status of in vitro hepatocyte models Hepatology", Nov. 2017, 66(5), p. 1662-1674.

Xu et al., "Human hepatic stellate cell lines, LX-1 and LX-2: new tools for analysis of hepatic fibrosis". Gut, Jan. 2005, 54(1), p. 142-151.

Czaja et al., "In vitro and in vivo association of transforming growth factor-beta 1 with hepatic fibrosis", J Cell Biol., Jun. 1989, 108(6), p. 2477-2482.

Malinen et al., "Differentiation of liver progenitor cell line to functional organotypic cultures in 3D nanofibrillar cellulose and hyaluronan-gelatin hydrogels", Biomaterials, Jun. 2014, 35(19), p. 5110-5112.

Ramaiahgari et al., "Three-Dimensional (3D) HepaRG Spheroid Model With Physiologically Relevant Xenobiotic Metabolism Competence and Hepatocyte Functionality for Liver Toxicity Screening", Toxicol Sci., Nov. 1, 2017, 160(1), p. 189-190.

Rebelo et al., "HepaRG microencapsulated spheroids in DMSO-free culture: novel culturing approaches for enhanced xenobiotic and biosynthetic metabolism", Arch Toxicol, Aug. 2015, 89(8), p. 1347-1358.

Nishikawa et al., "Hepatocytic cells form bile duct-like structures within a three-dimensional collagen gel matrix", Exp Cell Res., Mar. 15, 1996, 223(2), p. 357-371.

Bomo et al., "Increasing 3D Matrix Rigidity Strengthens Proliferation and Spheroid Development of Human Liver Cells in a Constant Growth Factor Environment", J Cell Biochem., Mar. 2016, 117(3), p. 708-720.

Tostoes et al., "Human liver cell spheroids in extended perfusion bioreactor culture for repeated-dose drug testing", Hepatology, Apr. 2012, 55(4), p. 1227-1236.

Popnikolov et al., "In vivo growth stimulation of collagen gel embedded normal human and mouse primary mammary epithelial cells. J Cell Physiol", Apr. 1995, 163(1), p. 51-60.

Chen et al., "A 3D microfluidic platform incorporating methacrylated gelatin hydrogels to study physiological cardiovascular cell-cell interactions", Lab Chip. Jul. 7, 2013, 13(13), p. 2591-2598.

Cui et al., "Advances in multicellular spheroids formation", J R Soc Interface. Feb. 2017, 14(127), p. 1-16.

Lauschke et al., "Novel 3D Culture Systems for Studies of Human Liver Function and Assessments of the Hepatotoxicity of Drugs and Drug Candidates", Chem Res Toxicol, Dec. 19, 2016, 29(12), p. 1936-1955.

* cited by examiner

FIG. 1A
| GelMa (%) | Polymerization | Printability |
|---|---|---|
| 2.5 | - | - |
| 5 | + | + |
| 10 | + | + |
FIG. 1B
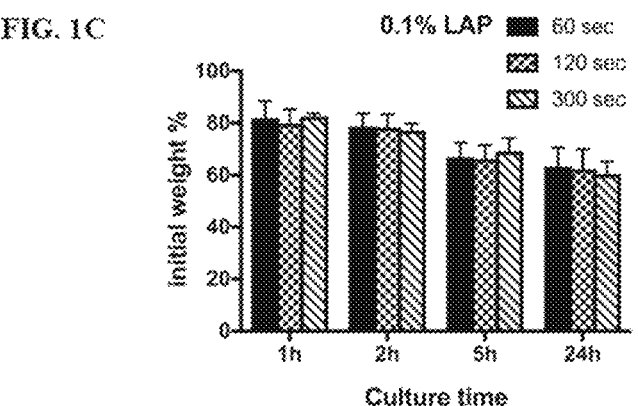
FIG. 1C
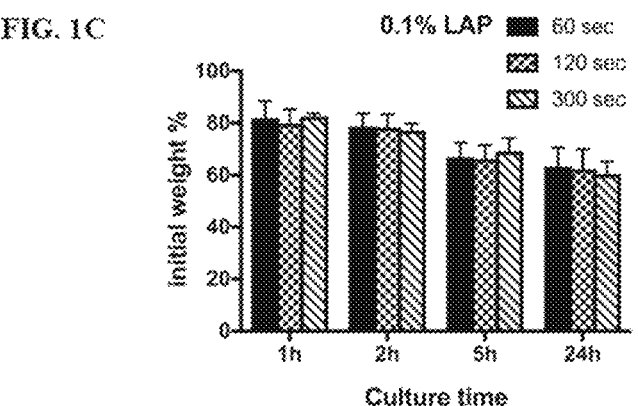
FIG. 1D
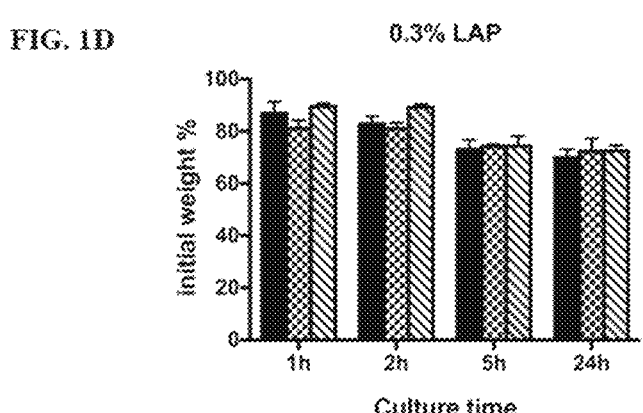

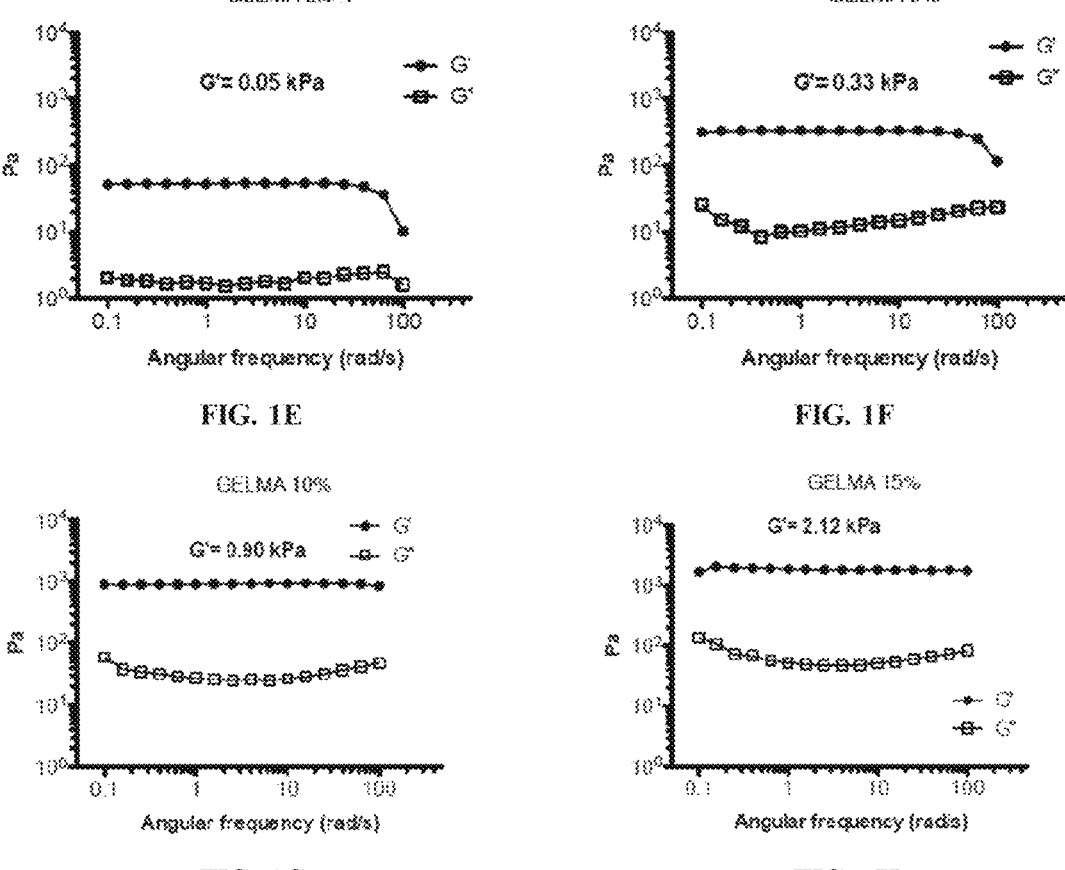
FIG. 1E                      FIG. 1F
FIG. 1G                      FIG. 1H FIG. 2A
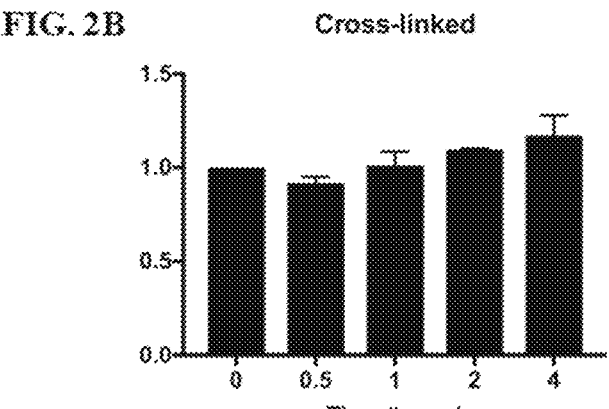
FIG. 2B
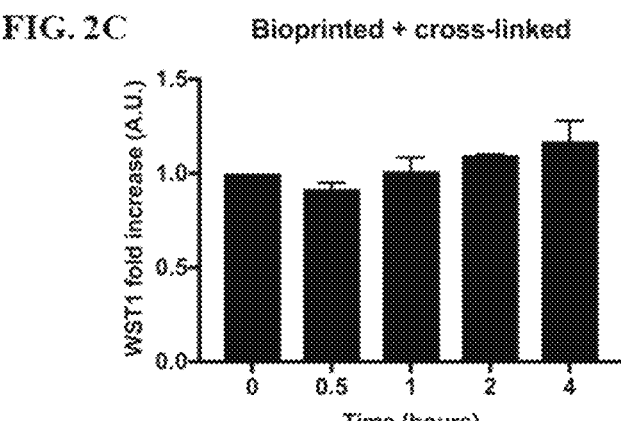
FIG. 2C

| FIG. 2F | Day 5 | Day 10 | Day 14 |
|---|---|---|---|
| Ki67 | 12.51 ± 3.60 | 27.19 ± 12.01 | 20.35 ± 2.77 |
| CCasp3 | 5.87 ± 2.86 | 5.03 ± 1.39 | 7.03 ± 4.22 |

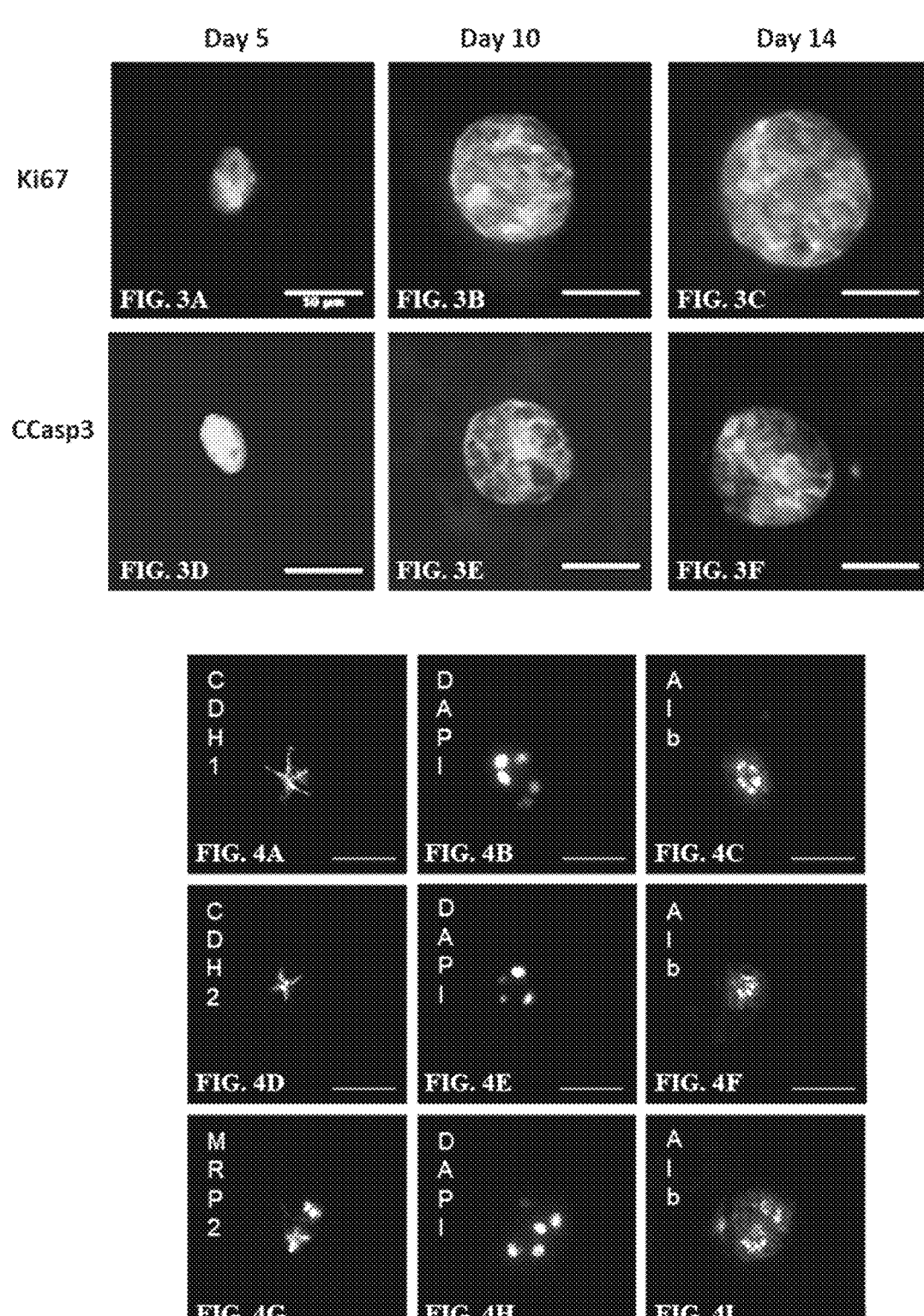

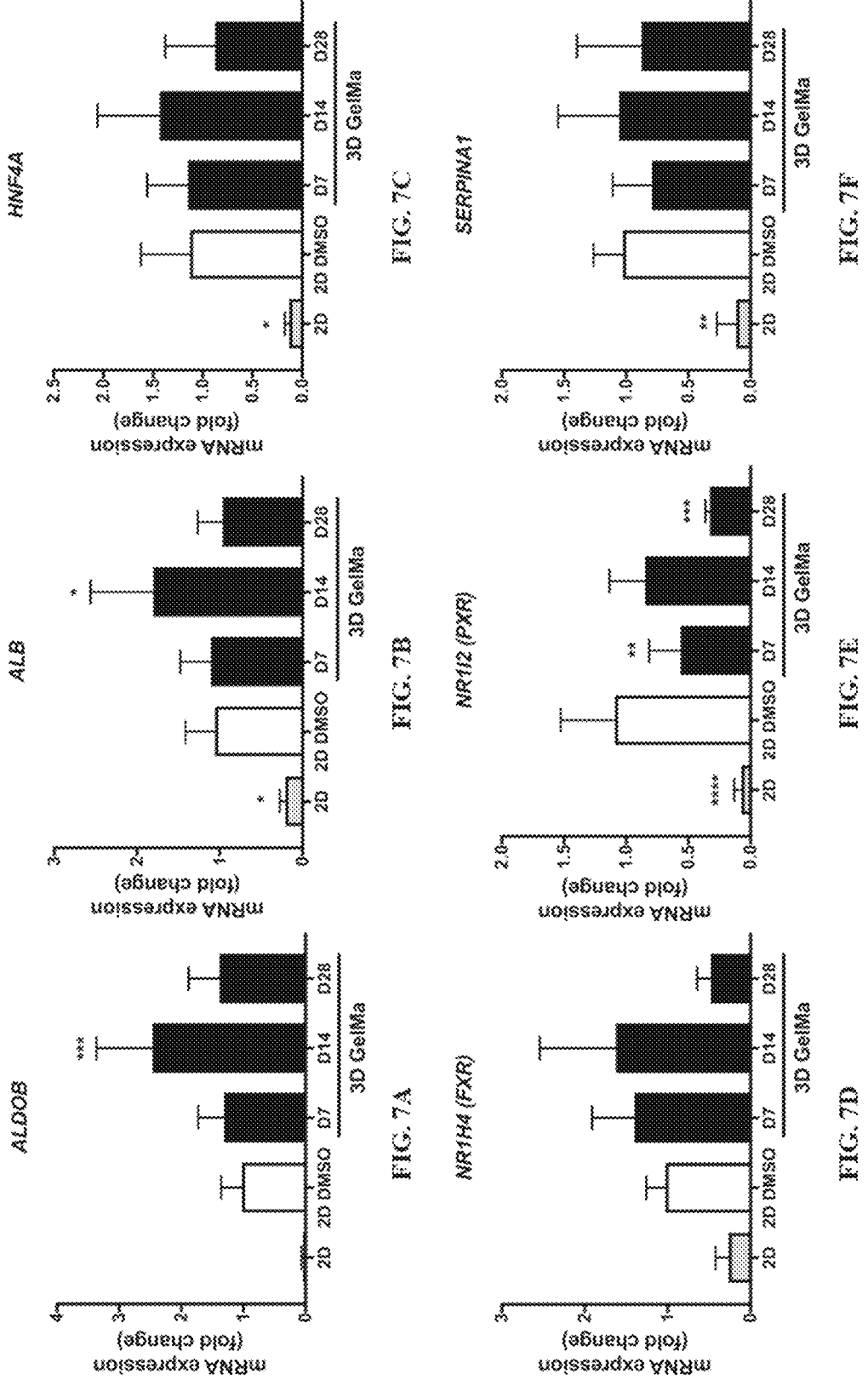

FIG. 8A   Urea secretion
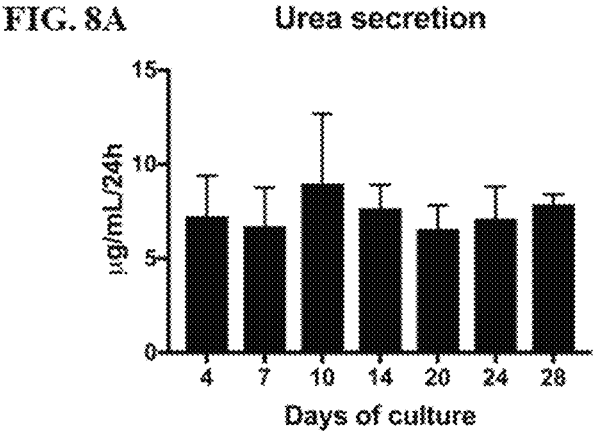
FIG. 8B   Albumin secretion
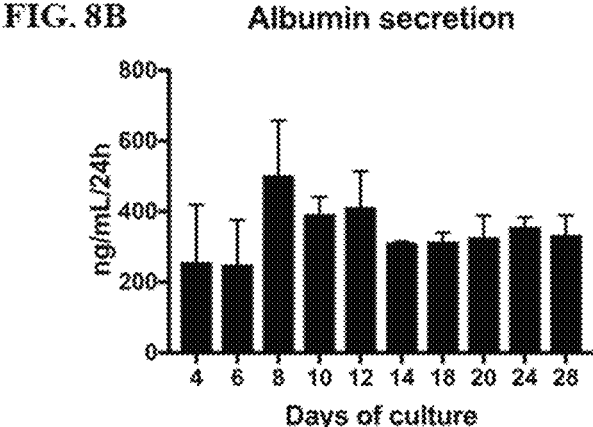
FIG. 8C
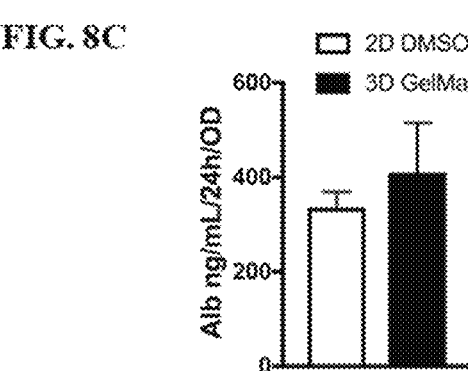

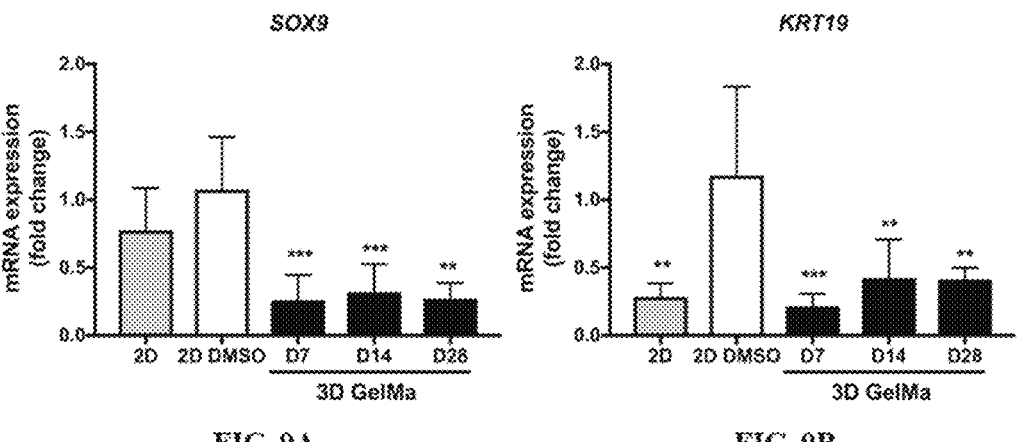
FIG. 9A                                FIG. 9B
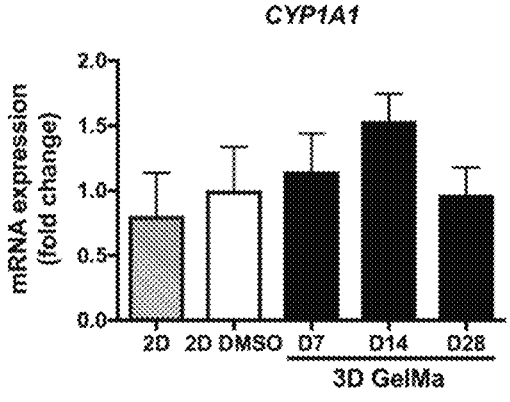
FIG. 10A
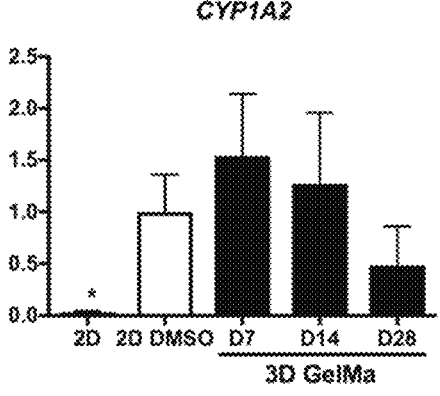
FIG. 10B
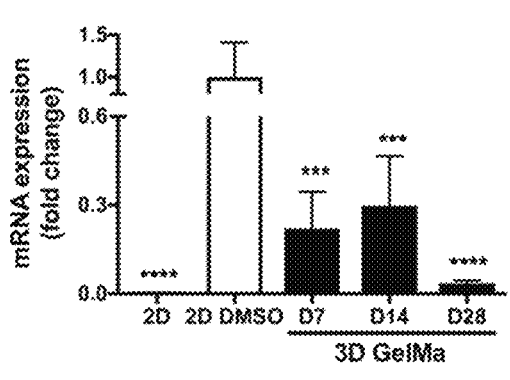
FIG. 10C
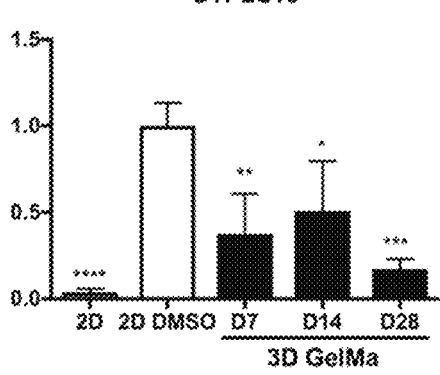
FIG. 10D

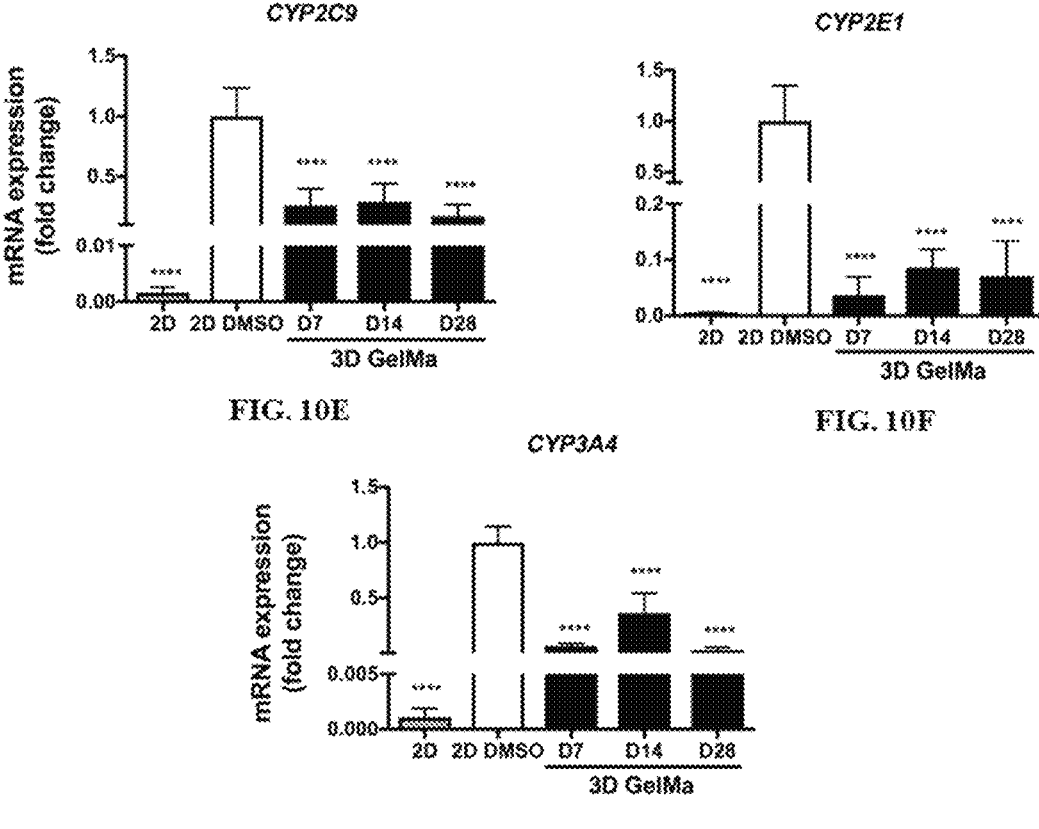
FIG. 10E
FIG. 10F
FIG. 10G
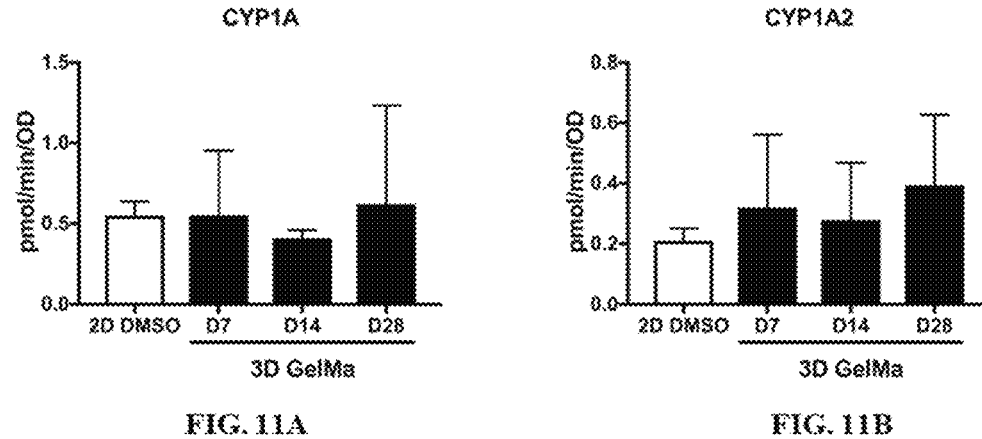
FIG. 11A
FIG. 11B

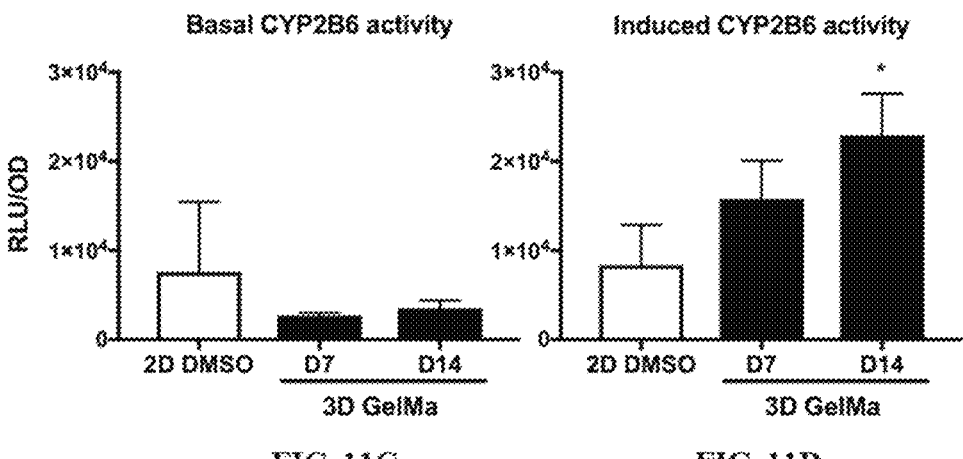
FIG. 11C
FIG. 11D
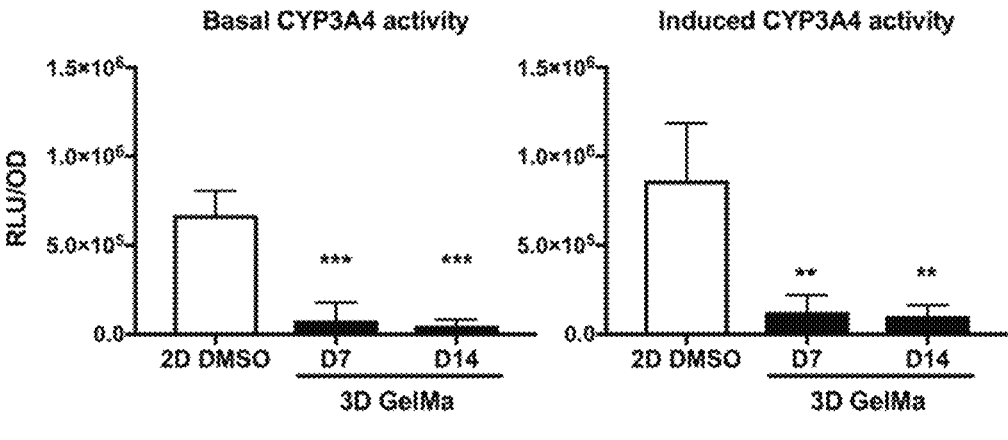
FIG. 11E
FIG. 11F
| FIG. 11G | 2D DMSO | 3D GelMa D7 | 3D GelMa D14 |
|---|---|---|---|
| CYP1A2 | 5.04 ± 2.37 | 14.91 ± 5.72 | 15.99 ± 5.95 |
| CYP2B6 | 1.55 ± 0.85 | 5.85 ± 0.99 ** | 6.64 ± 1.01 ** |
| CYP3A4 | 1.26 ± 0.29 | 1.69 ± 0.55 | 2.22 ± 0.34 * |

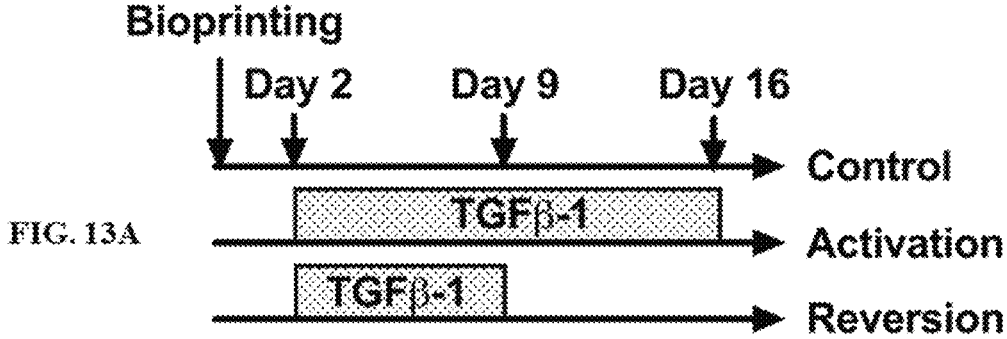
FIG. 13A
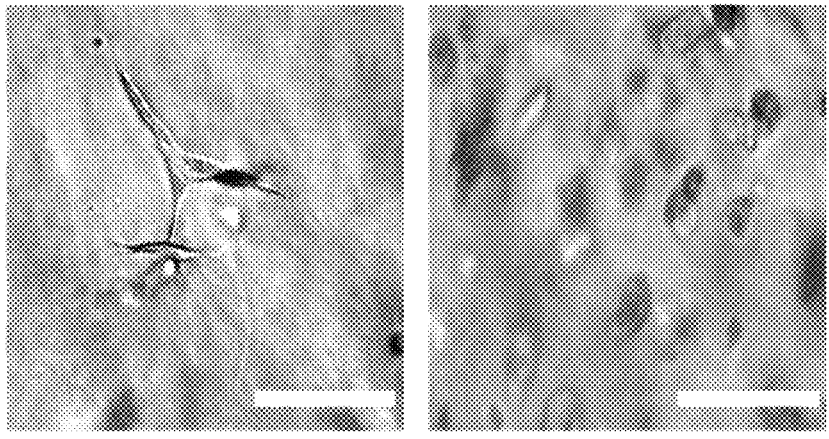
FIG. 13B            FIG. 13C
FIG. 13D
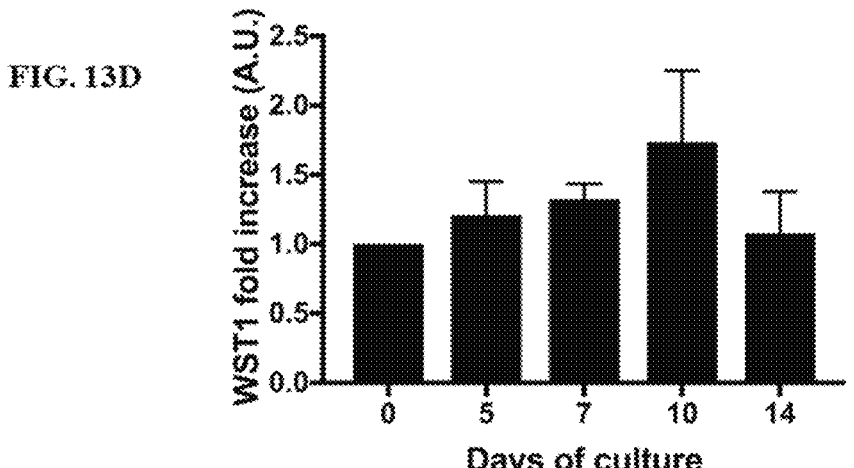

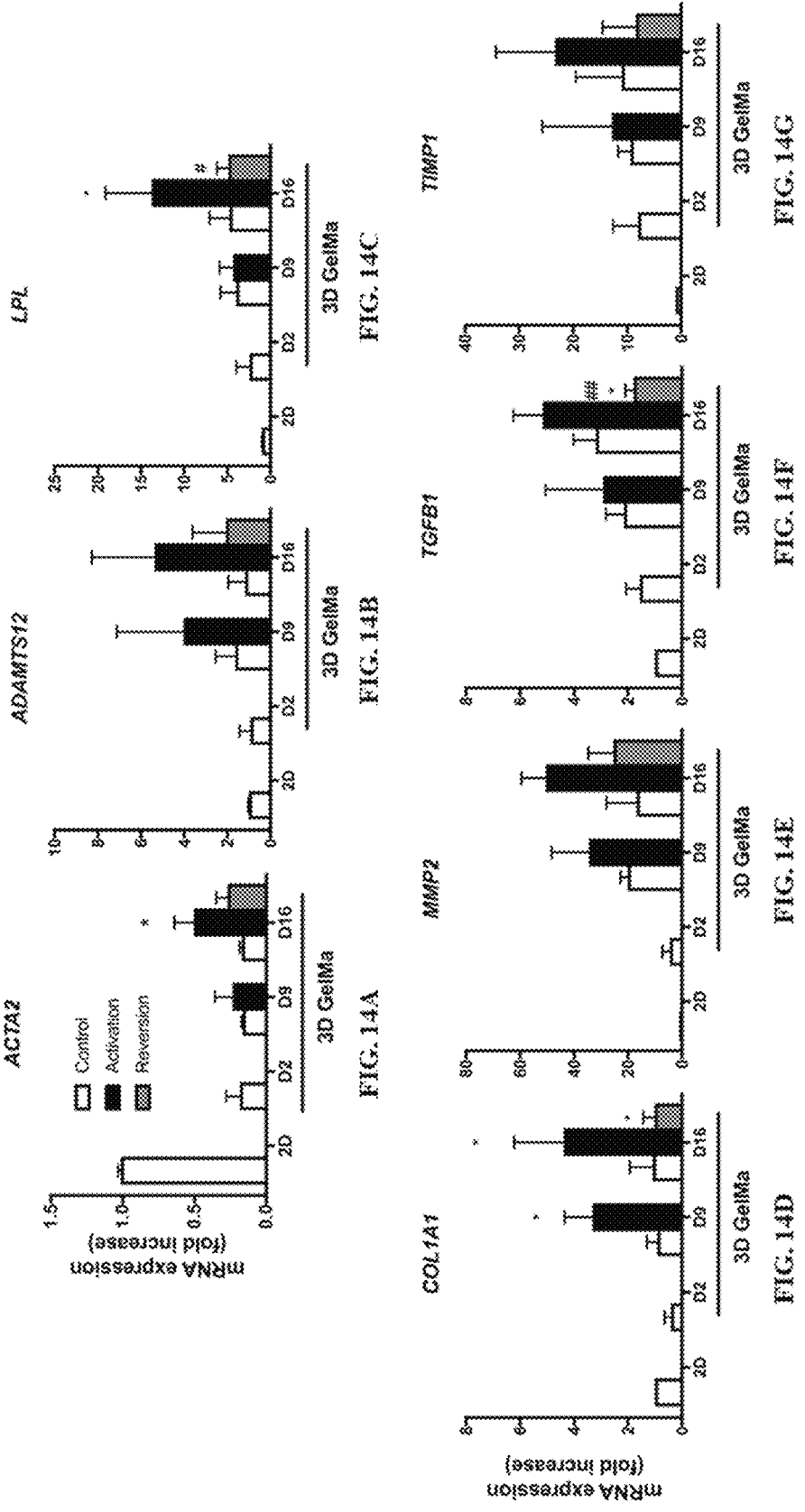

FIG. 15A
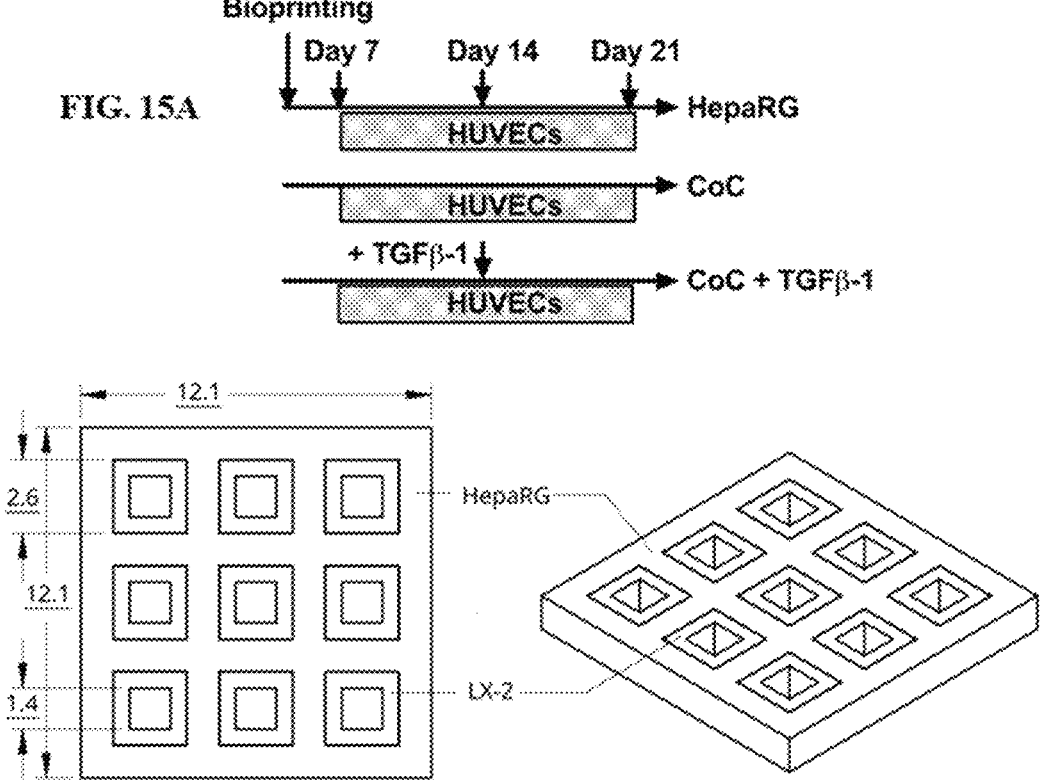
FIG. 15B
FIG. 15C
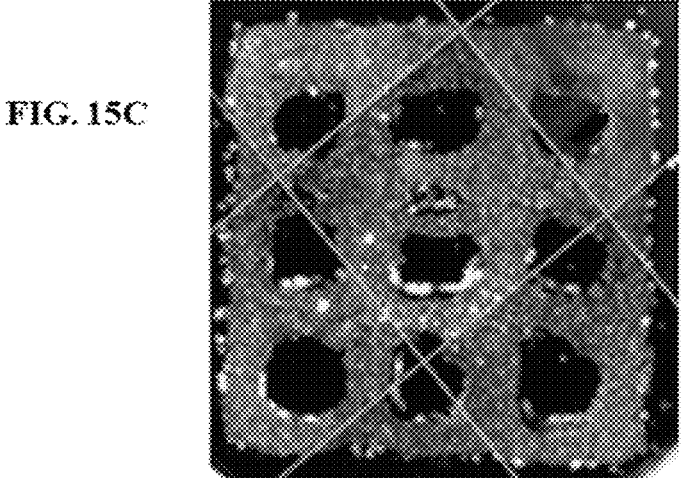

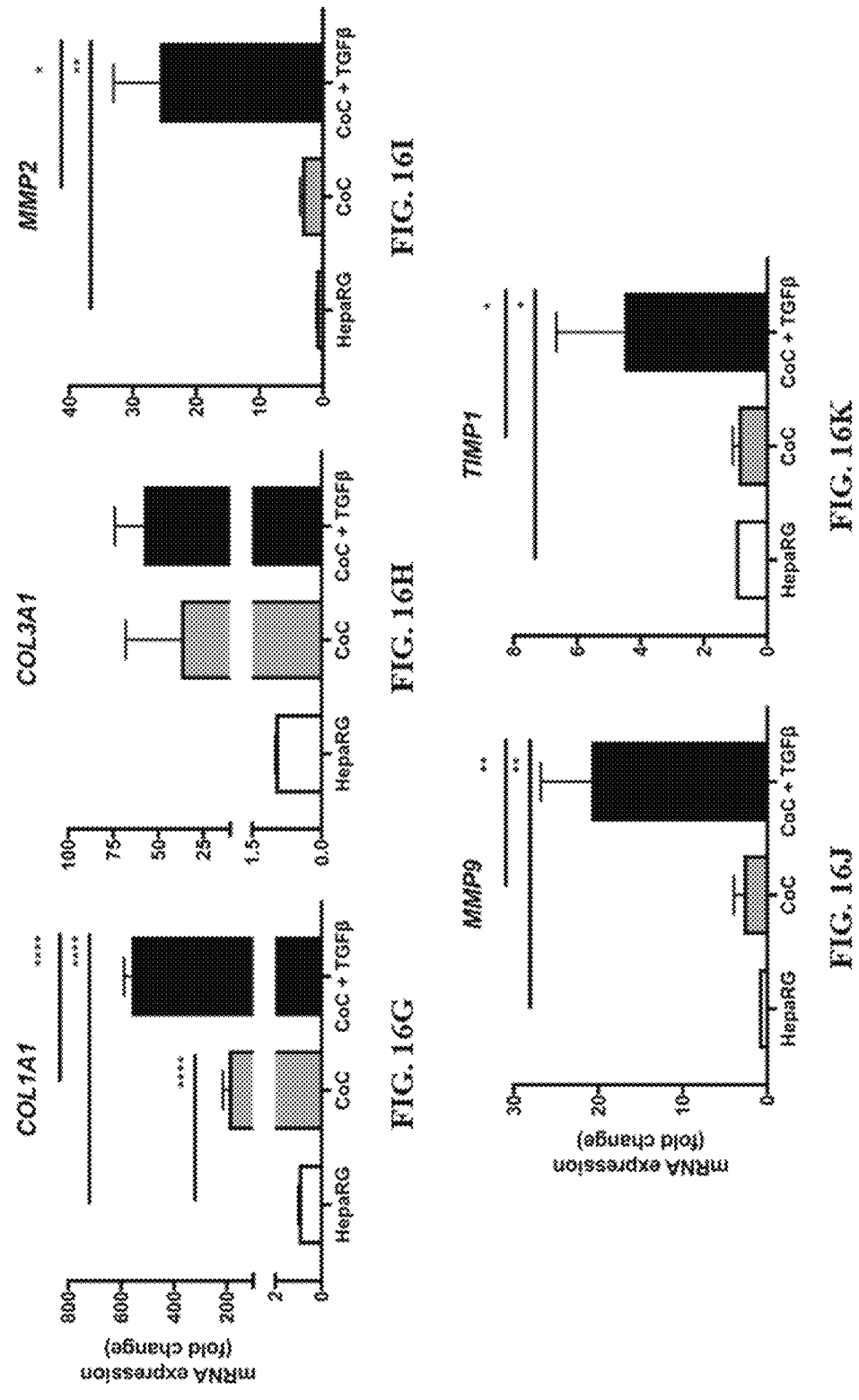

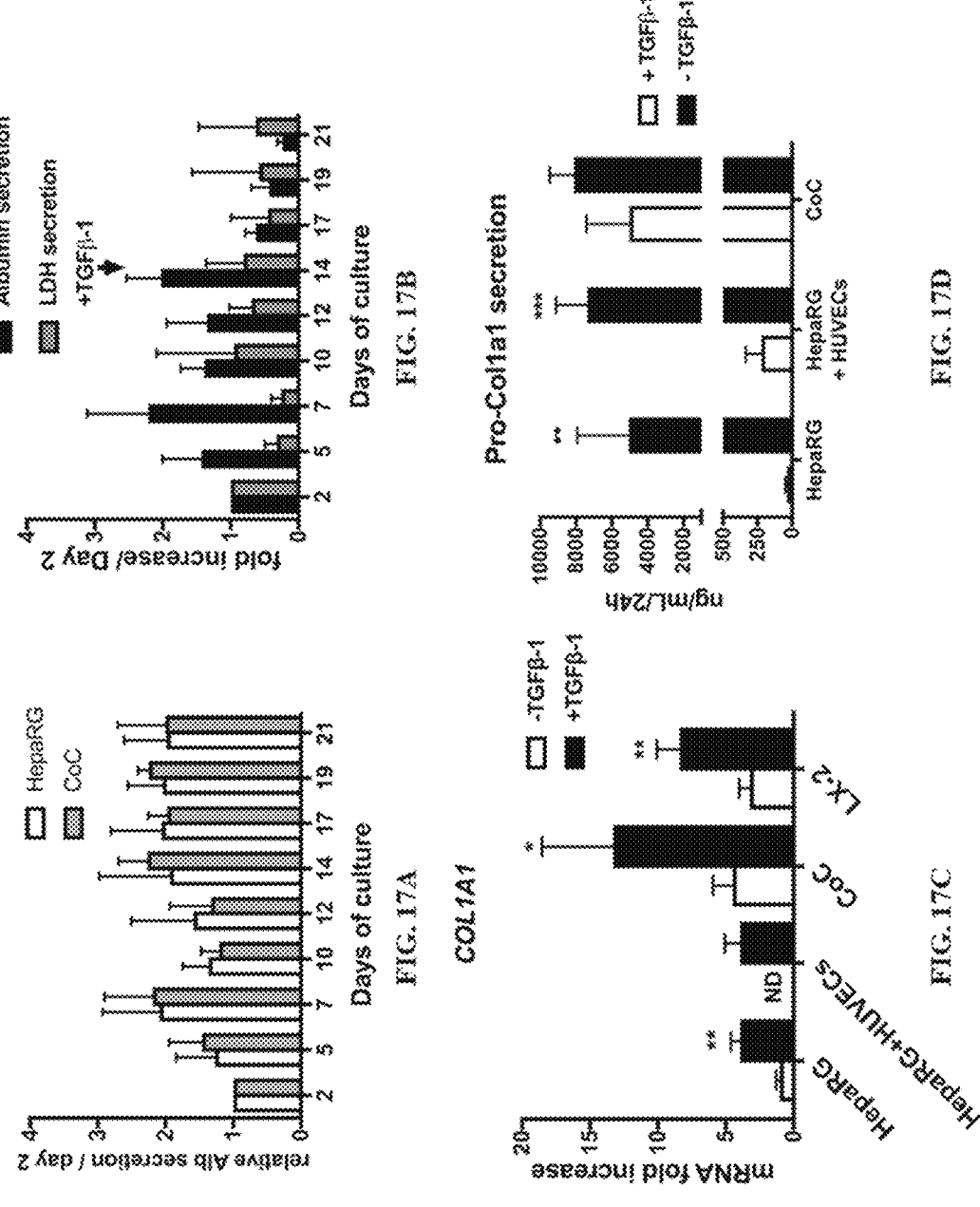

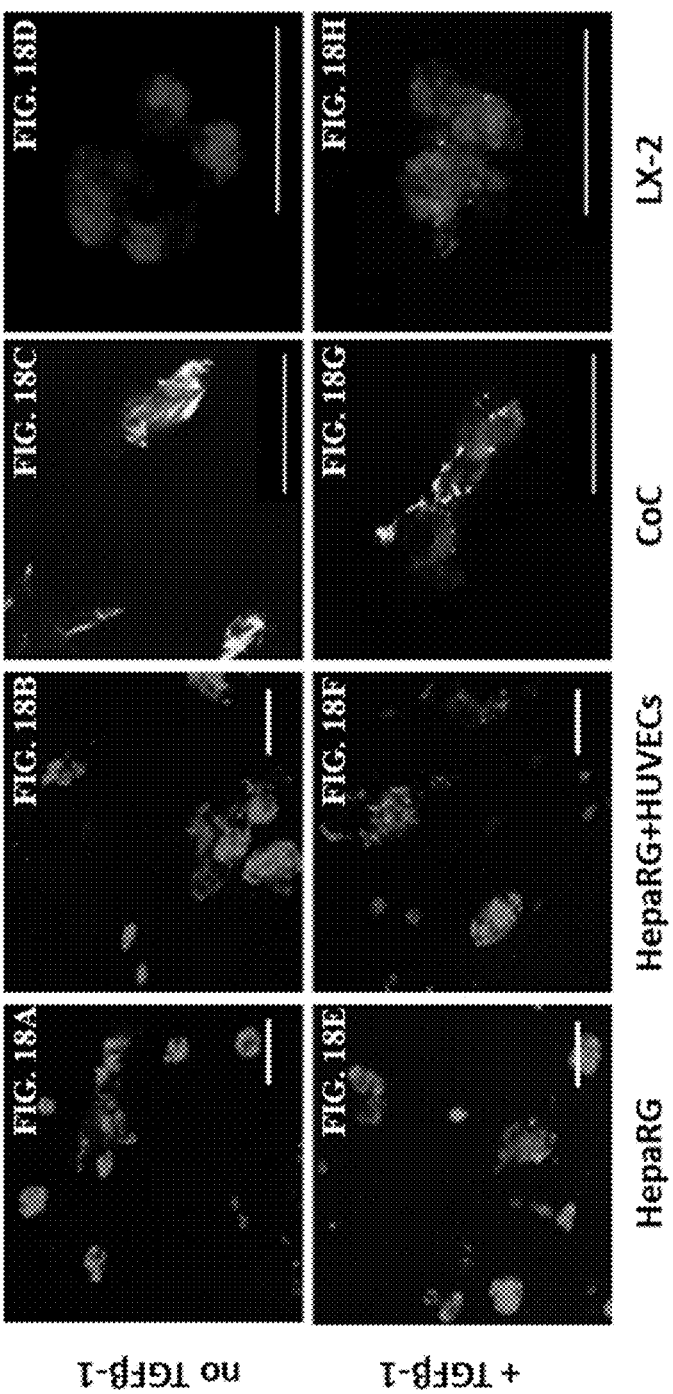

METHOD OF CULTURING IMMORTALIZED HUMAN HEPATIC PROGENITORS OR CELLS

FIELD

The present invention relates to the field of cell culture, and in particular 3D cell culture, notably 3D cell culture of immortalized human hepatic progenitors or cells.

BACKGROUND

Hepatocytes are the major parenchymal cells of the liver and represent up to 70-85% of the liver mass. Hepatocytes are highly differentiated cells that carry out most of the hepatic functions, which pertain notably to bile secretion, glycogen synthesis, metabolism, detoxification and systemic homeostasis. Hepatocytes are polarized cells which have basal/sinusoidal domains facing liver sinusoidal endothelial cells; lateral domains; and one or more apical/canalicular domains that can contribute to several bile canaliculi jointly with the directly opposing hepatocytes. In the liver, hepatocytes normally are long-lived quiescent cells. However, upon injury or loss of functional mass, hepatocytes are able to proliferate, thus allowing liver regeneration.

The establishment of in vitro cultures of hepatocytes has long been pursued with the aim of developing in vitro models able to faithfully recapitulate key liver functions. Such models can be used in research to understand and study normal liver functions. They can also be used to understand and study liver lesions (for example liver fibrosis) and liver pathologies (for example viral hepatitis), and assess the ability of candidate drugs to restore liver functions. Moreover, given the central role of the liver in metabolism and detoxification, in vitro cultures of hepatocytes are relevant models to predict the metabolism and toxicity of new drugs.

Methods of obtaining three-dimensional (3D) structures comprising differentiated hepatic cells are thought to be particularly relevant in order to faithfully recapitulate key liver functions and develop in vitro models. Notably, three-dimensional (3D) cultures have been showed to be particularly suited for obtaining primary hepatocytes with a stable phenotype, able to retain morphology, viability and hepatocyte-specific functions. For example, primary human hepatocyte free sphere-shaped aggregates can be obtained, such as when hepatocytes are cultured in ultra-low attachment plates (Bell et al., Sci Rep. 2016 May 4; 6:25187) or when hepatocytes are encapsulated or embedded in a matrix or a scaffold, such as a polysaccharide scaffold, for example alginate (WO2013/087843). Moreover, it is possible to obtain organized 3D structures, and in particular organized 3D structures comprising different types of hepatic cells in coculture, for example through the use of bioprinting processes.

However, considering the current difficulty of maintaining primary human hepatocytes in culture, many studies on the toxicity and metabolism of drugs and xenobiotics are conducted using immortalized or stem cell-derived human hepatocytes or hepatocyte-like cells. A number of immortalized human hepatic cell lines are thus available, either originating from tumors or obtained by oncogenic immortalization (i.e., by cell transformation). Such lines of immortalized human hepatic progenitors or cells are able to give rise to immortalized hepatocytes or hepatocyte-like cells. For example, HuH-7 and HepG2 are human hepatic cell lines derived from human hepatocellular carcinoma. Fa2N-4 is a Simian virus 40 immortalized human hepatocyte-like cell line.

HepaRG is a line of human hepatic progenitors (i.e., undifferentiated human hepatic cells) derived from human hepatocellular carcinoma. Human hepatocytes or hepatocyte-like cells may also be derived from stem cells and notably from human pluripotent stem cells such as human induced pluripotent stem cells (iPSCs). For example, Hepatosight-S® cells are commercially available hepatic cells derived from iPSCs.

Strikingly, different immortalized human hepatic progenitors or cells present varying level of differentiation, and thus present varying degrees of similarity with primary hepatocytes which, as indicated above, are highly differentiated cells (Guo et al., Drug Metab Dispos. 2011 March; 39(3): 528-38). Notably, the HepaRG cell line is able to give rise to hepatocyte-like cells displaying a high level of differentiation, significantly higher than that of other immortalized human hepatic cell lines, indicating that the HepaRG cells can be useful human hepatic cellular models notably for toxicity studies (Yokoyama et al., Biol Pharm Bull. 2018 May 1; 41(5):722-732). The hepatocyte-like cells obtained from HepaRG progenitors possess many characteristics of primary human hepatocytes and thus represent a particularly relevant model for in vitro studies. Of note, with the commonly used culturing method, HepaRG progenitors give rise to a proportion of about 50% of hepatocyte-like cells and about 50% of primitive biliary cells However, the high level of differentiation of HepaRG cells is dependent on a time-consuming culturing process, which only enables the cells to acquire differentiated functions after 28 days of culture, including 14 days of culture in presence of a high concentration of dimethyl sulfoxide (DMSO) (2%) (Jossé et al., Drug Metab Dispos. 2008 June; 36(6):1111-8). DMSO is known to strongly induce the expression of P450 cytochromes, such as CYP3A4 (cytochrome P450 family 3 subfamily A member 4), the most abundant hepatic cytochrome (Nishimura et al., Biol Pharm Bull. 2003 July; 26(7):1052-6). Preferably, DMSO induction should be avoided when studying the metabolism of drugs and xenobiotics depending on CYP3A4. It is estimated that the CYP3A cytochrome subfamily, in particular CYP3A4, plays a major role in the metabolism of 30% of clinically used drugs from almost all therapeutic categories (Zanger & Schwab, Pharmacol Ther. 2013 April; 138(1):103-41).

Moreover, during the culturing process of HepaRG progenitors, the proliferation stage and the differentiation stage are distinct and do not overlap. In other words, the HepaRG progenitors either proliferate or differentiate, but do not give rise to proliferating differentiated hepatocyte-like cells. The lack of proliferation precludes any study on the genotoxicity of a drug or xenobiotic.

Therefore, there is still a need for a method of obtaining 3D cell structures comprising human hepatic cells, preferably differentiated human hepatic cells such as hepatocytes or hepatocyte-like cells, from stem-cell derived or immortalized human hepatic progenitors or cells, such as HepaRG progenitors. In particular, there is still a need for a method of obtaining 3D cell structures comprising human hepatic cells, preferably differentiated human hepatic cells such as hepatocytes or hepatocyte-like cells, suitable for any metabolism, toxicity and genotoxicity studies and well adapted to bioprinting processes.

The present invention thus relates to a method of culturing stem-cell derived or immortalized human hepatic progenitors or cells to obtain 3D cell structures comprising human hepatic cells, said human hepatic cells retaining the ability to proliferate. The method of the invention comprises a first step of culturing the stem-cell derived or immortalized human hepatic progenitors or cells in a non-adherent culture vessel, preferably a low or ultra-low attachment culture vessel; a second step of transferring the stem-cell derived or immortalized human hepatic progenitors or cells to a culture medium comprising methacrylated gelatin (GelMa), thereby embedding the stem-cell derived or immortalized human hepatic progenitors or cells in a GelMa matrix; and a third step of covering the GelMa matrix with culture medium and culturing the stem-cell derived or immortalized human hepatic progenitors or cells embedded in the GelMa matrix.

SUMMARY

The present invention relates to a method of obtaining 3D cell structures comprising differentiated human hepatic cells, said method comprising:

a) culturing stem cell-derived or immortalized human hepatic progenitors in a non-adherent culture vessel, preferably a low or ultra-low attachment culture vessel;

b) transferring the stem cell-derived or immortalized human hepatic progenitors to a culture medium comprising methacrylated gelatin (GelMa), thereby embedding the stem cell-derived or immortalized human hepatic progenitors in a GelMa matrix; and c) covering the GelMa matrix with culture medium and culturing the stem cell-derived or immortalized human hepatic progenitors embedded in the GelMa matrix;

thereby obtaining 3D cell structures comprising differentiated human hepatic cells.

In one embodiment, at step a) of the method of the invention, the stem cell-derived or immortalized human hepatic progenitors are cultured in a non-adherent culture vessel, preferably a low or ultra-low attachment culture vessel, for a duration ranging from about 1 h to about 96 h, preferably from about 5 h to about 72 h. In one embodiment, at step b) of the method of the invention, the stem cell-derived or immortalized human hepatic progenitors are transferred to a culture medium comprising methacrylated gelatin (GelMa) at a final concentration ranging from about 1% (w/v) to about 20% (w/v). In one embodiment, at step c) of the method of the invention, the stem cell-derived or immortalized human hepatic progenitors embedded in the GelMa matrix are cultured for at least seven days. In one embodiment, the culture medium comprises insulin and a glucocorticoid.

In one embodiment, the method of the invention further comprises of step d) of incubating the 3D cell structures comprising differentiated human hepatic cells embedded in the GelMa matrix with a collagenase or an enzyme mixture with collagenolytic activity, thereby isolating the 3D cell structures comprising differentiated human hepatic cells from the GelMa matrix.

In one embodiment, the differentiated human hepatic cells comprised in the 3D cell structure are human hepatocytes or hepatocyte-like cells. In one embodiment, the stem cell-derived or immortalized human hepatic progenitors are hepatocellular carcinoma-derived and/or transformed human hepatic progenitors or cells, preferably undifferentiated HepaRG cells.

The present invention also relates to a spheroid comprising human hepatocytes or hepatocyte-like cells, preferably susceptible to be obtained with the method as described above, wherein said spheroid is a polarized structure with multiple bile canaliculi and comprises a number of human hepatocytes or hepatocyte-like cells ranging from 10 to 100 and/or has a size ranging from 20 to 120 μm. In one embodiment, the spheroid comprising human hepatic cells, preferably human hepatocytes or hepatocyte-like cells, is embedded in a GelMa matrix.

The present invention also relates to the use of the spheroid as described above for engineering an artificial liver model or an artificial liver organ.

The present invention also relates to a method for engineering an artificial liver model or an artificial liver organ comprising differentiated human hepatic cells, the method comprising culturing stem cell-derived or immortalized human hepatic progenitors according to the method as described above with at least another type of cells, wherein the stem cell-derived or immortalized human hepatic progenitors embedded in the GelMa matrix are contacted with the at least another type of cells, the at least another type of cells being optionally embedded in a matrix. In one embodiment, said at least another type of cells is another type of hepatic cells. In one embodiment, the stem cell-derived or immortalized human hepatic progenitors or cells are cultured with stellate cells and/or endothelial cells.

The present invention also relates to the use of the spheroid as described above for assessing in vitro the metabolism, toxicity and/or therapeutic effects of a compound.

The present invention also relates to an in vitro method for assessing the metabolism, toxicity and/or therapeutic effects of a compound, the method comprising:

a) obtaining 3D cell structures comprising differentiated human hepatic cells, preferably human hepatocytes or hepatocyte-like cells, according to the method as described above;

b) contacting the 3D cell structures comprising differentiated human hepatic cells, preferably human hepatocytes or hepatocyte-like cells, with a compound; and c) assessing the metabolism, toxicity and/or therapeutic effects of the compound on the 3D cell structures comprising differentiated human hepatic cells, preferably human hepatocytes or hepatocyte-like cells.

BRIEF DESCRIPTION OF THE DRAWINGS

FIGS. 1A-1H illustrate the physical properties of GelMa matrices. 1A is a table showing the polymerization and printability properties of a GelMa matrix as a function of the GelMa concentration. 1B is a table showing the printability properties of a GelMa matrix as a function of the photoinitiator LAP concentration and the illumination time (also referred to as lighting time) at 405 nm. 1C is a histogram showing the weight loss of a GelMa matrix obtained with 0.1% (w/v) LAP over 48 hours of culture at 37° C. from t0 (immediately after bioprinting and cross-linking). 1D is a histogram showing the weight loss of a GelMa matrix obtained with 0.3% (w/v) LAP over 48 hours of culture at 37° C. from t0 (immediately after bioprinting and cross-linking). In 1C and 1D, black bars correspond to a GelMa matrix crosslinked with an illumination time of 1 min (60 sec), squared bars correspond to a GelMa matrix crosslinked with an illumination time of 2 min (120 sec) and hatched bars correspond to a GelMa matrix crosslinked with an illumination time of 5 min (300 sec). 1E is a graph showing the elastic modulus (G') and viscous modulus (G") of a GelMa matrix comprising 2.5% (w/v) GelMa. 1F is a graph showing the elastic modulus (G') and viscous modulus (G") of a GelMa matrix comprising 5% (w/v) GelMa. 1G is a graph showing the elastic modulus (G') and viscous modulus (G") of a GelMa matrix comprising 10% (w/v) GelMa. 1H is a graph showing the elastic modulus (G') and viscous modulus (G") of a GelMa matrix comprising 15% (w/v) GelMa.

FIGS. 2A-2F illustrate the short- and long-term viability (assessed through WST-1 proliferation assays) of HuH-7 cells in 3D GelMa culture according to the method of the invention. 2A is a histogram showing the short-term viability of HuH-7 cells over 4 hours of culture in a non-bioprinted, non-crosslinked GelMa matrix (i.e., control conditions). 2B is a histogram showing the short-term viability of HuH-7 cells over 4 hours of culture in a crosslinked GelMa matrix. 2C is a histogram showing the short-term viability of HuH-7 cells over 4 hours of culture in a GelMa matrix crosslinked and bioprinted. 2D is a histogram showing the medium-term viability of HuH-7 cells over 14 days of culture in a GelMa matrix comprising the indicated concentration of photoinitiator LAP (0.1% (v/w) or 0.3% (v/w)) and illuminated at 405 nm for the indicated times after seeding (1 min or 2 min). 2E is a histogram showing the long-term viability of HuH-7 cells over 28 days of culture in a GelMa matrix. 2F is a table showing the expression of the proliferation marker Ki67 and of the apoptosis marker cleaved caspase 3 (CCasp3) in HuH-7 cells cultured in a GelMa matrix for 14 days.

FIGS. 3A-3F are photographs illustrating the expression of Ki67 (3A-C) and of the apoptosis marker cleaved caspase 3 (CCasp3) (3D-F) in HuH-7-GFP cells at day 5, 10 and 14 as indicated in a 3D GelMa culture. The expression of Ki67 and CCasp3 was detected by immunostaining. The HuH-7-GFP cells were detected with the GFP signal and their nuclei were detected by staining with DAPI (4',6-diamidino-2-phenylindole). Each white bar represents 50 μm.

FIGS. 4A-4I are photographs illustrating the expression of CDH1 encoded E-cadherin, CDH2 encoded N-cadherin, MRP2 and albumin as indicated in HepaRG cells at day 28 as indicated in a 3D GelMa culture. The expression of CDH1/E-cadherin, CDH2/N-cadherin, MRP2 and albumin was detected by immunostaining. The nuclei of the HepaRG cells were detected by staining with DAPI (4',6-diamidino-2-phenylindole). Each white bar represents 50 μm.

FIGS. 7A-7F illustrate the mRNA expression of genes encoding for proteins responsible for various hepatic functions, in HepaRG cells in negative control 2D culture (without DMSO), in HepaRG cells in positive control 2D-DMSO culture, and in HepaRG cells in 3D GelMa culture according to the method of the invention. The mRNA expressions were assessed at day 14 in undifferentiated HepaRG cells in negative control 2D culture (2D—grey bars), at day 14 in HepaRG cells in positive control 2D-DMSO culture (2D DMSO—white bars), and at day 7 (D7), day 14 (D14) and day 28 (D28) in HepaRG cells in 3D GelMa culture (3D GelMa—black bars). Expression in HepaRG cells in 3D GelMa culture is expressed in relative quantity normalized to expression in HepaRG in 2D-DMSO culture. 7A is a histogram showing the mRNA expression of ALDOB (coding for aldolase). 7B is a histogram showing the mRNA expression of ALB (coding for albumin). 7C is a histogram showing the mRNA expression of HNF4A. 7D is a histogram showing the mRNA expression of NR1H4 (coding for the FXR protein). 7E is a histogram showing the mRNA expression of NR1I2 (coding for the PXR protein). 7F is a histogram showing the mRNA expression of SER-PINA1.

FIGS. 8A-8C illustrate the secretion of urea and albumin by HepaRG cells in 3D GelMa culture according to the method of the invention. 8A is a histogram showing the quantification of urea secreted in the supernatant of 3D GelMa culture of HepaRG cells over 28 days. 8B is a histogram showing the quantification of albumin secreted in the supernatant of 3D GelMa culture of HepaRG cells over 28 days. 8C is a histogram comparing albumin secreted by HepaRG cells at day 14 in 3D GelMa culture (black bar) and in control 2D-DMSO culture (white bar), normalized to viability (assessed by the WST-1 proliferation assay).

FIGS. 9A-9B illustrate the mRNA expression of markers of the biliary lineage, in HepaRG cells in negative control 2D culture (without DMSO), in HepaRG cells in positive control 2D-DMSO culture, and in HepaRG cells in 3D GelMa culture according to the method of the invention. The mRNA expressions were assessed at day 14 in undifferentiated HepaRG cells in negative control 2D culture (2D—grey bars), at day 14 in HepaRG cells in positive control 2D-DMSO culture (2D DMSO—white bars), and at day 7 (D7), day 14 (D14) and day 28 (D28) in HepaRG cells in 3D GelMa culture (3D GelMa—black bars). Expression in HepaRG cells in 3D GelMa culture is expressed in relative quantity normalized to expression in HepaRG in 2D-DMSO culture. 9A is a histogram showing the mRNA expression of SOX9. 9B is a histogram showing the mRNA expression of KRT19 (coding for the CK19 protein).

FIGS. 10A-10G illustrate the mRNA expression of genes encoding phase I enzymes in HepaRG cells in negative control 2D culture (without DMSO), in positive control 2D-DMSO culture, and in HepaRG cells in 3D GelMa culture according to the method of the invention. The mRNA expressions were assessed at day 14 in undifferentiated HepaRG cells in negative control 2D culture (2D—hatched bars), at day 14 in HepaRG cells in positive control 2D-DMSO culture (2D DMSO—white bars) and at day 7 (D7), day 14 (D14) and day 28 (D28) in HepaRG cells in 3D GelMa culture (3D GelMa—black bars). Significant fold changes in 3D GelMa mRNA expression were determined in comparison with 2D (#) or 2D DMSO (*) gene expression. 10A is a histogram showing the mRNA expression of CYP1A1. 10B is a histogram showing the mRNA expression of CYP1A2. 10C is a histogram showing the mRNA expression of CYP2B6. 10D is a histogram showing the mRNA expression of CYP2C19. 10E is a histogram showing the mRNA expression of CYP2C9. 10F is a histogram showing the mRNA expression of CYP2E1. 10G is a histogram showing the mRNA expression of CYP3A4.

FIGS. 11A-11G illustrate the activities of phase I enzymes in HepaRG cells in control 2D-DMSO culture (2D DMSO—white bars) and in HepaRG cells in 3D GelMa culture according to the method of the invention (3D GelMa—black bars). 11A is a histogram showing the induced activity of CYP1A at the indicated times in 3D GelMa culture and at day 14 in 2D DMSO culture. 11B is a histogram showing the induced activity of CYP1A2 at the indicated times in 3D GelMa culture and at day 14 in 2D DMSO culture. 11C is a histogram showing the basal activity of CYP2B6 at the indicated times in 3D GelMa culture and at day 14 in 2D DMSO culture. 11D is a histogram showing the inducted activity of CYP2B6 at the indicated times in 3D GelMa culture and at day 14 in 2D DMSO culture. 11E is a histogram showing the basal activity of CYP3A4 at the indicated times in 3D GelMa culture and at day 14 in 2D DMSO culture. 11F is a histogram showing the inducted activity of CYP3A4 at the indicated times in 3D GelMa culture and at day 14 in 2D DMSO culture. 11G is a table indicating CYP1A2, CYP3A4 and CYP2B6 induced activity in HepaRG cells in 2D-DMSO culture at day 14 and in 3D GelMa culture at day 7 (D7) and at day 14 (D14), normalized to their respective basal activity. Significant inducibility of each CYP were determined in comparison with 2D DMSO (*) CYP inducibility.

FIGS. 13A-13D illustrate the culture of LX-2 cells in 3D GelMa according to the method of the invention. 13A is a scheme illustrating the experimental timeline of the culture of LX-2 cells in 3D GelMa, in the absence of TGFβ-1 (control condition), in the presence of TGFβ-1 from day 2 until day 16 added at 5 ng/mL every 48 h during 14 days (activation), in the presence of TGFβ-1 from day 2 until day 9 added at 5 ng/mL every 48 h during 7 days (reversion). 13B is a photograph obtained with light microscopy of the morphology of LX-2 cells 4 days after seeding in a 1.5 mg/mL collagen 1 matrix. 13C is a photograph obtained with light microscopy of the morphology of LX-2 cells 4 days after seeding in a GelMa matrix according to the method of the invention. 13D is a histogram showing the viability of LX-2 cells in 3D GelMa culture until day 14. Data are represented as fold increase of WST1 activities compared to that of control (day 0).

FIGS. 14A-14G illustrate the mRNA expression of myofibroblastic transition genes and extracellular matrix remodeling genes in LX-2 cells in 3D GelMa culture according to the method of the invention in the absence of TGFβ-1 (control—white bars), in the presence of TGFβ-1 during 14 days (activation—black bars) or during 7 days only following removal of TGFβ-1 at day 9 (reversion—grey bars). The mRNA expressions were assessed at day 14 in LX-2 cells in control 2D culture (2D) and at day 2 (D2), day 9 (D9) and day 16 (D16) in LX-2 cells in 3D GelMa culture (3D GelMa). 3D GelMa mRNA expression was normalized to LX-2 in 2D culture and significant fold changes were determined in comparison to control (*) and 14 days treatment (#) gene expression. 14A is a histogram showing the mRNA expression of ACTA2. 14B is a histogram showing the mRNA expression of ADAMTS12. 14C is a histogram showing the mRNA expression of LPL. 14D is a histogram showing the mRNA expression of COL1A1. 14E is a histogram showing the mRNA expression of MMP2. 14F is a histogram showing the mRNA expression of TGFB1 (encoding for TGFβ-1). 14G is a histogram showing the mRNA expression of TIMP1.

FIGS. 15A-15C illustrate the coculture of HepaRG cells, LX-2 cells and HUVECs (CoC). 15A is a scheme illustrating the experimental timeline of the coculture of LX-2 cells in 3D GelMa. HepaRG cells were bioprinted in 3D GelMa according to the method of the invention without (HepaRG) or with LX-2 cells (CoC) and the 3D structure was seeded with HUVECs at day 7 of culture. The coculture (HepaRG cells+LX-2 cells+HUVECs) was treated with TGFβ-1 at 5 ng/mL every 48 h during 7 days from day 14 until day 21 (CoC+TGFβ-1). 15B is a scheme representing the coculture model in 3D GelMa comprising HepaRG cells and LX-2 cells. 15C is a photograph showing GFP-HUVECs cells 4 days after seeding on the surface of the GelMa matrix.

FIGS. 16A-16K illustrate the mRNA expression of hepatic genes (ALB, ALDOB, PPARA and SERPINA1) and activation genes (ACTA2, ADAMTS12, COL1A1, COL3A1, MMP2, MMP9 and TIMP1) at day 21 in HepaRG without LX-2 cells in 3D GelMa as described above (HepaRG—white bars), in HepaRG in coculture with LX-2 and HUVECs as described above (CoC—grey bars) and in HepaRG in coculture with LX-2 and HUVECs treated with TGFβ-1 as described above (CoC+TGFβ-1—black bars). mRNA expression was normalized to HepaRG without LX-2 cells in 3D GelMa culture. 16A is a histogram showing the mRNA expression of ALB. 16B is a histogram showing the mRNA expression of ALDOB. 16C is a histogram showing the mRNA expression of PPARA (peroxisome proliferator-activated receptor alpha). 16D is a histogram showing the mRNA expression of ACTA2. 16E is a histogram showing the mRNA expression of SERPINA1. 16F is a histogram showing the mRNA expression of ADAMTS12. 16G is a histogram showing the mRNA expression of COL1A1. 16H is a histogram showing the mRNA expression of COL3A1. 16I is a histogram showing the mRNA expression of MMP2. 16J is a histogram showing the mRNA expression of MMP9. 16K is a histogram showing the mRNA expression of TIMP1.

FIGS. 17A-17D illustrate the secretion of albumin, the release of lactate dehydrogenase (LDH), the expression of COL1A1, and the secretion of pro-Col1a1 in coculture. 17A is a histogram showing the relative albumin secretion in HepaRG without LX-2 cells in 3D GelMa as described above (HepaRG—white bars) and in HepaRG in coculture as described above with LX-2 and HUVECs (CoC—grey bars) over time, compared to day 2 albumin secretion. 17B is a histogram showing the relative albumin secretion and the relative LDH release in HepaRG in coculture with LX-2 and HUVECs treated with TGFβ-1 as described above. Data presented here is n=3. 17C is a histogram showing the mRNA expression of the COL1A1 gene in HepaRG cells alone (HepaRG), in HepaRG cells with HUVECs (HepaRG+HUVECs), in HepaRG cells in coculture with LX-2 and HUVECs (CoC), and in LX-2 cells alone (LX-2), without (white bars) or with (black bars) TGFβ-1. mRNA expression was normalized to HepaRG with TGFβ-1. 17D is a histogram showing the quantification in ng/ml of procollagen1a1 secreted in 24 h in the culture medium from HepaRG cells alone (HepaRG), HepaRG cells with HUVECs (HepaRG+HUVECs), and HepaRG cells in coculture with LX-2 and HUVECs (CoC), without (white bars) or with (black bars) TGFβ-1.

FIGS. 18A-18H are photographs illustrating collagen deposition in the GelMa matrix at day 21 analyzed by SHG/TPEF microscopy in HepaRG cells alone (HepaRG— 18A & 18E), in HepaRG cells with HUVECs (HepaRG+ HUVECs—18B & 18F), in HepaRG cells in coculture with LX-2 and HUVECs (CoC—18C & 18G), and in LX-2 cells alone (LX-2—18D & 18H), with or without TGFβ-1 as indicated.

DETAILED DESCRIPTION

Figure 5A:
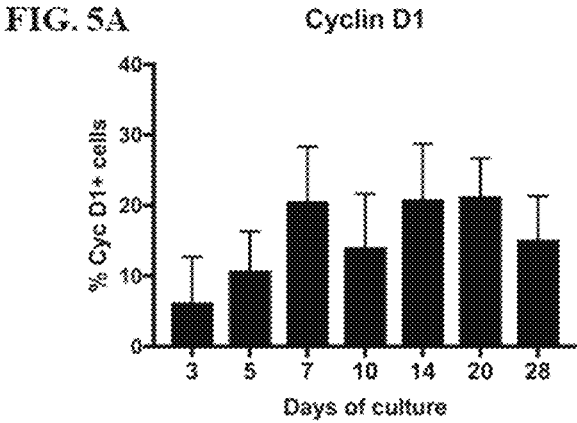
FIGS. 5A-5C illustrate the proliferation of HepaRG cells in 3D GelMa culture according to the method of the invention. 5A is a histogram showing the expression of the G1 phase marker cyclin D1 in HepaRG in 3D GelMa culture (expressed as the percentage of cyclin D1 positive cells). 5B is a histogram showing the expression of the S phase marker Ki67 in HepaRG cells in 3D GelMa culture (expressed as the percentage of Ki67 positive cells). 5C is a histogram showing the EdU nuclei incorporation in HepaRG in 3D GelMa culture (expressed as the percentage of EdU positive cells).

In the present invention, the following terms have the following meanings:

"About" preceding a figure encompasses plus or minus 10%, or less, of the value of said figure. It is to be understood that the value to which the term "about" refers is itself also specifically, and preferably, disclosed.

"Animal cells" refer to cells originating from a metazoan.

"Bile canaliculus" or "biliary canaliculus" refers to a 0.5- to 2-μm wide tissue space formed by the apical membranes of adjacent hepatocytes or hepatocyte-like cells. Bile canaliculi (or biliary canaliculi) are interconnected and form a network of minute intercellular channels that receive the bile secreted by the hepatocytes or hepatocyte-like cells.

"Bioprinting", also known as "three-dimensional (3D) printing" refers to a computer-aided transfer process for obtaining a 3D construct, which may be referred to as a 3D bioprinted construct, comprising live cells, biomaterials and/or biological molecules. Examples of bioprinting processes include for example extrusion or microextrusion bioprinting, inkjet bioprinting, laser-assisted bioprinting and stereolithography (Murphy & Atala, Nat Biotechnol. 2014 August; 32(8):773-85).

"Culture medium" refers to a liquid containing all the nutrients (e.g., salts, carbon sources, amino acids, minerals) required for cell survival and proliferation. Culture media may be supplemented with additional substances such as serum and serum components, vitamins, reducing agents, buffering agents, lipids, nucleosides, antibiotics, cytokines, and/or growth factors.

"Gelatin" refers to a collagen derivative, i.e., collagen hydrolyzed into shorter peptides corresponding to truncated collagen. Gelatin can also be defined as denatured collagen. Gelatin is obtained by hydrolysis of collagen such as type I collagen, in particular acidic or alkaline hydrolysis, which unfolds the triple-helical structures of collagen and results in the formation of shorter peptides. Gelatin thus possesses a very similar chemical composition to that of collagen, but a less ordered macromolecular structure. According to the present invention, the gelatin is methacrylated gelatin (GelMa).

"Gelatin matrix" refers to the three-dimensional matrix resulting from the formation of crosslinked structures, i.e., hydrogel, generated by the polymerization of gelatin, that is to say by the polymerization of truncated collagen. Thus, as used herein and unless mentioned otherwise, "gelatin matrix" refers to a 3D cross-linked gelatin matrix. According to the present invention, the gelatin is methacrylated gelatin (GelMa) and the gelatin matrix is a GelMa matrix.

"GelMa", "Gel-MA", or "Gel-Ma" refers to methacrylated gelatin, also known as gelatin methacryloyl, gelatin methacrylate or gelatin methacrylamide. GelMa is obtained by the direct reaction of gelatin with methacrylic anhydride, resulting in modification of lysine and hydroxyl residues with methacrylamide and methacrylate side groups (Yue et al., Biomaterials. 2015 December; 73:254-71).

"GelMa matrix" refers to the three-dimensional matrix resulting from the formation of crosslinked structures, i.e., hydrogel, generated by the polymerization of the methacrylated gelatin induced by a photoinitiator. Thus, as used herein and unless mentioned otherwise, "GelMa matrix" refers to a 3D cross-linked GelMa matrix.

"HepaRG cells" refers to cells of the human hepatoma-derived cell line deposit no. I-2652, filed by INSTITUT NATIONAL DE LA SANTE ET DE LA RECHER-CHE MEDICALE (INSERM), 101 rue de Tolbiac, F-75654 Paris Cedex 13, France, on 5 Apr. 2001 at the COLLECTION NATIONALE DE CULTURES DE MICROORGANISMES, INSTITUT PASTEUR, 25 rue du Docteur Roux, F-75724 Paris Cedex 15, France, described in EP1404816 and in U.S. Pat. No. 7,456, 018. The HepaRG cell line is a stable human hepatic progenitor cell line with morphological and functional characteristics of early hepatoblasts. Under appropriate culture conditions, the HepaRG cell line can give rise to differentiated hepatic cells, including hepatocytes or hepatocyte-like cells that retain many characteristics of primary human hepatocytes, and primitive biliary cells. Unless specified otherwise, HepaRG cells as used herein refer to undifferentiated human hepatic cells (i.e., human hepatic progenitors) of the stable HepaRG cell line.

"Hepatic cells" as used herein refer to liver cells such as parenchymal liver cells (e.g., hepatocytes) and non-parenchymal liver cells (e.g., Kupffer cells, cholangiocytes, liver fibroblasts, sinusoidal endothelial cells and hepatic stellate cells).

"Hepatic functions" as used herein refer to specific functions which are characteristic of the liver, and in particular of hepatocytes, including without being limited to, polarization, protein expression, protein secretion, bile secretion and enzymatic activities. Thus, hepatic functions characterizing hepatocytes may be assessed for example though the determination of the expression of albumin encoded by the gene ALB, aldolase B encoded by the gene ALDOB, alpha-1 antitrypsin (also referred to as alpha1AT, A1A, A1AT, AAT) encoded by the gene SERPINA1, and/or hepatocyte nuclear factor 4 alpha (HNF4A) encoded by the gene HNF4A; the determination of the secretion of albumin; the determination of the secretion of bile; the determination of the secretion of urea; the determination of the expression, intracellular localization and/or activity of xenobiotic metabolism enzymes such as phase I, phase II, and/or phase III enzymes; the determination of the expression, intracellular localization and/or activity of drug transporters such as MRP2 (multidrug resistance-associated protein 2) and/or MRP3 (multidrug resistance-associated protein 3).

"Hepatocyte" refers to a highly differentiated hepatic cell that carries out most of the hepatic functions, which pertain notably to bile secretion, glycogen synthesis, metabolism, detoxification and systemic homeostasis. Hepatocytes are polarized cells which have basal/sinusoidal domains facing liver sinusoidal endothelial cells; lateral domains; and one or more apical/canalicular domains that can contribute to several bile canaliculi jointly with the directly opposing hepatocytes.

"Hepatocyte-like cell" as used herein refers to differentiated hepatic cells able to recapitulate many, if not all, of the hepatic functions characterizing hepatocytes. In one embodiment, hepatocyte-like cells are characterized by at least one of the following:

secretion of albumin and/or urea;
synthesis of glycogen;
CYP1A2 metabolic activity;
expression of at least one of the following genes: ALB, HNF4A (hepatocyte nuclear factor 4 alpha), G6PC also known as G6PC1 (glucose-6-phosphatase catalytic subunit), SERPINA1 (coding for alpha-1 antitrypsin also known as alpha1AT), UGT1A1 (UDP glucuronosyltransferase family 1 member A1), and/or CYP1A2 (cytochrome P450 family 1 subfamily A member 2);
absence or low expression of at least one of the following genes: AFP (alpha fetoprotein), GPC3 (glypican 3), and/or H19.

"Passage" refers to the transfer of some or of all of the cells being cultured in vitro in a culture medium to a fresh culture medium. Passage is also known as subculture.

"Primary progenitors or cells" as used herein refers to progenitors or cells taken directly from living, non-cancerous tissue, such as for example, progenitors or cells obtained from a tissue sample of a subject or from a biopsy of a subject.

"Progenitors" or "progenitor cells" as used herein refers to undifferentiated or partially differentiated or immature cells which may give rise to differentiated cells. For example, HepaRG progenitors (i.e., undifferentiated HepaRG cells) may be differentiated into hepatocytes or hepatocyte-like cells.

"3D culture" as used hereinafter refers to the culture of stem cell-derived or immortalized human hepatic progenitors or cells embedded in a GelMa matrix according to the method of the invention. According to the invention, the stem cell-derived or immortalized human hepatic progenitors or cells are cultured in a GelMa matrix after having first been incubated in a non-adherent culture vessel, such as a low or ultra-low attachment culture vessel, and then transferred to a culture medium comprising GelMa. Thus, as used herein, "3D culture" corresponds to the third step of the method of the invention.

"3D cell structures comprising human hepatic cells" refer to 3D aggregates of human hepatic cells, in particular differentiate human hepatic cells. In one embodiment, the 3D cell structures are spheroids comprising human hepatic cells. In one embodiment, the 3D cell structures are spheroids comprising differentiated human hepatic cells. In one embodiment, the 3D cell structures are spheroids comprising human hepatocytes or hepatocyte-like cells.

The present invention relates to a method of culturing stem-cell derived or immortalized human hepatic progenitors or cells to obtain 3D cell structures comprising human hepatic cells, said method comprising:

a) culturing the stem-cell derived or immortalized human hepatic progenitors or cells in a non-adherent culture vessel, preferably a low or ultra-low attachment culture vessel;

b) transferring the stem-cell derived or immortalized human hepatic progenitors or cells to a culture medium comprising methacrylated gelatin (GelMa), thereby embedding the stem-cell derived or immortalized human hepatic progenitors or cells in a GelMa matrix; and c) covering the GelMa matrix with culture medium and culturing the stem-cell derived or immortalized human hepatic progenitors or cells embedded in the GelMa matrix;

thereby obtaining 3D cell structures comprising human hepatic cells.

According to one embodiment, the present invention relates to a method of culturing undifferentiated or partially differentiated cells human hepatic cells, said undifferentiated or partially differentiated cells human hepatic cells being stem cell-derived or immortalized cells, to obtain 3D cell structures comprising differentiated human hepatic cells, said method comprising:

a) culturing the undifferentiated or partially differentiated cells human hepatic cells in a non-adherent culture vessel, preferably a low or ultra-low attachment culture vessel;

b) transferring the undifferentiated or partially differentiated cells human hepatic cells to a culture medium comprising methacrylated gelatin (GelMa), thereby embedding the undifferentiated or partially differentiated cells human hepatic cells in a GelMa matrix; and c) covering the GelMa matrix with culture medium and culturing the undifferentiated or partially differentiated cells human hepatic cells embedded in the GelMa matrix;

thereby obtaining 3D cell structures comprising differentiated human hepatic cells.

According to one embodiment, the present invention relates to a method of culturing stem-cell derived or immortalized human hepatic progenitors to obtain 3D cell structures comprising differentiated human hepatic cells, said method comprising:

a) culturing the stem-cell derived or immortalized human hepatic progenitors in a non-adherent culture vessel, preferably a low or ultra-low attachment culture vessel;

b) transferring the stem-cell derived or immortalized human hepatic progenitors to a culture medium comprising methacrylated gelatin (GelMa), thereby embedding the stem-cell derived or immortalized human hepatic progenitors in a GelMa matrix; and c) covering the GelMa matrix with culture medium and culturing the stem-cell derived or immortalized human hepatic progenitors embedded in the GelMa matrix;

thereby obtaining 3D cell structures comprising differentiated human hepatic cells.

According to the present invention, stem-cell derived or immortalized human hepatic progenitors or cells are human hepatic progenitors or human hepatic cells that have an extended replicative capacity, in particular in comparison with the replicative capacity of corresponding primary human hepatic progenitors or cells.

According to one embodiment of the present invention, the replicative capacity of human hepatic progenitors or cells may be evaluated through the number of passages that said human hepatic progenitors or cells can undergo when cultured in vitro. In one embodiment, stem-cell derived or immortalized human hepatic progenitors or cells are human hepatic progenitors or human hepatic cells that can undergo at least 10 passages. In one embodiment, stem-cell derived or immortalized human hepatic progenitors or cells are human hepatic progenitors or human hepatic cells that can undergo a number of passages ranging from 10 to 400.

According to one embodiment, the stem-cell derived or immortalized human hepatic progenitors or cells are undifferentiated or partially differentiated cells human hepatic cells. Thus, according to one embodiment, the method of the invention is for culturing stem-cell derived or immortalized human hepatic progenitors. Examples of human hepatic progenitors include, without being limited to, undifferentiated or partially differentiated human hepatic cells which may give rise to differentiated human hepatic cells, such as human hepatocytes or hepatocyte-like cells and biliary cells.

In one embodiment, the stem-cell derived or immortalized human hepatic progenitors are stem-cell derived or immortalized human hepatic stem cells and/or immortalized human hepatoblasts.

According to another embodiment, the method of the invention is for culturing stem-cell derived or immortalized human hepatic cells.

Examples of human hepatic cells include, without being limited to, human hepatocytes or hepatocyte-like cells, human biliary cells, hepatic stellate cells (HSCs), liver sinusoidal endothelial cells (LSECs).

In one embodiment, the stem-cell derived or immortalized human hepatic cells are stem-cell derived or immortalized human hepatocytes or hepatocyte-like cells.

According to one embodiment, stem-cell derived or immortalized human hepatic progenitors or cells include, without being limited to, stem cell-derived human hepatic progenitors or cells, tumor-derived human hepatic progenitors or cells (that is to say human hepatic progenitors or cells derived from a cancerous tumor, i.e., cancerous cell lines), and/or transformed human hepatic progenitors or cells.

In one embodiment, the stem-cell derived or immortalized human hepatic progenitors or cells are stem cell-derived human hepatic progenitors or cells, hepatocellular carcinoma-derived human hepatic progenitors or cells (also known as hepatoma-derived human hepatic progenitors or cells), and/or transformed human hepatic progenitors or cells.

As used herein, transformed human hepatic progenitors or cells refer to human hepatic progenitors or cells resulting from the transformation of progenitors or cells with a viral gene such as EBV (Epstein-Barr virus) gene, HPV-16 (human papillomavirus) E6/7 gene, or the Simian Virus 40

(SV40) T antigens or with a so-called immortality gene such as the gene encoding hTERT (human Telomerase Reverse Transcriptase).

In one embodiment, the transformed human hepatic progenitors or cells result from the transformation of tumor-derived progenitors or cells.

Examples of stem cell-derived human hepatic progenitors or cells include, without being limited to, iPSC-derived (induced pluripotent stem cell-derived) human hepatic progenitors or cells, such as iPSC-derived hepatoblasts or iPSC-derived hepatocytes.

In one embodiment, the stem cell-derived human hepatic progenitors or cells are iPSC-derived human hepatic progenitors or cells.

Examples of hepatocellular carcinoma-derived human hepatic progenitors or cells (also known as hepatoma-derived human hepatic progenitors or cells) include, without being limited to, HepaRG cells, HuH-7 cells.

Examples of transformed human hepatic progenitors or cells include, without being limited to, Fa2N-4 cells, HepLi5 cells.

According to one embodiment, the method of the invention is for culturing stem cell-derived, in particular iPSC-derived, human hepatic progenitors or cells as described above.

According to one embodiment, the method of the invention is for culturing iPSC-derived or immortalized human hepatic progenitors or cells as described above.

According to one embodiment, the method of the invention is for culturing immortalized human hepatic progenitors or cells as described above.

In one embodiment of the present invention, immortalized human hepatic progenitors or cells do not include stem-cell derived human hepatic progenitors or cells.

Thus, in one embodiment of the present invention, the method of the invention is for culturing immortalized human hepatic progenitors or cells including, without being limited to, hepatocellular carcinoma-derived human hepatic progenitors or cells (also known as hepatoma-derived human hepatic progenitors or cells) and transformed human hepatic progenitors or cells.

In one embodiment, the immortalized human hepatic progenitors or cells are hepatocellular carcinoma-derived human hepatic progenitors or cells (also known as hepatoma-derived human hepatic progenitors or cells) and/or transformed human hepatic progenitors or cells.

In one embodiment, the immortalized human hepatic progenitors or cells are transformed hepatocellular carcinoma-derived human hepatic progenitors or cells (also known as transformed hepatoma-derived human hepatic progenitors or cells).

In one embodiment, hepatocellular carcinoma-derived human hepatic progenitors (also known as hepatoma-derived human hepatic progenitors) include, without being limited to, undifferentiated HepaRG cells (i.e., HepaRG progenitors).

In one embodiment, hepatocellular carcinoma-derived human hepatic cells (also known as hepatoma-derived human hepatic cells) include, without being limited to, differentiated HepaRG cells, HuH-7 cells, HepG2 cells.

In one embodiment, transformed human hepatic cells include, without being limited to, Fa2N-4 cells, HepLi5 cells.

According to a particular embodiment, the method of the invention is for culturing HepaRG cells, in particular undifferentiated HepaRG cells, HuH-7 cells, HepG2 cells, Fa2N-4 cells or HepLi5 cells. In one embodiment, the method of the invention is for culturing HepaRG cells, in particular undifferentiated HepaRG cells (i.e., HepaRG progenitors), or HuH-7 cells.

According to a particular embodiment, the method of the invention is for culturing HepaRG cells, in particular undifferentiated HepaRG cells (i.e., HepaRG progenitors).

As mentioned hereinabove, undifferentiated HepaRG cells refers to cells of the human hepatoma-derived cell line deposit no. I-2652, filed by INSTITUT NATIONAL DE LA SANTE ET DE LA RECHERCHE MEDICALE (IN-SERM), 101 rue de Tolbiac, F-75654 Paris Cedex 13, France, on 5 Apr. 2001 at the COLLECTION NATIONALE DE CULTURES DE MICROORGANISMES, INSTITUT PASTEUR, 25 rue du Docteur Roux, F-75724 Paris Cedex 15, described in EP1404816 and in U.S. Pat. No. 7,456,018.

In one embodiment, the stem-cell derived or immortalized human hepatic progenitors or cells to be cultured with the method of the invention were stored frozen. Thus, in one embodiment, the stem-cell derived or immortalized human hepatic progenitors or cells to be cultured with the method of the invention are first thawed. Methods to thaw previously frozen stem-cell derived or immortalized human hepatic progenitors or cells are well-known in the field of cell culture.

According to the method of the invention, stem-cell derived or immortalized human hepatic progenitors or cells as described above are first cultured in a non-adherent culture vessel.

As used herein, the term "non-adherent culture vessel" refers to a culture vessel that is not conductive to the attachment of cells, in particular stem-cell derived or immortalized human hepatic progenitors or cells as described above, to said vessel. In other words, cells, in particular stem-cell derived or immortalized human hepatic progenitors or cells as described above, being cultured in a non-adherent culture vessel do not attach, or very little, and do not spread to the inner surface of said culture vessel (i.e., to the walls and/or bottom of said culture vessel). Non-adherent culture vessels include, without being limited to, culture vessels made of glass, untreated culture vessels, low attachment culture vessels, and ultra-low attachment culture vessels.

As used herein, the term "untreated culture vessel" refers to a culture vessel that did not undergo the chemical treatment or the coating commonly applied to culture vessels in order to enhance cell attachment to the culture vessels. In the field of cell culture, "treated culture vessel" commonly refers to a culture vessel, such as a plate or a dish, usually made of polystyrene, that underwent a chemical treatment or a coating in order to enhance the attachment of cells, in particular stem cell-derived or immortalized human hepatic progenitors or cells, to the inner surface of the culture vessel. Indeed, polystyrene is a very hydrophobic polymer to which cells, in particular stem-cell derived or immortalized human hepatic progenitors or cells as described above, have difficulty attaching.

In one embodiment, the non-adherent culture vessel as described above is selected from the group comprising or consisting of culture vessels made of glass, untreated culture vessels, low attachment culture vessels and ultra-low attachment culture vessels; preferably said non-adherent culture vessel is a low or ultra-low attachment culture vessel. Examples of low and ultra-low attachment culture vessels include, without being limited to, low and ultra-low attachment dishes, low and ultra-low attachment flasks and low and ultra-low attachment plates, such as, for example, low and ultra-low attachment multi-well plates or low and ultra-low attachment microplates.

Low attachment culture vessels and ultra-low attachment culture vessels are characterized by the presence of a coating, usually a hydrophilic gel, that is covalently bound to the inner surface of the culture vessel. Said coating inhibits specific and nonspecific immobilization and thus prevents cell attachment to the inner surface of the culture vessel, thereby maintaining cells into a suspended state. Low and ultra-low attachment culture vessels, in particular low attachment plates (LAP) and ultra-low attachment (ULA) plates, are readily available from suppliers and include, for example, Corning® Costar®, InSphero®, S-Bio® or Perkin Elmer® low and ultra-low attachment plates. Alternatively, methods to prepare low attachment culture vessels, in particular low attachment plates, are well-known to those skilled in the art. Such methods include, without being limited to, coating untreated culture vessels with 1% agarose or coating untreated culture vessels with poly-2-hydroxy-ethyl methacrylate (also referred to as poly-HEMA).

In one embodiment, the stem-cell derived or immortalized human hepatic progenitors or cells as described above to be cultured with the method of the invention are first cultured in a low attachment plate (LAP) or in an ultra-low attachment plate (ULA) such as, for example, Corning® Costar®, InSphero®, S-Bio® or Perkin Elmer® low or ultra-low attachment plates.

In one embodiment, the stem-cell derived or immortalized human hepatic progenitors or cells as described above are cultured in the non-adherent culture vessel as described above for at least about 1 h, 2 h, 3 h, 4 h, 5 h, 6 h, 7 h, 8 h, 9 h, 10 h, 11 h, 12 h, 13 h, 14 h, or 15 h. In one embodiment, the stem-cell derived or immortalized human hepatic progenitors or cells as described above are cultured in the non-adherent culture vessel as described above for at most about 96 h, 84 h, 72 h, 60 h, 48 h, 36 h, 24 h, 23 h, 22 h, 21 h, or 20 h.

In one embodiment, the stem-cell derived or immortalized human hepatic progenitors or cells as described above are cultured in the non-adherent culture vessel as described above for a duration ranging from about 1 h to about 96 h, preferably from about 5 h to about 72 h, more preferably from about 10 h to about 48 h, even more preferably from about 12 h to about 48 h. In one embodiment, the stem-cell derived or immortalized human hepatic progenitors or cells as described above are cultured in the non-adherent culture vessel as described above for a duration ranging from about 12 h to about 24 h.

In one embodiment, the stem-cell derived or immortalized human hepatic progenitors or cells as described above are cultured in the non-adherent culture vessel as described above for about 10 h, 11 h, 12 h, 13 h, 14 h, 15 h, 16 h, 17 h, 18 h, 19 h, 20 h, 22 h, 24 h, 26 h, 28 h, 30 h, 32 h, 34 h, 36 h, 38 h, 40 h, 42 h, 44 h, 46 h, or 48 h.

In one embodiment, the stem-cell derived or immortalized human hepatic progenitors or cells as described above are cultured in the non-adherent culture vessel as described above at a concentration of at least about $10^2$, $5 \times 10^2$, or $10^3$ cells per $cm^2$. In one embodiment, the stem-cell derived or immortalized human hepatic progenitors or cells as described above are cultured in the non-adherent culture vessel as described above at a concentration of at most about $5 \times 10^6$, $10^6$ or $5 \times 10^5$ cells per $cm^2$.

In one embodiment, the stem-cell derived or immortalized human hepatic progenitors or cells as described above are cultured in the non-adherent culture vessel as described above at a concentration ranging from about $10^2$ to about $5\times10^6$ cells per cm$^2$, preferably from about $10^3$ to about $10^6$ cells per cm$^2$, more preferably from about $10^4$ to about $5\times10^5$ cells per cm$^2$, even more preferably from about $10^5$ to about $2\times10^5$ cells per cm$^2$.

In one embodiment, the stem-cell derived or immortalized human hepatic progenitors or cells as described above are cultured in the non-adherent culture vessel as described above, at a concentration of about $5\times10^4$, $6\times10^4$, $7\times10^4$, $8\times10^4$, $9\times10^4$, $10^5$, $2\times10^5$, $3\times10^5$, $4\times10^5$, $5\times10^5$ per cm$^2$, preferably of about $10^5$ or $2\times10^5$ cells per cm$^2$.

In one embodiment, the stem-cell derived or immortalized human hepatic progenitors or cells as described above are cultured in a low or ultra-low attachment plate at a concentration ranging from about $5\times10^5$ to about $5\times10^6$ cells per well, preferably from about $10^6$ to about $2\times10^6$ cells per well, said well preferably having a surface of about 10 cm$^2$.

In one embodiment, the stem-cell derived or immortalized human hepatic progenitors or cells as described above are cultured in the non-adherent culture vessel as described above at a concentration of at least about $10^3$, $5\times10^3$ or $10^4$ cells per ml of culture medium. In one embodiment, the stem-cell derived or immortalized human hepatic progenitors or cells as described above are cultured in the non-adherent culture vessel as described above at a concentration of at most about $5\times10^7$, $10^7$, or $5\times10^6$ cells per ml of culture medium.

In one embodiment, the stem-cell derived or immortalized human hepatic progenitors or cells as described above are cultured in the non-adherent culture vessel as described above at a concentration ranging from about $10^3$ to about $5\times10^7$ cells per ml of culture medium, preferably from about $10^4$ to about $10^7$ cells per ml of culture medium, more preferably from about $10^5$ to about $10^6$ cells per ml of culture medium, even more preferably from about from about $3\times10^5$ to about $6\times10^5$ cells per ml of culture medium.

In one embodiment, the stem-cell derived or immortalized human hepatic progenitors or cells as described above are cultured in the non-adherent culture vessel as described above at a concentration of about $10^4$, $5\times10^4$, $10^5$, $5\times10^5$, $10^6$, $5\times10^6$ or $10^7$ cells per ml of culture medium. In one embodiment, the stem-cell derived or immortalized human hepatic progenitors or cells as described above are cultured in the non-adherent culture vessel as described above at a concentration of about $10^5$, $2\times10^5$, $3\times10^5$, $4\times10^5$, $5\times10^5$, $6\times10^5$, $7\times10^5$, $8\times10^5$, $9\times10^5$, $10^6$ cells per ml of culture medium, preferably of about $3\times10^5$, $4\times10^5$, $5\times10^5$ or $6\times10^5$ cells per ml of culture medium.

Selecting conditions suitable for the culture of stem-cell derived or immortalized human hepatic progenitors or cells as described above in order to obtain human hepatic cells, in particular differentiated human hepatic cells, is well-known to those skilled in the art. Thus, the culture conditions to be used for culturing stem-cell derived or immortalized human hepatic progenitors or cells as described above in the non-adherent culture vessel according to the method of the invention, such as, for example, culture medium, temperature, humidity and levels of $CO_2$, will be apparent to those having skill in the art and will depend on the stem-cell derived or immortalized human hepatic progenitors or cells to be cultured.

Culture media that may be used according to the method of the invention include natural media and synthetic media, such as, for example, serum-containing media, serum-free media, xeno-free media notably for human cell culture, protein-free media, chemically defined media. Examples of culture media include, without being limited to, William's E medium, Basal Medium Eagle (BME), Eagle's Minimum Essential Medium (EMEM), Minimum Essential Medium (MEM), Dulbecco's Modified Eagles Medium (DMEM), Ham's F-10, Ham's F-12 medium, Kaighn's modified Ham's F-12 medium, DMEM/F-12 medium, and McCoy's 5A medium.

In a particular embodiment, culture media according to the present invention also include media conducive to the culture of human hepatic cells, in particular differentiated human hepatic cells, such as human hepatocytes or hepatocyte-like cells. Examples of media conducive to the culture of human hepatic cells, in particular differentiated human hepatic cells, such as human hepatocytes or hepatocyte-like cells, include, without being limited to, Dulbecco's Modified Eagles Medium (DMEM), William's E Medium, Hepatocyte Culture Medium, Basal HepaRG Medium, HBM Basal Medium, and Hepatocyte Basal Medium.

According to the present invention, the culture medium may be supplemented with additional substances such as salts, carbon sources, amino acids, serum and serum components, vitamins, minerals, reducing agents, buffering agents, lipids, nucleosides, antibiotics, cytokines, and/or growth factors.

In one embodiment, the culture medium conducive to the culture of human hepatic cells, in particular differentiated human hepatic cells, such as human hepatocytes or hepatocyte-like cells, is a medium supplemented with at least one of gentamicin, penicillin, streptomycin, insulin (preferably human insulin), L-glutamine, hydrocortisone (such as hydrocortisone hemisuccinate) or dexamethasone, and FCS (fetal calf serum) also referred to as FBS (fetal bovine serum).

In one embodiment, the culture medium conducive to the culture of human hepatic cells, in particular differentiated human hepatic cells, such as human hepatocytes or hepatocyte-like cells, is a medium supplemented with penicillin, streptomycin, insulin (preferably human insulin), L-glutamine, and hydrocortisone (such as hydrocortisone hemisuccinate), and optionally with FCS (fetal calf serum) also referred to as FBS (fetal bovine serum).

In one embodiment, the stem-cell derived or immortalized human hepatic progenitors or cells as described above are cultured in a low or ultra-low attachment culture vessel, preferably a low or ultra-low attachment plate, in William's E Medium supplemented with penicillin, streptomycin, insulin (preferably human insulin), L-glutamine, and hydrocortisone (such as hydrocortisone hemisuccinate), and optionally with FCS (fetal calf serum) also referred to as FBS (fetal bovine serum).

In one embodiment, the stem-cell derived or immortalized human hepatic progenitors or cells as described above are cultured in a low or ultra-low attachment culture vessel, preferably a low or ultra-low attachment plate, in William's E Medium supplemented with penicillin, streptomycin, insulin (preferably human insulin), L-glutamine, hydrocortisone (such as hydrocortisone hemisuccinate) and with FCS (fetal calf serum) also referred to as FBS (fetal bovine serum).

In one embodiment, the stem-cell derived or immortalized human hepatic progenitors or cells as described above are cultured in a low or ultra-low attachment culture vessel, preferably a low or ultra-low attachment plate, in a medium, preferably William's E Medium, supplemented with penicillin at a concentration ranging from about 50 to about 200 U/mL, preferably about 100 U/mL; streptomycin at a concentration ranging from about 1 to about 200 µg/mL, preferably 5 µg/mL; insulin, preferably human insulin, at a concentration ranging from about 1 to about 30 μg/mL, preferably about 5 μg/mL; glutamine (L-glutamine) at a concentration ranging from about 1 to about 10 mM, preferably about 2 mM; and hydrocortisone (such as hydrocortisone hemisuccinate) at a concentration ranging from about 0.1 to about 100 μM, preferably about 50 μM; and optionally FCS (fetal calf serum) at a concentration ranging from about 0 to about 20% (v/v), and preferably about 10% (v/v).

In one embodiment, the stem-cell derived or immortalized human hepatic progenitors or cells as described above are cultured in a low or ultra-low attachment culture vessel, preferably a low or ultra-low attachment plate, in a medium, preferably William's E Medium, supplemented with penicillin at a concentration ranging from about 50 to about 200 U/mL, preferably about 100 U/mL; streptomycin at a concentration ranging from about 1 to about 200 μg/mL, preferably 5 μg/mL; insulin, preferably human insulin, at a concentration ranging from about 1 to about 30 μg/mL, preferably about 5 μg/mL; glutamine (L-glutamine) at a concentration ranging from about 1 to about 10 mM, preferably about 2 mM; hydrocortisone (such as hydrocortisone hemisuccinate) at a concentration ranging from about 0.1 to about 100 μM, preferably about 50 μM; and FCS (fetal calf serum) at a concentration ranging from about 1 to about 20% (v/v), and preferably about 10% (v/v).

According to the method of the invention, the stem-cell derived or immortalized human hepatic progenitors or cells as described above may be pre-cultured before being cultured in a non-adherent culture vessel.

In one embodiment, the stem-cell derived or immortalized human hepatic progenitors or cells as described above are undifferentiated HepaRG (i.e., HepaRG progenitors) which are pre-cultured before being cultured in a non-adherent culture vessel.

In one embodiment, the stem-cell derived or immortalized human hepatic progenitors or cells as described above, in particular undifferentiated HepaRG (i.e., HepaRG progenitors), are pre-cultured in a medium, preferably William's E Medium, supplemented with penicillin at a concentration ranging from about 50 to about 200 U/mL, preferably about 100 U/mL; streptomycin at a concentration ranging from about 1 to about 200 μg/mL, preferably 5 μg/mL; insulin, preferably human insulin, at a concentration ranging from about 1 to about 30 μg/mL, preferably about 5 μg/mL; glutamine (L-glutamine) at a concentration ranging from about 1 to about 10 mM, preferably about 2 mM; hydrocortisone (such as hydrocortisone hemisuccinate) at a concentration ranging from about 0.1 to about 100 μM, preferably about 50 μM; and FCS (fetal calf serum) at a concentration ranging from about 1 to about 20% (v/v), and preferably about 10% (v/v).

In one embodiment, the stem-cell derived or immortalized human hepatic progenitors or cells as described above, in particular undifferentiated HepaRG (i.e., HepaRG progenitors), are pre-cultured for at least 5, 6, 7, 8, 9, 10, 11 or 12 days.

In one embodiment, the stem-cell derived or immortalized human hepatic progenitors or cells as described above, in particular undifferentiated HepaRG (i.e., HepaRG progenitors), are pre-cultured for about 5, 6, 7, 8, 9, 10, 11, 12, 13, 14 days, preferably for about 14 days.

Thus, in one embodiment, the method of the invention comprises pre-culturing stem-cell derived or immortalized human hepatic progenitors or cells as described above, in particular undifferentiated HepaRG (i.e., HepaRG progenitors), in a medium, preferably William's E Medium, supplemented with penicillin at a concentration ranging from about 50 to about 200 U/mL, preferably about 100 U/mL; streptomycin at a concentration ranging from about 1 to about 200 μg/mL, preferably 5 μg/mL; insulin, preferably human insulin, at a concentration ranging from about 1 to about 30 μg/mL, preferably about 5 μg/mL; glutamine (L-glutamine) at a concentration ranging from about 1 to about 10 mM, preferably about 2 mM; hydrocortisone (such as hydrocortisone hemisuccinate) at a concentration ranging from about 0.1 to about 100 μM, preferably about 50 μM; and FCS (fetal calf serum) at a concentration ranging from about 1 to about 20% (v/v), and preferably about 10% (v/v), for about 14 days and then:

a) culturing the stem-cell derived or immortalized human hepatic progenitors or cells as described above, in particular undifferentiated HepaRG (i.e., HepaRG progenitors), in a non-adherent culture vessel, preferably a low or ultra-low attachment culture vessel, in a medium, preferably William's E Medium, supplemented with penicillin at a concentration ranging from about 50 to about 200 U/mL, preferably about 100 U/mL; streptomycin at a concentration ranging from about 1 to about 200 μg/mL, preferably 5 μg/mL; insulin, preferably human insulin, at a concentration ranging from about 1 to about 30 μg/mL, preferably about 5 μg/mL; glutamine (L-glutamine) at a concentration ranging from about 1 to about 10 mM, preferably about 2 mM; hydrocortisone (such as hydrocortisone hemisuccinate) at a concentration ranging from about 0.1 to about 100 μM, preferably about 50 μM; and FCS (fetal calf serum) at a concentration ranging from about 1 to about 20% (v/v), and preferably about 10% (v/v), for a period ranging from about 1 h to about 96 h;

b) transferring the stem-cell derived or immortalized human hepatic progenitors or cells as described above, in particular undifferentiated HepaRG (i.e., HepaRG progenitors), to a culture medium comprising methacrylated gelatin (GelMa), thereby embedding the stem-cell derived or immortalized human hepatic progenitors or cells, in particular undifferentiated HepaRG (i.e., HepaRG progenitors), in a GelMa matrix; and c) covering the GelMa matrix with culture medium and culturing the stem-cell derived or immortalized human hepatic progenitors or cells as described above, in particular undifferentiated HepaRG (i.e., HepaRG progenitors), embedded in the GelMa matrix;

thereby obtaining 3D cell structures comprising human hepatic cells, in particular differentiated human hepatic cells.

According to the method of the invention, after being first cultured in a non-adherent culture vessel as described above, the stem-cell derived or immortalized human hepatic progenitors or cells as described above are transferred to a culture medium comprising methacrylated gelatin (also referred to as GelMa), and are thus embedded in a methacrylated gelatin matrix (also referred to as GelMa matrix).

In one embodiment, GelMa is obtained by the methacrylation of gelatin with methacrylic anhydride.

In one embodiment, the stem-cell derived or immortalized human hepatic progenitors or cells as described above are transferred to a culture medium comprising GelMa at a concentration of at least about 1% (w/v), 2% (w/v), 2.5% (w/v), 3% (w/v), 4% (w/v) or 5% (w/v). Thus, in one embodiment, the stem-cell derived or immortalized human hepatic progenitors or cells as described above are transferred to a culture medium comprising GelMa at a concentration of at least about 10 mg/mL, 20 mg/mL, 25 mg/mL, 30 mg/mL, 40 mg/mL or 50 mg/mL.

In one embodiment, the stem-cell derived or immortalized human hepatic progenitors or cells as described above are transferred to a culture medium comprising GelMa at a concentration of at most about 20% (w/v), 15% (w/v), 10% (w/v), 9% (w/v), 8% (w/v), 7% (w/v), 7.5% (w/v), 6% (w/v) or 5% (w/v). Thus, in one embodiment, the stem-cell derived or immortalized human hepatic progenitors or cells as described above are transferred to a culture medium comprising GelMa at a concentration of at most about 200 mg/mL, 150 mg/mL, 100 mg/mL, 90 mg/mL, 80 mg/mL, 70 mg/mL, 75 mg/mL, 60 mg/mL or 50 mg/mL.

In one embodiment, the stem-cell derived or immortalized human hepatic progenitors or cells as described above are transferred to a culture medium comprising GelMa at a concentration ranging from about 1% (w/v) to about 20% (w/v), preferably from about 2% (w/v) to about 10% (w/v), more preferably from about 2.5% (w/v) to about 7.5% (w/v), even more preferably from about 2.5% (w/v) to about 5% (w/v). Thus, in one embodiment, the stem-cell derived or immortalized human hepatic progenitors or cells as described above are transferred to a culture medium comprising GelMa at a concentration ranging from about 10 mg/mL to about 200 mg/mL, preferably from about 20 mg/mL to about 100 mg/mL, more preferably from about 25 mg/mL to about 75 mg/mL, even more preferably from about 25 mg/mL to about 50 mg/mL.

In one embodiment, the stem-cell derived or immortalized human hepatic progenitors or cells as described above are transferred to a culture medium comprising GelMa at a concentration of about 2.5% (w/v) or about 5% (w/v), i.e., at a concentration of about 25 mg/mL or about 50 mg/mL.

In one embodiment, the stem-cell derived or immortalized human hepatic progenitors or cells as described above are transferred to a culture medium comprising GelMa at a concentration of about 5% (w/v), i.e., at a concentration of about 50 mg/mL.

In one embodiment, the concentration of methacrylated gelatin comprised in the culture medium as described hereinabove is referred to as the final concentration of methacrylated gelatin in the culture medium.

In one embodiment, the culture medium in which GelMa is added to obtain a culture medium comprising GelMa and the culture medium previously used to culture the stem-cell derived or immortalized human hepatic progenitors or cells in a non-adherent culture vessel as described hereinabove are different media. In another embodiment, the culture medium in which GelMa is added to obtain a culture medium comprising GelMa and the culture medium previously used to culture the stem-cell derived or immortalized human hepatic progenitors or cells in a non-adherent culture vessel as described hereinabove are the same medium.

As mentioned hereinabove, the culture medium to be used according to the method of the invention will be apparent to those skilled in the art and will depend on the stem-cell derived or immortalized human hepatic progenitors or cells to be cultured. Culture media that may be used according to the method of the invention are described above.

In one embodiment, the culture medium in which GelMa is added to obtain a culture medium comprising GelMa is a medium conducive to the culture of human hepatic cells, in particular differentiated human hepatic cells, such as human hepatocytes or hepatocyte-like cells. Examples of media conducive to the culture of human hepatic cells, in particular differentiated human hepatic cells, such as human hepatocytes or hepatocyte-like cells, are listed above. Thus, in one embodiment, the stem-cell derived or immortalized human hepatic progenitors or cells as described above are transferred in a medium conducive to the culture of human hepatic cells, in particular differentiated human hepatic cells, such as human hepatocytes or hepatocyte-like cells, said medium comprising GelMa as described above.

In one embodiment, the culture medium in which GelMa is added to obtain a culture medium comprising GelMa is a medium conducive to the culture of human hepatic cells, in particular differentiated human hepatic cells, such as human hepatocytes or hepatocyte-like cells, supplemented with at least one of gentamicin, penicillin, streptomycin, insulin (preferably human insulin), L-glutamine, hydrocortisone (such as hydrocortisone hemisuccinate) or dexamethasone, and FCS (fetal calf serum) also referred to as FBS (fetal bovine serum).

In one embodiment, the culture medium in which GelMa is added to obtain a culture medium comprising GelMa is a medium conducive to the culture of human hepatic cells, in particular differentiated human hepatic cells, such as human hepatocytes or hepatocyte-like cells, supplemented with penicillin, streptomycin, insulin (preferably human insulin), L-glutamine, and hydrocortisone (such as hydrocortisone hemisuccinate), and optionally with FCS (fetal calf serum) also referred to as FBS (fetal bovine serum).

In one embodiment, the culture medium in which GelMa is added to obtain a culture medium comprising GelMa is William's E Medium supplemented with penicillin, streptomycin, insulin (preferably human insulin), L-glutamine, and hydrocortisone (such as hydrocortisone hemisuccinate), and optionally with FCS (fetal calf serum) also referred to as FBS (fetal bovine serum).

In one embodiment, the culture medium in which GelMa is added to obtain a culture medium comprising GelMa is William's E Medium supplemented with penicillin, streptomycin, insulin (preferably human insulin), L-glutamine, hydrocortisone (such as hydrocortisone hemisuccinate) and with FCS (fetal calf serum) also referred to as FBS (fetal bovine serum).

In one embodiment, the culture medium in which GelMa is added to obtain a culture medium comprising GelMa is a medium, preferably William's E Medium, supplemented with penicillin at a concentration ranging from about 50 to about 200 U/mL, preferably about 100 U/mL; streptomycin at a concentration ranging from about 1 to about 200 µg/mL, preferably 5 µg/mL; insulin, preferably human insulin, at a concentration ranging from about 1 to about 30 µg/mL, preferably about 5 µg/mL; glutamine (L-glutamine) at a concentration ranging from about 1 to about 10 mM, preferably about 2 mM; and hydrocortisone (such as hydrocortisone hemisuccinate) at a concentration ranging from about 0.1 to about 100 µM, preferably about 50 µM; and optionally FCS (fetal calf serum) at a concentration ranging from about 0 to about 20% (v/v), and preferably about 10% (v/v).

In one embodiment, the stem-cell derived or immortalized human hepatic progenitors or cells as described above are transferred to a culture medium comprising GelMa as described above and further comprising a photoinitiator to induce polymerization upon light exposure. Examples of photoinitiators include, without being limited to, 2,2'-azobis [2-methyl-n-(2-hydroxyethyl)propionamide] (also known as VA-086, CAS number 61551-69-7), 1-[4-(2-hydroxyethoxy)-phenyl]-2-hydroxy-2-methyl-1-propanone (also known as Irgacure 2959, CAS number 106797-53-9), lithium phenyl-2,4,6-trimethylbenzoylphosphinate (also known as LAP or BioKey, CAS number 85073-19-4), 2',4', 5',7'-tetrabromofluorescein disodium salt (also known as eosin Y or EY, CAS number 17372-87-1), tris(2,2-bipyridyl) dichlororuthenium(II) hexahydrate and sodium persulfate (also known as ruthenium (Ru)/sodium persulfate (SPS)), 1-hydroxy-cyclohexyl-phenyl-ketone (also known as Irgacure 184, CAS number 947-19-3), 2,2 dimethoxy-2-phenylacetophenone (also known as Irgacure 651, CAS number 24650-42-8), 2-methyl-4'-(methylthio)-2-morpholinopropiophenone (also known as Irgacure 907, CAS number 71868-10-5), and 2,3-bornanedione or bornane-2,3-dione (also known as camphorquinone, CAS number 10373-78-1).

In one embodiment, the photoinitiator is selected from the group comprising or consisting of 2,2'-azobis[2-methyl-n-(2-hydroxyethyl)propionamide] (also known as VA-086), 1-[4-(2-hydroxyethoxy)-phenyl]-2-hydroxy-2-methyl-1-propanon (also known as Irgacure 2959), lithium phenyl-2,4,6-trimethylbenzoylphosphinate (also known as LAP or BioKey), 2',4',5',7'-tetrabromofluorescein disodium salt (also known as eosin Y or EY), tris(2,2-bipyridyl)dichlororuthenium(II) hexahydrate and sodium persulfate (also known as ruthenium (Ru)/sodium persulfate (SPS)), 1-hydroxy-cyclohexyl-phenyl-ketone (also known as Irgacure 184), 2,2 dimethoxy-2-phenylacetophenone (also known as Irgacure 651), 2-methyl-4'-(methylthio)-2-morpholinopropiophenone (also known as Irgacure 907), and 2,3-bornanedione or bornane-2,3-dione (also known as camphorquinone), preferably the photoinitiator is lithium phenyl-2,4,6-trimethylbenzoylphosphinate (also known as LAP or BioKey). In one embodiment, the photoinitiator is lithium phenyl-2,4,6-trimethylbenzoylphosphinate (also known as LAP or BioKey).

In one embodiment, the stem-cell derived or immortalized human hepatic progenitors or cells as described above are transferred to a culture medium comprising GelMa as described above and further comprising a photoinitiator as described hereinabove at a concentration of at least about 0.01% (w/v), 0.05% (w/v), 0.075% (w/v), 0.1% (w/v), 0.25% (w/v), 0.3% (w/v) or 0.5% (w/v). Thus, in one embodiment, the stem-cell derived or immortalized human hepatic progenitors or cells as described above are transferred to a culture medium comprising GelMa as described above and further comprising a photoinitiator as described hereinabove at a concentration of at least about 0.1 mg/mL, 0.5 mg/mL, 0.75 mg/mL, 1 mg/mL, 2.5 mg/mL, 3 mg/mL or 5 mg/mL.

In one embodiment, the stem-cell derived or immortalized human hepatic progenitors or cells as described above are transferred to a culture medium comprising GelMa as described above and further comprising a photoinitiator as described hereinabove at a concentration of at most about 10% (w/v), 5% (w/v), 2% (w/v), 1.5% (w/v), 1% (w/v), 0.75% (w/v), 0.5% (w/v), 0.25% (w/v), 0.1% (w/v) or 0.05% (w/v). Thus, in one embodiment, the stem-cell derived or immortalized human hepatic progenitors or cells as described above are transferred to a culture medium comprising GelMa as described above and further comprising a photoinitiator as described hereinabove at a concentration of at most about 100 mg/mL, 50 mg/mL, 20 mg/mL, 15 mg/mL, 10 mg/mL, 7.5 mg/mL, 5 mg/mL, 2.5 mg/mL, 1 mg/mL or 0.5 mg/mL.

In one embodiment, the stem-cell derived or immortalized human hepatic progenitors or cells as described above are transferred to a culture medium comprising GelMa as described above and further comprising a photoinitiator as described above at a concentration ranging from about 0.01% (w/v) to about 5% (w/v), preferably from about 0.025% (w/v) to about 2% (w/v), more preferably from about 0.05% (w/v) to about 1% (w/v), even more preferably from about 0.05% (w/v) to about 0.5% (w/v), most preferably from about 0.1% (w/v) to about 0.3% (w/v). Thus, in one embodiment, the stem-cell derived or immortalized human hepatic progenitors or cells as described above are transferred to a culture medium comprising GelMa as described above and further comprising a photoinitiator as described above at a concentration ranging from about 0.1 mg/mL to about 50 mg/mL, preferably from about 0.25 mg/mL to about 20 mg/mL, more preferably from about 0.5 mg/mL to about 10 mg/mL, even more preferably from about 0.5 mg/mL to about 5 mg/mL, most preferably from about 1 mg/mL to about 3 mg/mL.

In one embodiment, the stem-cell derived or immortalized human hepatic progenitors or cells as described above are transferred to a culture medium comprising GelMa as described above and further comprising a photoinitiator as described hereinabove at a concentration of about 0.1% (w/v) or about 0.3% (w/v), i.e., at a concentration of about 1 mg/mL or about 3 mg/mL.

In one embodiment, the stem-cell derived or immortalized human hepatic progenitors or cells as described above are transferred to a culture medium comprising GelMa at a concentration ranging from about 2.5% (w/v) to about 5% (w/v), i.e., at a concentration ranging from about 25 mg/mL to about 50 mg/mL; and further comprising a photoinitiator as described above, such as lithium phenyl-2,4,6-trimethylbenzoylphosphinate (also known as LAP or BioKey), at a concentration ranging from about 0.05% (w/v) to about 0.5% (w/v), i.e., at a concentration ranging from about 0.5 mg/mL to about 5 mg/mL.

In one embodiment, the stem-cell derived or immortalized human hepatic progenitors or cells as described above are transferred to a culture medium comprising GelMa at a concentration of about 5% (w/v), i.e., at a concentration of about 50 mg/mL; and further comprising a photoinitiator as described above, such as lithium phenyl-2,4,6-trimethylbenzoylphosphinate (also known as LAP or BioKey), at a concentration of about 0.1% (w/v) or about 0.3% (w/v), i.e., at a concentration of about 1 mg/mL or about 3 mg/mL.

In one embodiment, the stem-cell derived or immortalized human hepatic progenitors or cells as described above are transferred to a culture medium comprising GelMa as described above at a concentration of at least about $10^4$, $5 \cdot 10^4$, or $10^5$ cells/mL of culture medium comprising GelMa. In one embodiment, the stem-cell derived or immortalized human hepatic progenitors or cells as described above are transferred to a culture medium comprising GelMa as described above at a concentration of at most about $10^8$, $5 \times 10^7$ or $10^7$ cells/mL of culture medium comprising GelMa.

In one embodiment, the stem-cell derived or immortalized human hepatic progenitors or cells as described above are transferred to a culture medium comprising GelMa as described above at a concentration ranging from about $10^4$ cells/mL to about $10^8$ cells/mL, preferably from about $5 \cdot 10^5$ cells/mL to about $10^7$ cells/mL, more preferably from about $10^5$ to about $5 \times 10^6$ cells/mL, even more preferably from about $5 \times 10^5$ to about $2 \times 10^6$ cells/mL of culture medium comprising GelMa.

In one embodiment, the stem-cell derived or immortalized human hepatic progenitors or cells as described above are transferred to a culture medium comprising GelMa as described above at a concentration of about $5 \times 10^5$, $6 \times 10^5$, $7 \times 10^5$, $8 \times 10^5$, $9 \times 10^5$, $10^6$ or $2 \times 10^6$ cells/mL of culture medium comprising GelMa. In one embodiment, the stem-cell derived or immortalized human hepatic progenitors or cells as described above are transferred to a culture medium comprising GelMa as described above at a concentration of about $2 \times 10^6$ cells/mL of culture medium comprising GelMa.

In one embodiment, after transfer of the stem-cell derived or immortalized human hepatic progenitors or cells to a culture medium comprising GelMa as described above, the pH of the resulting mix is adjusted at a value ranging from about 7 to about 8, preferably at a value of about 7.4. Methods to adjust the pH of a culture medium are well-known to the person skilled in the art. For example, the pH of a culture medium may be increased as required with the addition of an appropriate volume of a NaOH solution. Alternatively, the pH of a culture medium may be lowered as required with the addition of an appropriate volume of a HCl solution.

Selecting conditions suitable for the culture of stem-cell derived or immortalized human hepatic progenitors or cells is well known to those skilled in the art. Thus, the culture conditions to be used according to the method of the invention, such as, for example, culture vessel, temperature, humidity and levels of $CO_2$, will be apparent to those having skill in the art and will depend on the stem-cell derived or immortalized human hepatic progenitors or cells to be cultured.

According to one embodiment, the mix resulting from the transfer of stem-cell derived or immortalized human hepatic progenitors or cells to a culture medium comprising GelMa as described hereinabove is poured into a culture vessel such as a plate or a multi-well plate, for example, a 24-well plate, a 48-well plate or a 96-well plate. It will be evident to those skilled in the art that the volume poured in the culture vessel will depend on the size of the culture vessel, for example on the size of the plate. In the case of a multi-well plate, the volume poured per well will depend on the size of the well and thus on the size of the multi-well plate.

Thus, in one embodiment, about 100 μL of the mix resulting from the transfer of stem-cell derived or immortalized human hepatic progenitors or cells to a culture medium comprising GelMa as described above are poured per well of a 96-well plate, about 300 μL are poured per well of a 48-well plate, and about 400 μL are poured per well of a 24-well plate.

According to one embodiment, the mix resulting from the transfer of stem-cell derived or immortalized human hepatic progenitors or cells to a culture medium comprising GelMa as described hereinabove is bioprinted. Thus, according to one embodiment, the mix resulting from the transfer of stem-cell derived or immortalized human hepatic progenitors or cells to a culture medium comprising GelMa is referred to as bioink and is used in a bioprinting process to produce a 3D bioprinted construct. Examples of bioprinting processes include for example extrusion bioprinting or microextrusion bioprinting, inkjet bioprinting, laser-assisted bioprinting and stereolithography.

In one embodiment, the bioink of the invention, that is to say the mix resulting from the transfer of stem-cell derived or immortalized human hepatic progenitors or cells to a culture medium comprising GelMa as described hereinabove, is bioprinted with extrusion bioprinting, microextrusion bioprinting, inkjet bioprinting, laser-assisted bioprinting or stereolithography. In one embodiment, the bioink of the invention is bioprinted with an extrusion printer (or bioprinter), a microextrusion printer (or bioprinter), an inkjet printer (or bioprinter), or a laser-assisted printer (or bioprinter).

In one embodiment, the bioink of the invention is bioprinted or extruded with an extrusion printer into a culture vessel such as a plate or a multi-well plate, for example, a 24-well plate, a 48-well plate or a 96-well plate. In one embodiment, the bioink of the invention is bioprinted with a microextrusion printer. In one embodiment, the bioink of the invention is bioprinted with an inkjet printer. In one embodiment, the bioink of the invention is bioprinted with a laser-assisted printer.

According to one embodiment, the mix resulting from the transfer of stem-cell derived or immortalized human hepatic progenitors or cells to a culture medium comprising GelMa as described above, in particular the 3D bioprinted construct of the invention, is illuminated with light having a wavelength ranging from about 250 nm to about 530 nm, preferably from about 365 to about 405 nm. In one embodiment, the mix resulting from the transfer of stem-cell derived or immortalized human hepatic progenitors or cells to a culture medium comprising GelMa as described above, in particular the 3D bioprinted construct of the invention, is illuminated with light having a wavelength of about 365 nm or 405 nm, preferably of 405 nm.

In one embodiment, the mix resulting from the transfer of stem-cell derived or immortalized human hepatic progenitors or cells to a culture medium comprising GelMa as described above, in particular the 3D bioprinted construct of the invention, is illuminated as described above for a time ranging from about 10 seconds to about 10 minutes, preferably from about 20 seconds to about 5 minutes, more preferably from about 30 seconds to about 2 minutes. In one embodiment, the mix resulting from the transfer of stem-cell derived or immortalized human hepatic progenitors or cells to a culture medium comprising GelMa as described above, in particular the 3D bioprinted construct of the invention, is illuminated as described above for about 30, 45, 60, 75, 90, 105 or 120 seconds, preferably for 60 seconds.

It is well-known in the field that the time of illumination will depend on the wavelength and on the intensity of the light. Accordingly, the intensity of the light will depend on the wavelength of the light and on the time of illumination. Examples of light intensity include intensities ranging from about 1 mW/cm$^2$ to about 150 mW/cm$^2$.

In one embodiment, the mix resulting from the transfer of stem-cell derived or immortalized human hepatic progenitors or cells to a culture medium comprising GelMa as described above, in particular the 3D bioprinted construct of the invention, is illuminated with a light intensity ranging about 1 mW/cm$^2$ to about 25 mW/cm$^2$, preferably from about 2 mW/cm$^2$ to about 15 mW/cm$^2$, more preferably from about 5 mW/cm$^2$ to about 10 mW/cm$^2$. In one embodiment, the mix resulting from the transfer of stem-cell derived or immortalized human hepatic progenitors or cells to a culture medium comprising GelMa as described above, in particular the 3D bioprinted construct of the invention, is illuminated with a light intensity of about 5, 6, 7, 8, 9, 10, 11, 12, 13, 14 or 15 mW/cm$^2$, preferably of about 7 mW/cm$^2$.

According to one embodiment of the method of the invention, after illumination, preferably with a light having a wavelength of about 365 nm or 405 nm, for a time ranging from about 30 seconds to about 2 minutes, preferably of about 60 seconds, the GelMa comprised in the culture medium as described above is polymerized and the stem-cell derived or immortalized human hepatic progenitors or cells are thus embedded in a GelMa matrix.

The method of the invention comprises a third step of culturing the stem-cell derived or immortalized human hepatic progenitors or cells embedded in the GelMa matrix as described above and thus allows to obtain 3D cell structures comprising human hepatic cells, in particular differentiated human hepatic cells.

According to the method of the invention, culture medium is added to the culture vessel comprising the GelMa matrix as described above. In other words, according to the method of the invention, the GelMa matrix as described above is covered with culture medium.

In one embodiment, culture medium is added to the culture vessel comprising the GelMa matrix as described above in a ratio ranging from about 3:1 culture medium: GelMa matrix to about 1:1.5 medium:GelMa matrix. In one embodiment, culture medium is added to the culture vessel comprising the GelMa matrix as described above in a ratio ranging from about 1.5:1 culture medium:GelMa matrix to about 1:1.5 culture medium:GelMa matrix. In one embodiment, culture medium is added to the culture vessel comprising the GelMa matrix as described hereinabove in a ratio culture medium:GelMa matrix of about 3:1, 2.9:1, 2.8:1, 2.7:1, 2.6:1, 2.5:1, 2.4:1, 2.3:1, 2.2:1, 2.1:1, 2:1, 1.9:1, 1.8:1, 1.7:1, 1.6:1, 1.5:1, 1.4:1, 1.3:1, 1.2:1, 1.1:1, 1:1, 1:1.1, 1:1.2, 1:1.3, 1:1.4, or 1:1.5, preferably in a ratio culture medium: GelMa matrix of about 1:1, 2:1 or 3:1. In one embodiment, culture medium is added to the culture vessel comprising the GelMa matrix as described hereinabove in a ratio culture medium:GelMa matrix of about 3:1.

In one embodiment, the culture medium added as described above and the culture medium used to obtain the GelMa matrix of the invention are different media. In another embodiment, the culture medium added as described hereinabove and the culture medium used to obtain the GelMa matrix of the invention are the same medium. Preferably, the same culture medium is used in the second step and in the third step of the method of the invention.

As mentioned hereinabove, the culture medium to be used according to the method of the invention will be apparent to those skilled in the art and will depend on the stem-cell derived or immortalized human hepatic progenitors or cells to be cultured. Culture media that may be used according to the method of the invention are described hereinabove.

In one embodiment, the culture medium added to the culture vessel comprising the GelMa matrix is a medium conducive to the culture of human hepatic cells, in particular differentiated human hepatic cells, such as human hepatocytes or hepatocyte-like cells. Examples of media conducive to the culture of human hepatic cells, in particular differentiated human hepatic cells, such as human hepatocytes or hepatocyte-like cells, are listed above. Thus, in one embodiment, the stem-cell derived or immortalized human hepatic progenitors or cells are embedded in the GelMa matrix according to the invention and are cultured in a medium conducive to the culture of human hepatic cells, in particular differentiated human hepatic cells, such as human hepatocytes or hepatocyte-like cells.

In one embodiment, the medium conducive to the culture of human hepatic cells is a medium supplemented with at least one of gentamicin, penicillin, streptomycin, insulin (preferably human insulin), L-glutamine, hydrocortisone (such as hydrocortisone hemisuccinate) or dexamethasone, and FCS (fetal calf serum) also referred to as FBS (fetal bovine serum).

In one embodiment, the medium conducive to the culture of human hepatic cells, in particular differentiated human hepatic cells, is a medium supplemented with penicillin, streptomycin, insulin (preferably human insulin), L-glutamine, and hydrocortisone (such as hydrocortisone hemisuccinate), and optionally with FCS (fetal calf serum) also referred to as FBS (fetal bovine serum).

In one embodiment, the medium conducive to the culture of human hepatic cells, in particular differentiated human hepatic cells, is William's E Medium supplemented with penicillin, streptomycin, insulin (preferably human insulin), L-glutamine, and hydrocortisone (such as hydrocortisone hemisuccinate), and optionally with FCS (fetal calf serum) also referred to as FBS (fetal bovine serum).

In one embodiment, the medium conducive to the culture of human hepatic cells, in particular differentiated human hepatic cells, is William's E Medium supplemented with penicillin, streptomycin, insulin (preferably human insulin), L-glutamine, hydrocortisone (such as hydrocortisone hemisuccinate) and with FCS (fetal calf serum) also referred to as FBS (fetal bovine serum).

In one embodiment, the medium conducive to the culture of human hepatic cells, in particular differentiated human hepatic cells, is a medium, preferably William's E Medium, supplemented with penicillin at a concentration ranging from about 50 to about 200 U/mL, preferably about 100 U/mL; streptomycin at a concentration ranging from about 1 to about 200 µg/mL, preferably 5 µg/mL; insulin, preferably human insulin, at a concentration ranging from about 1 to about 30 µg/mL, preferably about 5 µg/mL; glutamine (L-glutamine) at a concentration ranging from about 1 to about 10 mM, preferably about 2 mM; and hydrocortisone (such as hydrocortisone hemisuccinate) at a concentration ranging from about 0.1 to about 100 µM, preferably about 50 µM; and optionally FCS (fetal calf serum) at a concentration ranging from about 0 to about 20% (v/v), and preferably about 10% (v/v).

Selecting conditions suitable for the culture of stem-cell derived or immortalized human hepatic progenitors or cells is well-known to those skilled in the art. Thus, the culture conditions to be used for culturing stem-cell derived or immortalized human hepatic progenitors or cells embedded in the GelMa matrix according to the method of the invention, such as, for example, medium renewal, temperature, humidity and levels of $CO_2$ will be apparent to those having skill in the art and will depend on the stem-cell derived or immortalized human hepatic progenitors or cells to be cultured.

In one embodiment, the culture medium added to the culture vessel comprising the GelMa matrix as described hereinabove is changed every 1, 2, 3, 4 or more days, preferably every 2 days. In one embodiment, the culture medium added to the culture vessel comprising the GelMa matrix as described hereinabove is changed every 24 h, 36 h, 48 h, 60 h, 72 h or more, preferably every 48 h. The frequency at which to change the culture medium will be apparent to those skilled in the art and will depend on the purpose of the culture.

In one embodiment, the stem-cell derived or immortalized human hepatic progenitors or cells as described above embedded in the GelMa matrix according to the method of the invention are cultured at about 37° C. and about 5% $CO_2$, humidity 80-100%, preferably 85-95%, more preferably 95%.

In one embodiment, the stem-cell derived or immortalized human hepatic progenitors or cells embedded in the GelMa matrix according to the method of the invention are cultured for at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, or 35 days, preferably for at least 5 days, more preferably for at least 7 days. In one embodiment, the stem-cell derived or immortalized human hepatic progenitors or cells embedded in the GelMa matrix according to the method of the invention are cultured for at least about 1, 2, 3, 4, 5, or 6 weeks.

According to the present invention, the 3D cell structures obtained with the method as described above comprise or consist of human hepatic cells. In a particular embodiment, the 3D cell structures obtained with the method as described above comprise or consist of differentiated human hepatic cells. In a particular embodiment, the 3D cell structures obtained with the method as described above comprise or consist of human hepatocytes or hepatocyte-like cells.

As commonly known in the field, hepatocyte differentiation may be assessed for example through the measure of the expression of liver-specific genes, the measure of liver-specific markers, the measure of cell polarization and/or the measure of drug metabolism activities involved in the regulation of detoxifying pathways. For example, hepatocyte differentiation may be assessed by measuring the differential expression of liver-specific genes or of liver-specific markers between hepatocytes and non-liver cells used as a control. Further examples of methods for assessing hepatocyte differentiation are described hereinafter.

In one embodiment, the 3D cell structures obtained with the method as described above comprise or consist of differentiated HepaRG cells, said differentiated HepaRG cells comprising at least 90%, preferably at least 95%, of hepatocytes or hepatocyte-like cells. In one embodiment, the 3D cell structures obtained with the method as described above comprise or consist of differentiated HepaRG cells, said differentiated HepaRG cells being hepatocytes or hepatocyte-like cells.

According to one embodiment, the present invention relates to a method of culturing stem-cell derived or immortalized human hepatic progenitors or cells to obtain 3D cell structures comprising human hepatic cells, in particular differentiated human hepatic cells, said method comprising:

a) culturing the stem-cell derived or immortalized human hepatic progenitors or cells in a low or ultra-low attachment culture vessel, preferably in a low or ultra-low attachment plate;

b) transferring the stem-cell derived or immortalized human hepatic progenitors or cells to a culture medium comprising methacrylated gelatin (GelMa) at a concentration ranging from about 2% (w/v) to about 10% (w/v), preferably from about 2.5% (w/v) to about 7.5% (w/v), more preferably from about 2.5% (w/v) to about 5% (w/v), thereby embedding the stem-cell derived or immortalized human hepatic progenitors or cells in a GelMa matrix; and c) covering the GelMa matrix with culture medium and culturing the stem-cell derived or immortalized human hepatic progenitors or cells embedded in the GelMa matrix;

thereby obtaining 3D cell structures comprising human hepatic cells, in particular differentiated human hepatic cells.

In one embodiment, the present invention relates to a method of culturing stem-cell derived or immortalized human hepatic progenitors or cells to obtain 3D cell structures comprising human hepatic cells, in particular differentiated human hepatic cells, said method comprising:

a) culturing the stem-cell derived or immortalized human hepatic progenitors or cells in a low or ultra-low attachment culture vessel, preferably in a low or ultra-low attachment plate;

b) transferring the stem-cell derived or immortalized human hepatic progenitors or cells to a culture medium comprising methacrylated gelatin (GelMa) at a concentration ranging from about 2% (w/v) to about 10% (w/v), preferably from about 2.5% (w/v) to about 7.5% (w/v), more preferably from about 2.5% (w/v) to about 5% (w/v) and a photoinitiator, thereby embedding the stem-cell derived or immortalized human hepatic progenitors or cells in a GelMa matrix; and c) covering the GelMa matrix with culture medium and culturing the stem-cell derived or immortalized human hepatic progenitors or cells embedded in the GelMa matrix;

wherein the culture medium is supplemented with at least one of gentamicin, penicillin, streptomycin, insulin (preferably human insulin), L-glutamine, hydrocortisone (such as hydrocortisone hemisuccinate) or dexamethasone, and FCS (fetal calf serum) also referred to as FBS (fetal bovine serum);

thereby obtaining 3D cell structures comprising human hepatic cells, in particular differentiated human hepatic cells.

In one embodiment, the present invention relates to a method of culturing stem-cell derived or immortalized human hepatic progenitors to obtain 3D cell structures comprising differentiated human hepatic cells, said method comprising:

a) culturing the stem-cell derived or immortalized human hepatic progenitors in a low or ultra-low attachment culture vessel, preferably in a low or ultra-low attachment plate, preferably for a period of time ranging from about 12 h to about 24 h;

b) transferring the stem-cell derived or immortalized human hepatic progenitors to a culture medium comprising methacrylated gelatin (GelMa) at a concentration ranging from about 2% (w/v) to about 10% (w/v), preferably from about 2.5% (w/v) to about 7.5% (w/v), more preferably from about 2.5% (w/v) to about 5% (w/v), and a photoinitiator, preferably at a concentration ranging from about 0.05% (w/v) to about 0.5% (w/v), more preferably at a concentration ranging from about 0.1% (w/v) to about 0.3% (w/v), thereby embedding the stem-cell derived or immortalized human hepatic progenitors in a GelMa matrix; and c) covering the GelMa matrix with culture medium and culturing the stem-cell derived or immortalized human hepatic progenitors embedded in the GelMa matrix, preferably for at least 7 days;

thereby obtaining 3D cell structures comprising differentiated human hepatic cells.

In one embodiment, the present invention relates to a method of culturing undifferentiated HepaRG cells (i.e., HepaRG progenitors) to obtain 3D cell structures, preferably spheroids, comprising human hepatocytes or hepatocyte-like cells, said method comprising:

a) culturing the undifferentiated HepaRG cells (i.e., HepaRG progenitors) in a low or ultra-low attachment culture vessel, preferably in a low or ultra-low attachment plate, preferably for a period of time ranging from about 12 h to about 24 h;

b) transferring the undifferentiated HepaRG cells (i.e., HepaRG progenitors) to a culture medium comprising methacrylated gelatin (GelMa) at a concentration ranging from about 2% (w/v) to about 10% (w/v), preferably from about 2.5% (w/v) to about 7.5% (w/v), more preferably from about 2.5% (w/v) to about 5% (w/v), and a photoinitiator, preferably at a concentration ranging from about 0.05% (w/v) to about 0.5% (w/v), more preferably at a concentration ranging from about 0.1% (w/v) to about 0.3% (w/v), thereby embedding the undifferentiated HepaRG cells (i.e., HepaRG progenitors) in a GelMa matrix; and c) covering the GelMa matrix with culture medium and culturing the undifferentiated HepaRG cells (i.e., HepaRG progenitors) embedded in the GelMa matrix, preferably for at least 7 days;

wherein the culture medium is supplemented with at least one of gentamicin, penicillin, streptomycin, insulin (preferably human insulin), L-glutamine, hydrocortisone (such as hydrocortisone hemisuccinate) or dexamethasone, and FCS (fetal calf serum) also referred to as FBS (fetal bovine serum);

thereby obtaining 3D cell structures, preferably spheroids, comprising human hepatocytes or hepatocyte-like cells.

According to one embodiment, the 3D cell structures comprising human hepatic cells obtained according to the method of the invention are embedded in the GelMa matrix as described above.

In one embodiment, the method of the invention further comprises a step to isolate the 3D cell structures comprising human hepatic cells from the GelMa matrix.

In one embodiment, the 3D cell structures comprising human hepatic are isolated from the GelMa matrix after enzymatic digestion of the methacrylated gelatin. In one embodiment, the 3D cell structures comprising human hepatic are isolated from the GelMa matrix after incubation with a collagenase or an enzyme mixture with collagenolytic activity.

In one embodiment, the method of the invention further comprises a final step (e.g., step d)) of incubating the 3D cell structures comprising human hepatic embedded in the GelMa matrix with a collagenase or an enzyme mixture with collagenolytic activity. Examples of enzyme mixtures with collagenolytic activity include, without being limited to, Liberase® and Accutase®.

The present invention thus relates to a method of culturing stem-cell derived or immortalized human hepatic progenitors or cells to obtain 3D cell structures comprising human hepatic cells, said method comprising:

a) culturing the stem-cell derived or immortalized human hepatic progenitors or cells in a non-adherent culture vessel, preferably a low or ultra-low attachment culture vessel;

b) transferring the stem-cell derived or immortalized human hepatic progenitors or cells to a culture medium comprising methacrylated gelatin (GelMa), thereby embedding the stem-cell derived or immortalized human hepatic progenitors or cells in a GelMa matrix; and c) covering the GelMa matrix with culture medium and culturing the stem-cell derived or immortalized human hepatic progenitors or cells embedded in the GelMa matrix, thereby obtaining 3D cell structures comprising human hepatic cells; and d) optionally incubating the 3D cell structures comprising human hepatic cells embedded in the GelMa matrix with a collagenase or an enzyme mixture with collagenolytic activity, thereby isolating the 3D cell structures comprising human hepatic cells from the GelMa matrix.

In one embodiment, the present invention relates to a method of culturing stem-cell derived or immortalized human hepatic progenitors or cells to obtain 3D cell structures comprising human hepatic cells, said method comprising:

a) culturing the stem-cell derived or immortalized human hepatic progenitors or cells in a low or ultra-low attachment culture vessel, preferably in a low or ultra-low attachment plate;

b) transferring the stem-cell derived or immortalized human hepatic progenitors or cells to a culture medium comprising methacrylated gelatin (GelMa) at a concentration ranging from about 2% (w/v) to about 10% (w/v), preferably from about 2.5% (w/v) to about 7.5% (w/v), more preferably from about 2.5% (w/v) to about 5% (w/v), thereby embedding the stem-cell derived or immortalized human hepatic progenitors or cells in a GelMa matrix; and c) covering the GelMa matrix with culture medium and culturing the stem-cell derived or immortalized human hepatic progenitors or cells embedded in the GelMa matrix, thereby obtaining 3D cell structures comprising human hepatic cells; and d) optionally incubating the 3D cell structures comprising human hepatic cells embedded in the GelMa matrix with a collagenase or an enzyme mixture with collagenolytic activity, thereby isolating the 3D cell structures comprising human hepatic cells from the GelMa matrix.

In one embodiment, the present invention relates to a method of culturing stem-cell derived or immortalized human hepatic progenitors, preferably undifferentiated HepaRG cells (i.e., HepaRG progenitors), to obtain 3D cell structures comprising differentiated human hepatic cells, said method comprising:

a) culturing the stem-cell derived or immortalized human hepatic progenitors in a low or ultra-low attachment culture vessel, preferably in a low or ultra-low attachment plate, preferably for a period of time ranging from about 12 h to about 24 h;

b) transferring the stem-cell derived or immortalized human hepatic progenitors or cells to a culture medium comprising methacrylated gelatin (GelMa) at a concentration ranging from about 2% (w/v) to about 10% (w/v), preferably from about 2.5% (w/v) to about 7.5% (w/v), more preferably from about 2.5% (w/v) to about 5% (w/v), and a photoinitiator, preferably at a concentration ranging from about 0.05% (w/v) to about 0.5% (w/v), more preferably at a concentration ranging from about 0.1% (w/v) to about 0.3% (w/v), thereby embedding the stem-cell derived or immortalized human hepatic progenitors in a GelMa matrix; and c) covering the GelMa matrix with culture medium and culturing the stem-cell derived or immortalized human hepatic progenitors embedded in the GelMa matrix, preferably for at least 7 days, thereby obtaining 3D cell structures comprising differentiated human hepatic cells, preferably human hepatocytes or hepatocyte-like cells; and d) optionally incubating the 3D cell structures comprising differentiated human hepatic cells, preferably human hepatocytes or hepatocyte-like cells, embedded in the GelMa matrix with a collagenase or an enzyme mixture with collagenolytic activity, thereby isolating the 3D cell structures comprising differentiated human hepatic cells, preferably human hepatocytes or hepatocyte-like cells, from the GelMa matrix.

Another object of the invention is a 3D cell structure comprising human hepatic cells, preferably differentiated human hepatic cells. According to one embodiment, the 3D cell structure is a spheroid.

In one embodiment, the 3D cell structure of the invention, preferably a spheroid, comprises or consists of differentiated human hepatic cells. In one embodiment, the 3D cell structure of the invention, preferably a spheroid, comprises or consists of human hepatocytes or hepatocyte-like cells. In one embodiment, at least 90%, preferably at least 95%, of the cells of the 3D cell structure of the invention, preferably a spheroid, are human hepatocytes or hepatocyte-like cells.

In one embodiment, the 3D cell structure of the invention, preferably a spheroid, comprises or consists of a number of hepatocytes or hepatocyte-like cells ranging from about 10 to about 200, preferably from about 10 to about 100, more preferably from about 10 to about 50.

In one embodiment, a spheroid as meant herein, comprising or consisting of human hepatocytes or hepatocyte-like cells, is defined as a polarized structure with multiple bile canaliculi (or biliary canaliculi) which are 0.5- to 2-μm wide tissue space formed by the apical membranes of adjacent hepatocytes or hepatocyte-like cells.

In one embodiment, as meant herein, a polarized spheroid is defined as a spheroid with multiple bile canaliculi comprising or consisting of polarized hepatocytes or hepatocyte-like cells.

Hepatocytes are polarized cells which have basal/sinusoidal domains facing liver sinusoidal endothelial cells; lateral domains; and one or more apical/canalicular domains that can contribute to several bile canaliculi jointly with the directly opposing hepatocytes. Thus, in one embodiment, a polarized spheroid is defined as a spheroid with multiple bile canaliculi comprising or consisting of polarized hepatocytes or hepatocyte-like cells with basal/sinusoidal domains, lateral domains, and one or more apical/canalicular domains.

As commonly known in the field, hepatocyte polarization may be assessed for example through the detection and intracellular localization of specific markers. In particular, hepatocyte polarization may be assessed through the detection and intracellular localization of E-cadherin and/or N-cadherin (E-cadherin localizes specifically at the apical and lateral membranes in polarized hepatocytes). Thus, in one embodiment, a polarized spheroid is defined as a spheroid with multiple bile canaliculi comprising or consisting of hepatocytes or hepatocyte-like cells which are polarized, as evidenced by the localization of specific proteins at the apical and lateral membranes.

Hepatocyte polarization may also be assessed through the detection and intracellular localization of the transporter MRP2 (which is located exclusively at apical/canalicular domains in polarized hepatocytes). In one embodiment, a polarized spheroid is defined as a spheroid with multiple bile canaliculi comprising or consisting of polarized hepatocytes or hepatocyte-like cells, with hepatobiliary excretion occurring exclusively at apical/canalicular domains (thus confirming the expected polarization of the hepatocytes or hepatocyte-like cells in the spheroid).

In one embodiment, the spheroid of the invention has a size ranging from about 100 to about 150 μm. In one embodiment, the spheroid of the invention has a size ranging from about 10 to about 150 μm, preferably from about 20 to about 120 μm, more preferably from about 30 to about 100 μm. In one embodiment, by "size" of the spheroid it is meant "diameter" of the spheroid.

In one embodiment, the spheroid of the invention comprises or consists of a number of hepatocytes or hepatocyte-like cells ranging from about 10 to about 100, preferably from about 10 to about 50 and has a size ranging from about 20 to about 120 μm, preferably from about 30 to about 100 μm.

Surprisingly, the Applicants did not observe hypoxia or mortality (in particular necrosis) of the hepatocytes comprised within the spheroid of the invention. Strikingly, the Applicants did not observe hypoxia or mortality (in particular necrosis) of the hepatocytes comprised at the center of the spheroid of the invention.

In one embodiment, the 3D cell structure, preferably a spheroid as described above, comprises hepatocytes or hepatocyte-like cells which acquire or retain a differentiated state throughout the time of their culture in the GelMa matrix as described hereinabove. In one embodiment, the 3D cell structure, preferably a spheroid as described above, comprises hepatocytes or hepatocyte-like cells derived from undifferentiated HepaRG cells (i.e., HepaRG progenitors) which acquire a differentiated state throughout the time of their culture in the GelMa matrix as described hereinabove. In one embodiment, the 3D cell structure, preferably a spheroid as described above, comprises hepatocytes or hepatocyte-like cells which acquire or retain a differentiated state and retain the ability to proliferate throughout the time of their culture in the GelMa matrix as described hereinabove. In one embodiment, the 3D cell structure, preferably a spheroid as described above, comprises hepatocytes or hepatocyte-like cells derived from undifferentiated HepaRG cells (i.e., HepaRG progenitors) which acquire a differentiated state and retain the ability to proliferate throughout the time of their culture in the GelMa matrix as described hereinabove.

Methods to assess the differentiated state of hepatocytes or hepatocyte-like cells include, without being limited to, detection and intracellular localization of epithelial markers such as E-cadherin, cytokeratin 8, and cytokeratin 18; and detection and intracellular localization of mesenchymal markers such as N-cadherin, vimentin, cytokeratin 7, and cytokeratin 19.

As mentioned hereabove, hepatocytes carry out hepatic functions and hepatocyte-like cells recapitulate many, if not all, of the hepatic functions characterizing hepatocytes. As used herein, "hepatic functions" encompass the polarization, protein expression, protein secretion, and enzymatic activities specific to hepatocytes. Thus, hepatic functions may be assessed for example though the determination of the expression of albumin, aldolase B, alpha-1 antitrypsin encoded by the gene SERPINA1, and/or hepatocyte nuclear factor 4 alpha (HNF4A); the determination of the secretion of albumin; the determination of the expression, intracellular localization and/or activity of xenobiotic metabolism enzymes such as phase I, phase II, and/or phase III enzymes; the determination of the expression, intracellular localization and/or activity of drug transporters such as MRP2 and/or MRP3.

In one embodiment, the 3D cell structure of the invention, preferably a spheroid as described above, comprises hepatocytes or hepatocyte-like cells, which can be further characterized as being at least one of the following:
polarized hepatocytes or hepatocyte-like cells;
hepatocytes or hepatocyte-like cells expressing albumin, aldolase B, alpha-1 antitrypsin encoded by the gene SERPINA1, and/or hepatocyte nuclear factor 4 alpha (HNF4A); preferably albumin, and/or aldolase B;
hepatocytes or hepatocyte-like cells secreting albumin;
hepatocytes or hepatocyte-like cells expressing phase I, phase II, and/or phase III metabolism enzymes; and/or
hepatocytes or hepatocyte-like cells expressing drug transporters such as MRP2 and/or MRP3.

In one embodiment, the 3D cell structure of the invention, preferably a spheroid as described above, comprises polarized hepatocytes or hepatocyte-like cells. In one embodiment, the 3D cell structure of the invention, preferably a spheroid as described above, comprises hepatocytes or hepatocyte-like cells expressing albumin, aldolase B, alpha-1 antitrypsin encoded by the gene SERPINA1, and/or hepatocyte nuclear factor 4 alpha (HNF4A). In one embodiment, the 3D cell structure of the invention, preferably a spheroid as described above, comprises hepatocytes or hepatocyte-like cells secreting albumin. In one embodiment, the 3D cell structure of the invention, preferably a spheroid as described above, comprises hepatocytes or hepatocyte-like cells expressing phase I, phase II, and/or phase III metabolism enzymes. In one embodiment, the 3D cell structure of the invention, preferably a spheroid as described above, comprises hepatocytes or hepatocyte-like cells expressing drug transporters such as MRP2 and/or MRP3.

In one embodiment, the 3D cell structure of the invention, preferably a spheroid as described above, is embedded in a GelMa matrix. Thus, an object of the invention is a spheroid embedded in a GelMa matrix comprising hepatocytes or hepatocyte-like cells, said spheroid being defined as a polarized structure with multiple biliary canaliculi (or bile canaliculi). In one embodiment, the spheroid of the invention embedded in a GelMa matrix has a size ranging from about 100 to about 150 μm. In one embodiment, the spheroid of the invention embedded in a GelMa matrix has a size ranging from about 10 to about 150 μm, preferably from about 20 to about 120 μm, more preferably from about 30 to about 100 μm. In one embodiment, the spheroid of the invention embedded in a GelMa matrix comprises a number of hepatocytes or hepatocyte-like cells ranging from about 10 to about 200, preferably from about 10 to about 100, more preferably from about 10 to about 50. In one embodiment, the spheroid of the invention embedded in a GelMa matrix comprises a number of hepatocytes or hepatocyte-like cells ranging from about 10 to about 100, preferably from about 10 to about 50, and has a size ranging from about 20 to about 120 μm, more preferably from about 30 to about 100 μm.

In another embodiment, the 3D cell structure of the invention, preferably a spheroid as described above, is not embedded in a GelMa matrix. In other words, in one embodiment, the 3D cell structure of the invention, preferably a spheroid as described above, is an isolated 3D cell structure. Thus, an object of the invention is an isolated spheroid comprising hepatocytes or hepatocyte-like cells, said spheroid being defined as a polarized structure with multiple biliary canaliculi (or bile canaliculi). In one embodiment, the isolated spheroid of the invention has a size ranging from about 100 to about 150 μm. In one embodiment, the isolated spheroid of the invention has a size ranging from about 10 to about 150 μm, preferably from about 20 to about 120 μm, more preferably from about 30 to about 100 μm. In one embodiment, the isolated spheroid of the invention comprises a number of hepatocytes or hepatocyte-like cells ranging from about 10 to about 200, preferably from about 10 to about 100, more preferably from about 10 to about 50. In one embodiment, the isolated spheroid of the invention comprises a number of hepatocytes or hepatocyte-like cells ranging from about 10 to about 100, preferably from about 10 to about 50, and has a size ranging from about 20 to about 120 μm, more preferably from about 30 to about 100 μm.

In one embodiment, the 3D cell structure of the invention, preferably a spheroid as described above, is obtained or susceptible to be obtained according to the method as described above. Thus, in one embodiment, the 3D cell structure of the invention, preferably a spheroid as described above, is obtained or susceptible to be obtained according to the method comprising:

a) culturing stem-cell derived or immortalized human hepatic progenitors or cells in a non-adherent culture vessel, preferably a low or ultra-low attachment culture vessel;

b) transferring the stem-cell derived or immortalized human hepatic progenitors or cells to a culture medium comprising methacrylated gelatin (GelMa), thereby embedding the stem-cell derived or immortalized human hepatic progenitors or cells in a GelMa matrix; and c) covering the GelMa matrix with culture medium and culturing the stem-cell derived or immortalized human hepatic progenitors or cells embedded in the GelMa matrix, thereby obtaining 3D cell structures comprising human hepatic cells, in particular differentiated human hepatic cells; and d) optionally incubating the 3D cell structures comprising human hepatic cells, in particular differentiated human hepatic cells, embedded in the GelMa matrix with a collagenase or an enzyme mixture with collagenolytic activity, thereby isolating the 3D cell structures comprising human hepatic cells, in particular differentiated human hepatic cells, from the GelMa matrix.

Another object of the invention is the use of a 3D cell structure of the invention, preferably a spheroid as described above, comprising human hepatic cells for engineering an artificial liver model or an artificial liver organ.

In one embodiment, the 3D cell structure of the invention, preferably a spheroid as described above, comprising human hepatic cells is used for engineering an artificial liver model adapted to the study of physiopathological mechanisms. In one embodiment, the 3D cell structure of the invention, preferably a spheroid as described above, comprising human hepatic cells is used for engineering an artificial model of liver fibrosis. In one embodiment, the 3D cell structure of the invention, preferably a spheroid as described above, comprising human hepatic cells is used for engineering an artificial model of liver steatosis. In one embodiment, the 3D cell structure of the invention, preferably a spheroid as described above, comprising human hepatic cells is used for engineering an artificial model of liver-related disease.

Another object of the invention is the use of a 3D cell structure of the invention, preferably a spheroid as described above, comprising human hepatic cells for assessing in vitro the metabolism, toxicity and/or therapeutic effects of a compound. Examples of parameters that may be examined to assess the metabolism, toxicity and/or therapeutic effects of a compound include, without being limited to, cell morphology and motility, matrix reorganization and collagen synthesis, cell death, cell proliferation, cell metabolism, cell polarity, and cell differentiation.

In one embodiment, the compound is a xenobiotic. In one embodiment, the compound is a drug. As used herein, "drug" refers to a compound having or susceptible to have a biological effect.

Example of methods to assess the morphology and motility of human hepatic cells, in particular hepatocytes or hepatocyte-like cells, include, without being limited to, contrast light microscopy, confocal microscopy, auto-fluorescence imaging by biphoton microscopy imaging; time-lapse motility imaging, and invadosomes/pMLC, MLCK/RhoKinase immunolocalizations.

Examples of methods to assess matrix reorganization and collagen synthesis include, without being limited to, imaging of hepatocyte or hepatocyte-like cell spheroids with Second Harmonic Generation (SHG) microscopy.

Examples of methods to assess cell death include, without being limited to, imaging of nuclear fragmentation (such as the TUNEL assay), methods to assess apoptosis of human hepatic cells, in particular hepatocytes or hepatocyte-like cells, such as caspase imaging assays and caspase activity assays, and methods to assess necrosis of human hepatic cells, in particular hepatocytes or hepatocytes or hepatocyte-like cells, such as staining with YOYO.

Examples of methods to assess proliferation of human hepatic cells, in particular hepatocytes or hepatocyte-like cells, include, without being limited to, biphoton cells numeration from 3D z-stack images, determination of BrdU (bromodeoxyuridine) incorporation, determination of EdU (5-ethynyl-2'-deoxyuridine) incorporation, determination of a mitotic index, and immuno-histochemical staining or measurement of the expression of Ki67, β-tubulin, cyclin D1, cyclin D2, cyclin D3, cyclin E, cyclin A2, cyclin B, Cdk1, Cdk2 and/or Aurora A.

Examples of methods to assess the metabolism of a compound or to assess the hepatic functions of human hepatic cells, in particular hepatocytes or hepatocyte-like cells, include, without being limited to, assays to determine the enzymatic activities, protein and mRNA expression, regulation of phase I and phase II metabolism enzyme such as CYPs, GSTs, UGTs, NATs and associated nuclear factors CAR, PXR, AhR; MRP2 activity (related to cholestatic status) through fluorescein diacetate processing; and assays to determining lipid content such as oil red staining, or bodipy 493/503 labelling.

In one embodiment, the 3D cell structure of the invention, preferably a spheroid as described above, comprising human hepatic cells is used for assessing the liver genotoxicity of a compound as described above. Examples of parameters that may be examined to assess the liver genotoxicity of a compound as described above include, without being limited to, human hepatic cell proliferation, in particular hepatocyte or hepatocyte-like cell proliferation, DNA replication, chromosomes aberrations (such as, for example, single and double-strand breaks, loss, formation of micronuclei), presence of DNA damages, and presence of mutations.

Thus, for example, the liver genotoxicity of a compound as described above may be assessed through detection of micronuclei formation, comet assay, detection of phosphorylation of the histone H2Ax, and exome sequencing (for example to establish hotspot signatures linked to xenobiotic exposure) performed on a 3D cell structure of the invention, preferably a spheroid as described above, comprising human hepatic cells.

In one embodiment, the 3D cell structure of the invention, preferably a spheroid as described above, comprising human hepatic cells is used for assessing in vitro the therapeutic effects of a compound as described above in the treatment of a liver-related disease.

Another object of the invention is a method for engineering an artificial liver model or an artificial liver organ comprising human hepatic cells, the method comprising culturing stem cell-derived or immortalized human hepatic progenitors or cells as described above with at least another type of cells, wherein the stem cell-derived or immortalized human hepatic progenitors or cells embedded in the GelMa matrix are contacted with the at least another type of cells.

Thus, the present invention also relates to a method for engineering an artificial liver model or an artificial liver organ comprising human hepatic cells, the method comprising:

a) culturing stem cell-derived or immortalized human hepatic progenitors or cells in a non-adherent culture vessel, preferably a low or ultra-low attachment culture vessel;

b) transferring the stem cell-derived or immortalized human hepatic progenitors or cells to a culture medium comprising methacrylated gelatin (GelMa), thereby embedding the stem cell-derived or immortalized human hepatic progenitors or cells in a GelMa matrix; and c) covering the GelMa matrix with culture medium and culturing the stem cell-derived or immortalized human hepatic progenitors or cells embedded in the GelMa matrix; wherein said stem cell-derived or immortalized human hepatic progenitors or cells embedded in the GelMa matrix are contacted with at least another type of cells, thereby coculturing the stem cell-derived or immortalized human hepatic progenitors or cells embedded in the GelMa matrix with at least another type of cells;

thereby obtaining an artificial liver model or an artificial liver organ comprising human hepatic cells.

In one embodiment, the at least another type of cells is embedded in a matrix. In one embodiment, the at least another type of cells is embedded in a GelMa matrix. In one embodiment, the at least another type of cells is embedded in the GelMa matrix wherein the immortalized human hepatic progenitors or cells are embedded.

In one embodiment, the stem cell-derived or immortalized human hepatic progenitors or cells cultured as described above are bioprinted and the at least another type of cells is also bioprinted, thus producing a 3D bioprinted construct comprising both the stem cell-derived or immortalized human hepatic progenitors or cells and the at least another type of cells.

In one embodiment, the at least another type of cells is selected from the group comprising or consisting of human hepatic cells, human endothelial cells, human fibroblasts, immune cells. In one embodiment, the at least another type of cells is another type of human hepatic cell and the artificial liver model or an artificial liver organ thus comprises at least two types of human hepatic cells. Hepatic cells include, without being limited to, parenchymal liver cells (e.g., hepatocytes) and non-parenchymal liver cells (e.g., Kupffer cells, cholangiocytes, liver fibroblasts, sinusoidal endothelial cells and hepatic stellate cells).

In one embodiment, the stem cell-derived or immortalized human hepatic progenitors or cells are or give rise to human hepatocytes or hepatocyte-like cells and the other type of human hepatic cells are stellate cells.

In one embodiment, the stem cell-derived or immortalized human hepatic progenitors or cells, preferably undifferentiated HepaRG cells, are cocultured as described above with human hepatic stellate cells. In one embodiment, the stem cell-derived or immortalized human hepatic progenitors or cells, preferably undifferentiated HepaRG cells, are cocultured as described above with human hepatic stellate cells and with human endothelial cells.

Another object of the invention is an in vitro method of assessing the metabolism, toxicity and/or therapeutic effects of a compound, the method comprising:

a) obtaining 3D cell structures comprising human hepatic cells, in particular differentiated human hepatic cells, according to the method of the invention;

b) contacting the 3D cell structures comprising human hepatic cells, in particular differentiated human hepatic cells, with a compound; and c) assessing the metabolism, toxicity and/or therapeutic effects of the compound on the 3D cell structures comprising human hepatic cells, in particular differentiated human hepatic cells.

In one embodiment, the present invention relates to an in vitro method of assessing the metabolism, toxicity and/or therapeutic effects of a compound, the method comprising:

a) obtaining 3D cell structures, preferably spheroids as described above, comprising hepatocytes or hepatocyte-like cells according to the method of the invention;

b) contacting the 3D cell structures, preferably spheroids as described above, comprising hepatocytes or hepatocyte-like cells with a compound; and c) assessing the metabolism, toxicity and/or therapeutic effects of the compound on the 3D cell structures, preferably spheroids as described above, comprising hepatocytes or hepatocyte-like cells.

As mentioned hereinabove, the parameters that may be examined to assess the toxicity and/or the therapeutic effects of a compound on the 3D cell structures, in particular on the spheroids as described above, comprising human hepatic cells, preferably hepatocytes or hepatocyte-like cells, include, without being limited to, cell morphology and motility, matrix reorganization and collagen synthesis, cell death, cell proliferation, cell metabolism, cell polarity, and cell differentiation.

In one embodiment, the method of the invention is for assessing the liver genotoxicity of a compound. As mentioned hereinabove, the parameters that may be examined to assess the liver genotoxicity of a drug or a compound on the 3D cell structures, in particular on the spheroids as described above, comprising human hepatic cells, preferably hepatocytes or hepatocyte-like cells, include, without being limited to, cell proliferation, DNA replication, presence of chromosomes aberrations (such as, for example, single-strand breaks or double-strand breaks, loss, micronuclei formation), presence of DNA damages, and presence of mutations.

In one embodiment, the 3D cell structures, in particular the spheroids as described above, comprising human hepatic cells, preferably hepatocytes or hepatocyte-like cells, are contacted with a compound after at least 2, 3, 4, 5, 6, 7, 8, 9, 10, 11, 12, 13, 14, or 15 days of culture in the GelMa matrix. In another embodiment, the 3D cell structures, in particular the spheroids as described above, comprising human hepatic cells, preferably hepatocytes or hepatocyte-like cells, are contacted with a compound after at most 15, 14, 13, 12, 11, 10, 9, 8, 7, 6, 5, 4, 3, or 2 days of culture in the GelMa matrix.

In one embodiment, the compound is a xenobiotic. In one embodiment, the compound is a drug. As used herein, "drug" refers to a compound having or susceptible to have a biological effect.

The method of the invention for culturing stem cell-derived or immortalized human hepatic progenitors or cells allows to obtain 3D animal cell structures which acquire or retain a differentiated state and display a long-term viability.

As illustrated in the Examples below, the Applicants showed that the method of the invention is particularly suited for the culture of undifferentiated HepaRG cells (i.e., HepaRG progenitors), as it allows to obtain spheroids comprising human hepatocytes or hepatocyte-like cells without requiring an incubation of the undifferentiated HepaRG cells with DMSO and in a shorter time when compared to the established method of culture of undifferentiated HepaRG cells (Jossé et al., Drug Metab Dispos. 2008 June; 36(6): 1111-8).

Indeed, in 2D cultures in the absence of DMSO, proliferating HepaRG cells are undifferentiated. At confluence and in the presence of DMSO, after two weeks in 2D cultures, two lineages are obtained from undifferentiated HepaRG cells (i.e., HepaRG progenitors): some cells (hepatocytes or hepatocyte-like cells) acquire differentiated hepatocyte markers while other cells (cholangiocyte-like cells) express cellular markers characteristic of the bile duct cells.

With the method of the invention, differentiation of the HepaRG progenitors occurs rapidly in spheroids and only differentiation into hepatocytes or hepatocyte-like cells happens (no cholangiocyte-like cells). With the method of the invention, HepaRG progenitors do not require to be pre-differentiated in a 2D culture in presence of DMSO before 3D seeding. Therefore, with the method of the invention, HepaRG cells are always cultured in the absence of DMSO.

The spheroids obtained by culturing undifferentiated HepaRG cells according to the method of the invention are characterized by their polarized structure (polarized hepatocytes or hepatocyte-like cells with multiple biliary canaliculi (bile canaliculi)) and by their small size (usually from about 20 to about 120 $\mu$m, more often from about 30 to about 100 $\mu$m). Indeed, said spheroids comprise a limited number of human hepatic cells (usually from about 10 to about 100 cells, more often from about 10 to about 50 cells). Of interest, the undifferentiated HepaRG cells in culture according to the method of the invention acquire the differentiated state of human hepatocytes or hepatocyte-like cells and are able to carry out a number of hepatic functions, as shown in Example 1 below. Moreover, said human hepatocytes or hepatocyte-like cells are able to proliferate, as shown in Example 1 below. Of note, the spheroids obtained by culturing undifferentiated HepaRG cells according to the method of the invention do not display hypoxia or mortality (in particular necrosis) of the hepatocytes or hepatocyte-like cells comprised within the spheroids.

As illustrated in the Examples below, the method of the invention is also particularly suited for bioprinting, allowing the generation of precisely organized 3D cell structures that may comprise several types of human cells, and in particular several type of human hepatic cells. The method of the invention thus allows the establishment of complex multicellular hepatic models, as shown in Example 2 below.

EXAMPLES

The present invention is further illustrated by the following examples.

Example 1

Materials and Methods

Material

Cells

The following cell lines were used: HuH-7 cells and HepaRG cells. Both cell lines are immortalized human cells derived from a hepatocellular carcinoma.

Reagents

Lipofectamine RNAi max transfection reagent, William's E medium and TRIzol were obtained from Invitrogen (Invitrogen, Carlsbad, CA, USA). FBS and saccharose were obtained from Eurobio (Evry, France). Penicillin/Streptomycin and FBS HyClone III were obtained from Thermo Fisher (Waltham, MA USA). WST-1 reagent, geneticin, human insulin, hydrocortisone hemisuccinate, Dimethyl sulfoxide also known as DMSO (D4540), formaldehyde, gelatin, 5-ethylenyl-2'-deoxyuridine, salicylamide, CY5-azide, ethoxyresorufin and methyresorufin, 3-methylcholanthrene and rifampicin were obtained from Sigma-Aldrich (St. Louis, MO, USA). Methacrylated gelatin (GelMa) was synthetized by the ART Bio-encres (Bordeaux, FR). Lithium phenyl-2,4,6 trimethylbenzoylphosphinate (LAP) was obtained from TCI (Japan) and U0126 was obtained from Promega (Mannheim, GE). Phenobarbital was obtained from the Coopération pharmaceutique française. The Dapi Fluoromount-G was obtained from Southern Biotech (Birmingham, AL, USA).

Methods

Cell Culture

HuH-7 cells (n° 01042712, Health Protection Agency Culture Collections, Salisbury, UK) DNA transfections were carried out using Lipofectamine RNAi max transfection reagent according to the manufacturer's instructions. Briefly, cells were plated in a 35 mm-petri dish. 3 µl of EmGFP-geneticin vector and 5 µl of Lipofectamine RNAi max were mixed in 200 µl Opti-MEM® and then added to the cells. After overnight incubation, cells were incubated in DMEM medium for 24 h, then selected by treatment with geneticin at 10 mg/mL during 48 h. After selection, HuH-7 GFP+ cells were cultured in DMEM comprising 4.5 g/L of both glucose and pyruvate supplemented with 10% (v/v) fetal bovine serum (EuroBio), 100 units/mL penicillin and 100 µg/mL streptomycin, 2 mM L-glutamine and 500 µg/mL geneticin.

Undifferentiated HepaRG cells (Biopredic, Saint Grégoire, France) were cultured in William's E medium without L-Glutamine supplemented with 10% (v/v) fetal bovine serum Hyclone III, 100 units/mL penicillin, 100 µg/mL streptomycin, 5 µg/mL human insulin, 2 mM L-glutamine and $5×10^{-5}$ M hydrocortisone hemisuccinate (hereinafter referred to as supplemented William's E medium) for 14 days.

For control experiments in 2D culture (also referred to as 2D-DMSO), hepatic differentiation of HepaRG cells was induced in 2D culture by treatment with 2% (v/v) DMSO (D4540, Sigma-Aldrich, St. Louis, MO, USA) for an additional 14 days.

Culture According to the Method of the Invention

Culture in a low attachment plate: immortalized human cells HuH-7 or undifferentiated HepaRG were incubated at 37° C., 5% $CO_2$, 100% humidity during 15 h-24 h in 6-well low attachment plates (Corning®, Costar®) at a concentration of about $3×10^6$ cells per well, in William's E medium without L-Glutamine supplemented with 10% (v/v) fetal bovine serum Hyclone III, 100 units/mL penicillin, 100 µg/mL streptomycin, 5 µg/mL human insulin, 2 mM L-glutamine and $5×10^{-5}$ M hydrocortisone hemisuccinate.

Preparation of medium comprising GelMa: methacrylated gelatin was prepared as previously described (Kolesky et al., Adv Mater. 2014 May 21; 26(19):3124-30). Briefly, a 10% (w/v) gelatin solution (type A, 300 bloom from porcine skin, Sigma), in PBS, was warmed at 60° C. for 2 h under stirring. Then, the temperature was set to 50° C. and 0.14 mL of methacrylic anhydride (Sigma) per gram of gelatin was added dropwise. The solution was left to react for 4 h, under stirring, then diluted to 5% (w/v) in PBS. The reacted gelatin was precipitated using a 4-fold excess volume of cold acetone. The precipitated gelatin was recovered, vacuum dried for 30 minutes, and then redissolved at 10% (w/v) in PBS at 40° C. It was then placed inside a 12-14 kDa molecular weight cutoff (MWCO) dialysis tubing (Sigma), and dialyzed against deionized water for 3 days, with two daily water changes. The purified GelMa was frozen at –80° C., freeze dried, and stored at –20° C. Small crushed fragments of freeze-dried GelMa (up to 2 mm in length) were dissolved at 37° C. overnight or for a minimum of 6 h in the supplemented William's E medium comprising 10% (v/v) fetal bovine serum Hyclone III, 100 units/mL penicillin, 100 µg/mL streptomycin, 5 µg/mL human insulin, 2 mM L-glutamine and $5×10^{-5}$ M hydrocortisone hemisuccinate as described above. Unless indicated otherwise, a volume of lithium phenyl-2,4,6-trimethylbenzoylphosphinate (LAP) at a concentration of 10 mg/mL (in phosphate-buffer saline (PBS)) was then added to obtain a supplemented William's E medium comprising GelMa at a final concentration of 2.5 or 5 g/100 mL, i.e., a final concentration of 2.5 or 5% w/v, and LAP at a final concentration of 100 or 300 mg/100 mL, i.e., a final concentration of 0.1 or 0.3% w/v. Before use, the medium comprising 2.5 or 5% w/v GelMa and 0.1 or 0.3% w/v LAP was kept at 37° C., protected from light. For rheology analyses, photopolymerized GelMa matrices, at 2.5, 5, 7.5 or 10% (w/v) were soaked for 24 h in PBS and then loaded in a Kinexus pro+ rheometer (Malvern Instruments, UK). Frequency sweeps were performed at a constant strain (0.1%) in an angular frequency range of 0.1-100 rad/s, at 37° C.

Inclusion in a GelMa matrix followed by culture of hepatocytes embedded in the GelMa matrix: HuH-7 or undifferentiated HepaRG were transferred to a suitable container such as an Eppendorf tube (1.5 or 2 mL) or a Falcon tube (15 mL) and centrifuged at 200 g for 2 min. The supernatant was removed and medium comprising 2.5 or 5% w/v GelMa and 0.1 or 0.3% w/v LAP was added to obtain a concentration ranging from about $0.5×10^6$ to $2×10^6$ cells per mL of medium (for example $0.5×10^6$ HuH-7 or $2×10^6$ undifferentiated HepaRG cells). For the bioprinting process, 100 µL of the bio-ink, i.e., medium comprising 5% (w/v) GelMa, 0.1% (w/v) LAP and cells, were cooled at 15° C. and extruded through a 23 G or 25 G needle at 1.4-2.4 bar, at 480 mm/min, with the extrusion printer Allevi 2 (Allevi, Philadelphia, PA, USA) in a 48- or 96-well plate. The 3D construct was designed by the computer aided design software OnShape (Cambridge, MA, USA).

Polymerization (i.e., crosslinking) of the GelMa matrix was induced by illumination of the bioprinted 3D construct for 30 seconds to 10 min with a 365, 405 nm or 530 nm LED, preferably by illumination for 60 seconds with a 405 nm ultraviolet light (7 mW/cm²). After polymerization of the GelMa matrix, a volume of the same supplemented William's E medium (see above) equal to the volume of GelMa matrix was added so that the GelMa matrix was submerged in supplemented William's E medium. The cells embedded in the GelMa matrix were cultured in the supplemented William's E medium as described above for at least 2 days in an incubator at 37° C., 5% CO2, humidity 95%. The medium was changed every 48 h.

Hereafter, in Example 1, the term "GelMa culture" refers to a culture of immortalized hepatic cells established as described hereinabove, with a first incubation (or culture) of the cells in a low attachment plate followed by the inclusion of the cells in a GelMa matrix, according to the method of the invention. Unless indicated otherwise, any mention of a time of culture, e.g., day 5 of culture, refers to the time of culture in a GelMa (or in a standard multi-well plate for the 2D or 2D-DMSO control condition). Similarly, seeding refers to the inclusion of the cells in a GelMa matrix.

Cell Viability

Cell viability was assessed by using the WST-1 (water soluble tetrazolium-1) proliferation assay on cell laden 3D constructs at different days or times of culture. Briefly, the cell laden 3D constructs were treated with 100 µL of WST-1 reagent and incubated 30 min at 37° C. Absorbance at 440 nm was read in a microplate reader (SpectrostarNano, BMG labtech, Champigny s/Marne, FR) and the values were converted into percentage of absorbance by comparison with controls assessed at day 0 or time 0. Measurement of lactate dehydrogenase (LDH) was performed on supernatants with the LDH-Glo™ Cytotoxicity Assay (Promega) by following manufacturer's instructions.

Immunostaining

Cell laden 3D constructs were fixed in 4% formaldehyde, washed 3 times in PBS and stored at 4° C. until use or immediately suspended in a 0.12 M phosphate buffer containing 10% w/v saccharose and incubated overnight. They were embedded in a protective matrix composed of gelatin 7.5% w/v and 10% w/v saccharose, then frozen in isopentane and cryosectioned at a thickness of 7 μm. Slides were stained on the Discovery Automated IHC stainer using the discovery Rhodamin kit (Ventana Mediacl systems, Tucson, AZ, USA). The concentrations and references of the primary antibodies that were used can be found in Table 1 below. After rinsing, signal enhancement was performed using the Ventana Rhodamin kit and secondary antibody anti-rabbit HRP (760-4311, Roche) or secondary antibody anti-mouse HRP (760-4310, Roche) for 16 min of incubation. After removal from the instrument, slides were manually rinsed, stained when required with albumin antibody then a secondary antibody for albumin detection (Donkey anti goat 488), and mounted with Dapi Fluoromount-G.

kit (AssayGenie, Dublin, IR) according to the manufacturer's protocol, using medium as standard and reading the absorbance at 420 nm (SpectrostarNano, BMG labtech, Champigny s/Marne, FR)

CYP Activities Measurement by Fluorescence

After a 24-hour induction with DMSO 0.1% (v/v) or 3-methylcholanthrene (3-MC or 3MC) at 5 μM, ethoxyresorufin-O-deethylation (EROD) was used for measuring CYP1A activity and methyresorufin-O-deethylation (MROD) was used for measuring CYP1A2 activity. EROD and MROD assays were performed as described by Burke and Mayer (Burke & Mayer, Chem Biol Interact. 1983 Jul. 15; 45(2):243-58). Briefly, the cells were washed with PBS at 37° C. and salicylamide (1.5 mM) was added to block phase II conjugation enzymes. 7-ethoxyresorufine or 7-methoxyresorufine was then added 1 min later and the oxidation of the substrates was measured by fluorescence detection every 2 min during 20 min at 37° C. (SpectraMax GeminiXS, Molecular devices, San Jose, CA, USA). After the detection, a WST-1 proliferation assay was performed as describe above to normalize activity with the quantity of viable cells.

TABLE 1

| Primary antibodies | | | |
|---|---|---|---|
| Antibody target | Antibody reference | Antibody concentration | Antibody provider |
| Albumin | A80229A | 1:100 | Bethyl Laboratories, TX, USA |
| Cleaved caspase 3 | 9661S | 1:500 | Cell Signaling, Leiden, NL |
| E-Cadherin | 3195S | 1:100 | Cell Signaling, Leiden, NL |
| N-Cadherin | 610921 | 1:100 | BD Bioscience, San Jose, CA, USA |
| MRP2 | Ab3373 | 1:100 | Abcam, Paris, FR |
| Cyclin D1 | Ab16663 | 1:200 | Abcam, Paris, FR |
| Ki67 | HPA001164 | 1:400 | Atlas Antibodies, Bromma, SE |

Proliferation Quantification

For 5-ethynyl-2'-deoxyuridine (EdU) incorporation, cell laden 3D constructs were treated 48 h with EdU at 1 μM. For negative controls, cells were treated 24 h prior EdU treatment with U126 at 0.05 nM until the fixation of the 3D cell structures. 3D cell structures were fixed and cryosectioned as described above. EdU revelation was carried out by performing permeabilization using 0.1% (v/v) Triton X-100 for 10 min. Then, samples were treated with a mix of CuSO4 (1 μM), Tris pH 8.5 (0.1M), ascorbic acid (0.1M) and CY5-azide (1.5 μM) for 1 h. Cells were mounted with Dapi Fluoromount-G and the nucleus staining was monitored using a fluorescence microscope (Eclipse Ni-E, Nikon, Amsterdam, NL). Image processing was carried out using ImageJ software (http://imagej.nih.gov/ij/).

Metabolic Analysis

Medium samples were taken for the determination of albumin and urea content every 48 h. Secreted albumin and proCol1a1 (pro-collagen 1 alpha 1) were quantified using the human serum albumin Duoset Enzyme Linked Immunosorbent Assay (ELISA) kit (R&D systems, Minneapolis, MN, USA) and the human pro-Col1a1 Duoset Enzyme Linked Immunosorbent Assay kits (R&D systems, Minneapolis, MN, USA), according to manufacturer's instructions. Quantification was performed by measuring absorbance at 450 nm using a microplate reader (SpectrostarNano, BMG labtech, Champigny s/Marne, FR). Urea secretion in the medium was measured using a ChromaDazzle Urea Assay CYP Activities Measurement by Luminescence Cytochrome P450 oxidase 2B6 and 3A4 activities were assessed by treating cells with DMSO 0.1% v/v (control) or phenobarbital (0.2 mM, 72 h), and DMSO 0.1% v/v (control) or rifampicin (5 μM, 72 h), respectively. Using the P450 GloAssay (Promega) according to the manufacturer's instructions, a CYP specific luciferin substrate was added on cell laden 3D constructs and incubated at 37° C., 5% CO$_2$. After 1 hour, CYP-mediated conversion of luciferin substrate to luciferin was determined. The supernatant was incubated with luciferin detection reagent during 20 min at room temperature and the luminescence was measured. After the luminescence measurement, a WST-1 proliferation assay was performed as describe above to normalize activity with the quantity of viable cells.

RNA Extraction and Quantitative Real Time PCR

After 1, 2 and 4 week(s) of culture, 3D constructs comprising 3D cell structures were harvested, washed twice in PBS and total ribonucleic acid (RNA) was extracted using TRIzol™ reagent. The concentration of total RNA was measured with a NanoDrop ND-1000 (NanoDrop Technologies). Complementary deoxyribonucleic acid (cDNA) was synthetized using the High Capacity cDNA reverse transcriptase kit (Applied Biosystems Foster City, CA, USA), and real-time polymerase chain reaction (PCR) was performed using the Power SYBR Green PCR master mix (Applied Biosystems Foster City, CA, USA). Basic local alignment search tool (BLAST) was used to design primer sequences which were purchased from Eurogentec (Searing, BE). All used primers are listed in Table 2 below. The expression levels of the target genes were normalized to those of GAPDH and determined by the ΔΔCt method. Final results were expressed as the n-fold difference in target gene expression in samples when compared with the mean expression values of the target gene for controls: either non-differentiated HepaRG (referred to as 2D) or HepaRG differentiated in standard 2D culture conditions (referred to as 2D DMSO). All results are presented as mean±SD of at least n=3 experiments.

TABLE 2

| Primer sequences | |
| --- | --- |
| Target gene | Primer sequence |
| Albumin-forward | TGCTTGAATGTGCTGATGACAGG (SEQ ID NO: 1) |
| Albumin-reverse | AAGGCAAGTCAGCAGGCATCTCATC (SEQ ID NO: 2) |
| Aldolase B-forward | GTCCATCCAGCCTCGCTATC (SEQ ID NO: 3) |
| Aldolase B-reverse | ACCAGTCCATTCTGCTGACA (SEQ ID NO: 4) |
| CDH1-forward | CGGGAATGCAGTTGAGGAT (SEQ ID NO: 5) |
| CDH1-reverse | AGGATGGTGTAAGCGATGG (SEQ ID NO: 6) |
| CDH2-forward | GTGCATGAAGGACAGCCTCT (SEQ ID NO: 7) |
| CDH2-reverse | ATGCCATCTTCATCCACCTT (SEQ ID NO: 8) |
| CK19-forward | GAGCAGGTCCGAGGTTACTG (SEQ ID NO: 9) |
| CK19-reverse | GCTCACTATCAGCTCGCACA (SEQ ID NO: 10) |
| CYP 1A1-forward | GACATTGGCGTTCTCATCCA (SEQ ID NO: 11) |
| CYP 1A1-reverse | AGAAGCTATGGGTCAACCCA (SEQ ID NO: 12) |
| CYP 1A2-forward | TGGAGACCTTCCGACACTCCT (SEQ ID NO: 13) |
| CYP 1A2-reverse | CGTTGTGTCCCTTGTTGTGC (SEQ ID NO: 14) |
| CYP 2B6-forward | TTCCTACTGCTTCCGTCTATC AAA (SEQ ID NO: 15) |
| CYP 2B6-reverse | GTGCAGAATCCCACAGCTCA (SEQ ID NO: 16) |
| CYP 2C19-forward | GTGAAGGAAGCCCTGATTGA (SEQ ID NO: 17) |
| CYP 2C19-reverse | TCCTCTTGAACACGGTCCTC (SEQ ID NO: 18) |
| CYP 2C9-forward | GGACAGAGACGACAAGCACA (SEQ ID NO: 19) |
| CYP 2C9-reverse | AATGGACATGAACAACCCTCA (SEQ ID NO: 20) |

TABLE 2-continued

| Primer sequences | |
| --- | --- |
| Target gene | Primer sequence |
| CYP 2E1-forward | TTGAAGCCTCTCGTTGACCC (SEQ ID NO: 21) |
| CYP 2E1-reverse | CGTGGTGGGATACAGCCAA (SEQ ID NO: 22) |
| CYP 3A4-forward | CTTCATCCAATGGACTGCATA AAT (SEQ ID NO: 23) |
| CYP 3A4-reverse | TCCCAAGTATAACACTCTACA CA GACAA (SEQ ID NO: 24) |
| FXR-forward | GGAGGATCAAAGGGGATGA (SEQ ID NO: 25) |
| FXR-reverse | CAGTTGCCCCCGTTTTTAC (SEQ ID NO: 26) |
| GAPDH-forward | GTGGACCTGACCTGCCGTCT (SEQ ID NO: 27) |
| GAPDH-reverse | GGAGGAGTGGGTGTCGCTGT (SEQ ID NO: 28) |
| HNF4a-forward | AACCTGTTGCAGGAGATGCT (SEQ ID NO: 29) |
| HNF4a-reverse | TTGCCTTGTTCCCATTTTTC (SEQ ID NO: 30) |
| MRP2-forward | TGAGCAAGTTTGAAACGCACAT (SEQ ID NO: 31) |
| MRP2-reverse | AGCTCTTCTCCTGCCGTCTCT (SEQ ID NO: 32) |
| PXR-forward | CCAGGACATACACCCCTTTG (SEQ ID NO: 33) |
| PXR-reverse | CTACCTGTGATGCCGAACAA (SEQ ID NO: 34) |
| Serpina1-forward | CACCGTGAAGGTGCCTATGATG (SEQ ID NO: 35) |
| Serpina1-reverse | GGCATTGCCCAGGTATTTCATC (SEQ ID NO: 36) |
| SOX9-forward | GCCTTTTTGTCCATCCCTTT (SEQ ID NO: 37) |
| SOX9-reverse | GCTTGCATTGTTTTTGTGTCA (SEQ ID NO: 38) |
| Vimentin-forward | CCAAACTTTTCCTCCCTGAACC (SEQ ID NO: 39) |
| Vimentin-reverse | GTGATGCTGAGAAGTTTCGTTGA (SEQ ID NO: 40) |
| ACTA2-forward | TATTCCTTCGTTACTACTGCT (SEQ ID NO: 41) |
| ACTA2-reverse | AAGTCCAGAGCTACATAACA (SEQ ID NO: 42) |
| ADAMTS12-forward | CACGACGTGGCTGTCCTTCT (SEQ ID NO: 43) |
| ADAMTS12-reverse | CCGAATCTTCATTGATGTTACA ACTG (SEQ ID NO: 44) |

TABLE 2-continued

Primer sequences

| Target gene | Primer sequence |
|---|---|
| Col1A1-forward | CCTCAAGGGCTCCAACGAG (SEQ ID NO: 45) |
| Col1A1-reverse | TCAATCACTGTCTTGCCCCA (SEQ ID NO: 46) |
| Col3A1-forward | GGGGAGCTGGCTACTTCTCG (SEQ ID NO: 47) |
| Col3A1-reverse | TGAGGTCCTTGACCATTAGG (SEQ ID NO: 48) |
| LPL-forward | TCATTCCCGGAGTAGCAGAGT (SEQ ID NO: 49) |
| LPL-reverse | GGCCACAAGTTTTGGCACC (SEQ ID NO: 50) |
| MMP2-forward | CAAGGACCGGTTTATTTGGC (SEQ ID NO: 51) |
| MMP2-reverse | ATTCCCTGCGAAGAACACAGG (SEQ ID NO: 52) |
| TIMP1-forward | CACCCACAGACGGCCTTCT (SEQ ID NO: 53) |
| TIMP1-reverse | CTTCTGGTGTCCCCACGAACTT (SEQ ID NO: 54) |
| TGFβI-forward | CTTCGCCCCTAGCAACGAG (SEQ ID NO: 55) |
| TGFβI-reverse | TGAGGGTCATGCCGTGTTTC (SEQ ID NO: 56) |

Transcriptomic Analysis

Total RNAs were purified from freshly isolated human hepatocytes (PHH T0) (n=5), and from differentiated HepaRG after 14 days of culture on 2D (HRG 2D DMSO) (n=5) and at day 14 of culture on GelMa (HepaRG 3D GelMa) (n=4). The samples were concentrated using the RNA Clean & Concentrator-5 (Zymo, Irvine, CA, USA) and checked for RNA degradation based on the RNA Integrity Number (RIN>6). 3' sequencing RNA Profiling (3' SRP-seq) libraries were made at the GenoBIRD facility of Nantes, France, and sequenced using the HiSeq 2500 (Illumina, San Diego, CA, USA) following the described protocol (Soumillon et al., 2014, BioRxiv 003236). The analysis of the generated data was performed using R packages. The differentially expressed genes (FC>2, p<0.05) between HRG 2D DMSO and HRG GelMa D14 were functionally analyzed by computing enrichments for gene ontology (GO) terms, using the WEB-based database GEne SeT AnaLysis Toolkit (WebGestalT) restricted to protein coding data set. The presented data are selected as the top ten of the enriched categories, sorted by increasing enrichment ratios (FDR<0.05).

SHG/TPEF Microscopy

TPEF/SHG microscopy imaging was performed on mRIC facility of Biosit, University of Rennes1 (France). The SHG imaging system is composed of a confocal TCS SP5 scanning head (Leica Microsystems, Mannheim, Germany) mounted on a DMIRE2 inverted microscope (Leica Microsystems) and equipped with a MAITAI femtosecond laser (Spectra Physics, Santa Clara, CA). 60× water immersion objective (Olympus LUMFL 60 W×1.1NA) was used for applying an 820 nm excitation to the sample. The SHG signal was collected in the forward direction using the condenser (S1, NA ¼ 0.9-1.4; Leica Microsystems), and the TPEF was epi-collected in the backward direction. IRSP 715 bandpass and 410 nm infrared (IR) filters (10 nm full width at half-maximum, FWHM) were placed before the photomultiplier tube. The image processing was performed with ImageJ software (National Institutes of Health).

Statistical Analysis

All variables were expressed as means±standard deviations (SDs) of at least 3 experiments with 3 technical replicates. Evaluation of the difference between the mean values in each group was performed using t-test or one-way analysis of variance (ANOVA) (GraphPad Prism 6, GraphPad Software, Inc.; La Jolla, CA, USA), in which p values are considered to indicate significance for * or #$p \leq 0.05$;  or ##$p \leq 0.01$; *$p \leq 0.001$; ****$p \leq 0.0001$.

Results

Physical Properties of GelMa Matrix

The physical properties of different methacrylated gelatin matrices (GelMa matrices) were analyzed by assessing the polymerization and bioprinting properties of the matrices as a function of the GelMa concentration, the photoinitiator LAP concentration and the illumination time at 405 nm (FIG. 1). As shown on FIG. 1A, at 20° C. a concentration of GelMa of 2.5% was not sufficient to ensure a proper polymerization of the matrix and subsequently, an optimal viscosity for the bioprinting process. As shown on FIG. 1B, a minimum concentration of LAP (i.e., 0.1% (w/v)) and an optimized illumination time (i.e., 60 seconds) were defined to reduce the phototoxicity and the production of excess free radicals while maintaining sufficient structural integrity of the printed GelMa for 28 days at 37° C. As shown on FIGS. 1C-D, weight loss of the matrices was assessed as a function of the photoinitiator LAP concentration (either 0.1% (w/v) on FIG. 1C or 0.3% (w/v) on FIG. 1D) and the illumination time at 405 nm. A rapid decrease of the matrix weight, of up to about 40%, was observed 5 hours after the polymerization process (FIG. 1C-D). Then, a constant weight for at least 28 days was observed, indicating a good stability of the matrix in the culture medium at 37° C. (FIGS. 1C-D). As expected, rigidity, analyzed by rheology, greatly increased with the gelatin concentrations (FIGS. 1E-H), in a manner consistent with other reports showing that the mechanical properties of gelatin scaffolds are highly dependent on gelatin concentrations and crosslinking processes. A direct proportional relation was found between the methacrylated gelatin concentration and the elastic (G') and viscous modulus (G") with an exponential increased of G' from 0.05 kPa (FIG. 1E) to 2.12 kPa (FIG. 1G) when the concentration of methacrylated gelatin increased from 2.5% (w/v) to 15% (w/v), respectively. Based on these observations, the experiments that follow were carried out using a GelMa and LAP concentrations of 5% (w/v) and 0.1% (w/v), respectively, and an illumination time of 60 seconds (at 405 nm).

Viability of Immortalized Hepatic Cells in GelMa Cultures

Next, the short- and long-term viability of HuH-7 cells (an immortalized hepatic cell line derived from transformed hepatocellular carcinoma cells) in 3D GelMa culture (with GelMa 5% (w/v), LAP 0.1% (w/v)) was assessed before and after crosslinking (1 min illumination time) and bioprinting. As shown on FIGS. 2A-C, no decrease in HuH-7 cell viability (assessed through the WST-1 proliferation assay) could be observed after 4 hours in the GelMa culture, indicating that neither the GelMa matrix, the crosslinking nor the bioprinting processes were toxic at a short time after seeding. Interestingly, in the long-term, with a minimal LAP concentration (0.1% (w/v)) and a illumination time of 1 min, the cell viability (assessed through the WST-1 proliferation assay) increased until day 14 (FIG. 2D) and then remained constant thereafter at least until 28 days (FIG. 2E) showing that cells could survive and/or proliferate in the matrix long after bioprinting. Furthermore, as shown on FIG. 2F and on FIGS. 3A-C, the HuH-7 cells were able to divide in 3D GelMa culture since Ki 67 positive HuH-7 cells could be detected at day 5 (about 12% of the cells), day 10 (about 27% of the cells) and day 14 (about 20% of the cells), in accordance with the viability results (assessed through the WST-1 proliferation assay) described above. As shown on FIG. 2F and on FIGS. 3D-F, no or very little caspase 3 activity could be observed in the HuH-7 cells in 3D GelMa culture at day 5, 10 and 14 after seeding, whereas the cells responded well to an apoptotic inducer after cisplatin (CDDP) treatment at day 14 (data not shown), indicating that cell death was very limited.

Proliferation of HepaRG Cells in a GelMa Culture

The method of culturing of the invention was next applied to the gold standard immortalized human hepatic cells, the HepaRG cells. As described above, undifferentiated HepaRG were first cultured in a low-attachment plate for about 15 hours before being embedded in a GelMa matrix. Strikingly, undifferentiated HepaRG cells could not fully differentiate in the GelMa matrix if they were not first cultured in a low-attachment plate. As shown on FIGS. 19A-D, the expression of hepatic genes (ALB, ALDOB, HNF4A, and NR1H4, respectively) was compared in HepaRG cells cultured in a GelMa matrix according to the method of the invention and in HepaRG cells embedded in a GelMa matrix without being first cultured in a low-attachment plate. The expression of hepatic genes, notably that of ALDOB, HNF4A, and NR1H4 at day 14, was lower in HepaRG cells which were not first cultured in a low-attachment plate.

Undifferentiated HepaRG were cultured in a GelMa matrix according to the method of the invention in the absence of DMSO in order to avoid non-specific inductions of the Cyp3A4 cytochrome by DMSO previously observed during the differentiation of HepaRG in 2D standard culture conditions (referred to as 2D-DMSO culture) (Aninat et al., Drug Metab Dispos. 2006 January; 34(1):75-83).

HepaRG cells in 3D GelMa culture formed small clusters of cells, i.e., spheroids, 7 days after seeding (FIGS. 4A-I). The spheroids obtained were characterized by their polarized structure with multiple biliary canaliculi and by their small size. The majority of the observed spheroids had a diameter ranging from 30 to 100 μm, and consisted of from about 10 to about 50 cells.

Figure 5B:
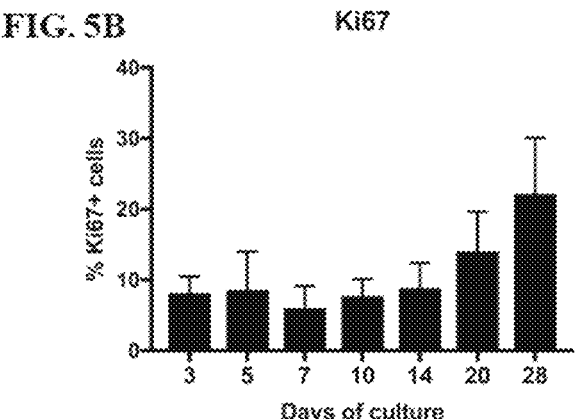
Figure 5C:
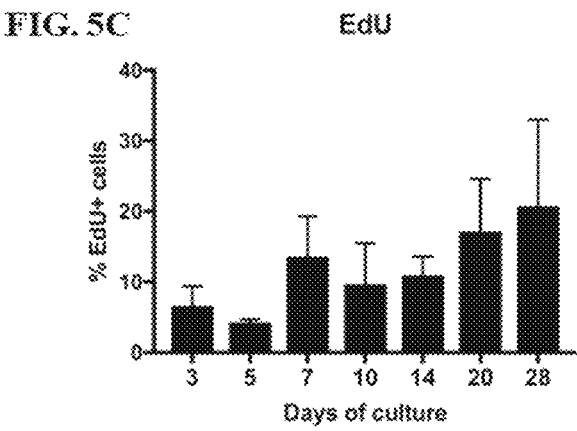

The cells appeared polarized as evidenced by the localization of E- and N-cadherins at the apico and lateral membranes (FIGS. 4A-F). Furthermore, the multi-drug resistance protein 2 (MRP2) was exclusively observed at apico-canicular areas (i.e., apical/canicular domains), confirming the polarization of the cells in the cell clusters (i.e., spheroids) over the duration of the culture (FIGS. 4G-I). CDH2/N-cadherin (a mesenchymal marker) was less expressed in HepaRG cells in GelMa cultures as compared to HepaRG cells in 2D-DMSO cultures while CDH1/E-cadherin (an epithelial marker) and ABCC2/MRP2 (an hepatocyte marker), poorly expressed in undifferentiated HepaRG, were expressed at the same level in HepaRG cells in GelMa cultures and in HepaRG cells in 2D-DMSO cultures, thus confirming an epithelial state of HepaRG cells (FIG. 4). Then, the proliferation potential of HepaRG in GelMa cultures was assessed by measuring the expressions of the cell division markers cyclin D1 and Ki67, as well as the incorporation of EdU during the DNA replication process. Only small differences could be observed in the expressions of these proliferation markers over time (FIGS. 5A-C). As shown on FIG. 5, the G1 and S phase markers, cyclin D1 (FIG. 5A) and Ki67 (FIG. 5B) respectively, were expressed in 10 to 20% of the HepaRG cells, depending on the day of culture. A similar proportion of EdU positive cells was detected (FIG. 5C). The proliferation of the HepaRG is MEK1/2-ERK1/2 dependent, since inhibition of the pathway with the U126 inhibitor could significantly abrogate the incorporation of EdU in the nuclei of the cells (16.4% EdU positive cells in the absence of U126 reduced to 0.9% EdU positive cells in the presence of U126, data not shown).

Differentiation of HepaRG Cells in a GelMa Culture

The expression of hepatic genes was compared in freshly isolated primary human hepatocytes, HepaRG cells at day 14 in 2D standard culture conditions (referred to as 2D-DMSO culture) and HepaRG cells at day 14 in 3D GelMa culture (data not shown). Gene expressions was measured by 3' SRP-RNA-Seq from RNAs HepaRG. The comparison showed that HepaRG cells in 2D-DMSO culture and 3D GelMa culture share a similar hepatic gene expression pattern. When compared to freshly isolated primary hepatocytes, HepaRG cells in both 2D-DMSO culture and 3D GelMa culture showed the same clusters of up- and down-regulated hepatic genes. In particular, 4 specific hepatic markers, ALB, ALDOB, HNF4A and SERPINA1, showed a level of expression similar for freshly isolated primary hepatocytes, HepaRG cells in 2D-DMSO culture and HepaRG cells in 3D GelMa culture.

Figure 6A:
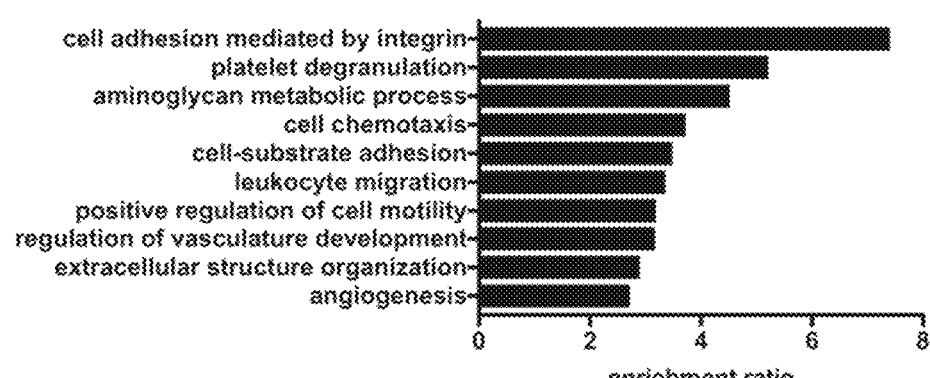
FIGS. 6A-6B illustrate the transcriptomic analysis of HepaRG cells in 2D DMSO culture or in 3D GelMa culture 6A is a bar graph showing hepatic genes sorted according to their function upregulated in HepaRG cells at day 14 in 3D GelMa culture (3D GelMa) as compared to HepaRG cells at day 14 in 2D standard culture conditions. 6B is a bar graph showing hepatic genes sorted according to their function downregulated in HepaRG cells at day 14 in 3D GelMa culture (3D GelMa) as compared to HepaRG cells at day 14 in 2D standard culture conditions.
Figure 6B:
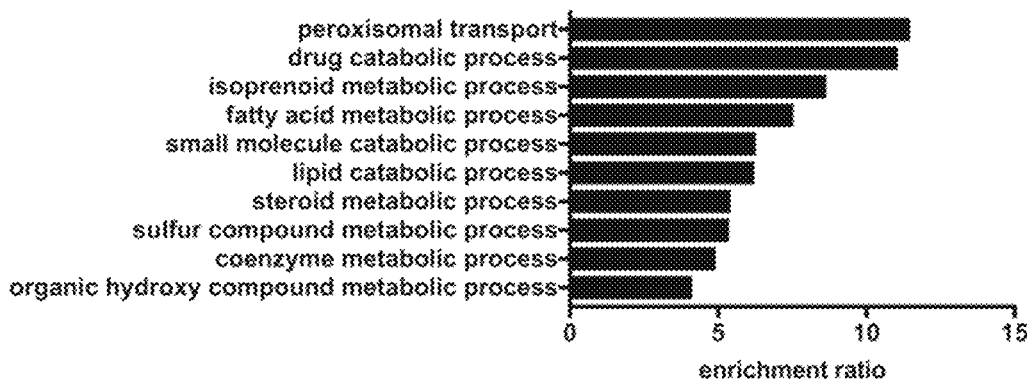

More precisely, FIG. 6A shows the set of genes sorted according to their function upregulated in HepaRG cells at day 14 in 3D GelMa culture as compared HepaRG cells at day 14 in 2D standard culture conditions and FIG. 6B shows the set of genes sorted according to their function down-regulated in HepaRG cells at day 14 in 3D GelMa culture as compared HepaRG cells at day 14 in 2D standard culture conditions. These data show that, compared to HepaRG cells in 2D-DMSO culture, in HepaRG cells in 3D GelMa culture genes implicated in chemotactism, cell adhesion and migration, and extracellular structure organization were over-expressed. Compared to HepaRG cells in 2D-DMSO culture, in HepaRG cells in 3D GelMa culture genes implicated in processes mainly linked to cell metabolism and catabolic process of endogen compounds (peroxisomal transport, isoprenoid metabolic process, fatty acid metabolic/catabolic process) and exogen compounds (drug catabolic process, small molecule catabolic process) were down-regulated.

Then, an analysis of liver-specific gene expressions (LiGEP signature) as defined by Kim et al. (Kim et al., Hepatology. 2017 November; 66(5):1662-1674) was carried out. This panel was based on the significantly differential RNA expressions between liver and non-liver samples. Kim et al. developed an algorithm based on RNA-sequencing (RNA-seq) analysis to assess the differentiation or maturation status of 93 liver-specific genes validated by expression profiles in human Protein Atlas database and by quantitative real-time PCR analysis. A modified version of this original list, excluding, inter alia, genes from xenobiotic metabolism, was used for transcriptomic analyzes. RNAs from freshly isolated primary human hepatocyte (PHH T0) were used here as a standard reference. The expression profile of freshly isolated primary human hepatocytes is considered to be closest to the liver in vivo but cannot be reproduced in vitro due to the extremely rapid dedifferentiation of the human hepatocytes in 2D culture. Here, if a decrease in the expression of hepatic genes can be observed during the comparison of HepaRG GelMa and HepaRG 2D DMSO with the freshly isolated PHH, one notes a maintenance of the expression of hepatic genes of the LiGEP signature with a great homology of the expression profiles of HepaRG in GelMa and 2D DMSO, with both HepaRG in 2D and 3D showing a quite similar pattern of many hepatic gene expression (e.g., ALB, ALDOB, SERPINA1, FGA, FGB, FGG).

As shown on FIG. 7, HepaRG cells in 3D GelMa culture (3D GelMa) showed a strong and constant expression of the mRNA encoding for proteins responsible for various hepatic functions (ALDOB (FIG. 7A), ALB (FIG. 7B), HNF4A (FIG. 7C), NR1H4 coding for the FXR protein (FIG. 7D), NR1I2 coding for the PXR protein (FIG. 7E), SERPINA1 (FIG. 7F), at short (7 days), medium (14 days) and long (28 days) times after seeding. The mRNA levels were equal to or greater than the mRNA levels of cells in 2D-DMSO cultures. The mRNA levels were significantly greater than the mRNA levels of undifferentiated HepaRG cells in 2D culture (without DMSO). These results were confirmed by analysis of the secretions of urea and albumin over time. As shown on FIG. 8, both the secretions of urea (FIG. 8A) and albumin (FIG. 8B) remained constant throughout the entire culture time. The secretion of albumin in HepaRG cells in 3D GelMa culture (3D GelMa) was comparable to that in HepaRG cells in 2D-DMSO cultures at day 14 (FIG. 8C).

Additionally, the decreased mRNA expression level of the biliary lineage markers SOX9 (FIG. 9A) and KRT19 (FIG. 9B) in HepaRG cells in 3D GelMa culture indicated that the HepaRG cells in 3D GelMa culture differentiated mainly via a hepatic lineage. By contrast, the HepaRG cells in standard 2D-DMSO culture differentiated both via a hepatic lineage and a biliary lineage, as previously observed (FIGS. 9A-B and Guillouzo et al., Chem Biol Interact. 2007 May 20; 168(1):66-73).

Next, the expression of phase I metabolism genes was compared in freshly isolated primary human hepatocytes, HepaRG cells at day 14 in 2D standard culture conditions (2D-DMSO culture) and HepaRG cells at day 14 in 3D GelMa culture (data not shown). The comparison showed that the expressions of most phase I enzymes are down-regulated in HepaRG cells in 3D GelMa culture, compared to HepaRG cells in 2D-DMSO culture.

The mRNA expression levels of Phase I enzymes were also quantified using RT-qPCR in HepaRG cells both in 3D GelMa culture and in 2D-DMSO culture, and in undifferentiated HepaRG cells in 2D culture (without DMSO). As shown on FIG. 10, depending on the enzymes, the mRNA expressions in HepaRG cells were higher (CYP1A1), were equal (CYP1A2) or lower (CYP3A4, CYP2B6, CYP2E1, CYP2C9) in 3D GelMa culture as compared to 2D-DMSO culture. The CYP1A and 1A2 activities were also assessed in HepaRG cells both in 3D GelMa culture and in 2D-DMSO culture. As shown on FIG. 11A-B, CYP1A and 1A2 activities could be induced in 3D GelMa culture cultures at the same level than in 2D-DMSO culture. In HepaRG cells in 3D GelMa culture, the induction of these activities could be observed throughout the entire culture time, thus allowing the analysis of short and long-term acute and chronic effects of drugs in the 3D GelMa culture until at least 30 days. CYP3A4, 2B6 and 1A2 activities could be induced from 2-, 6-, 16-fold, respectively, indicating that HepaRG cells in 3D GelMa culture respond well to all activators. Activations in HepaRG cells were higher in 3D GelMa culture than in 2D-DMSO culture (FIGS. 11C-G).

Figure 12A:
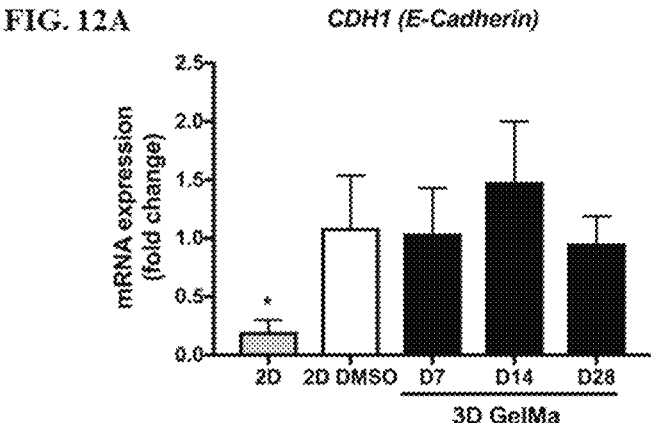
FIGS. 12A-12C illustrate the mRNA expression of genes encoding for cadherins and for the MRP2 drug transporter, in HepaRG cells in negative control 2D culture (without DMSO), in HepaRG cells in positive control 2D-DMSO culture, and in HepaRG cells in 3D GelMa culture according to the method of the invention. The mRNA expressions were assessed at day 14 in undifferentiated HepaRG cells in negative control 2D culture (2D—grey bars), at day 14 in HepaRG cells in positive control 2D-DMSO culture (2D DMSO—white bars), and at day 7 (D7), day 14 (D14) and day 28 (D28) in HepaRG cells in 3D GelMa culture (3D GelMa—black bars). Expression in HepaRG cells in 3D GelMa culture is expressed in relative quantity normalized to expression in HepaRG in 2D-DMSO culture. 12A is a histogram showing the mRNA expression of CDH1 encoding E-cadherin. 12B is a histogram showing the mRNA expression of CDH2 encoding N-cadherin. 12C is a histogram showing the mRNA expression of ABCC2 encoding MRP2.
Figure 12B:
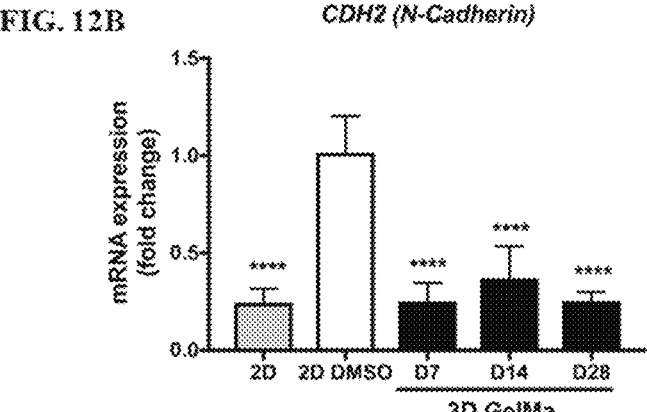
Figure 12C:
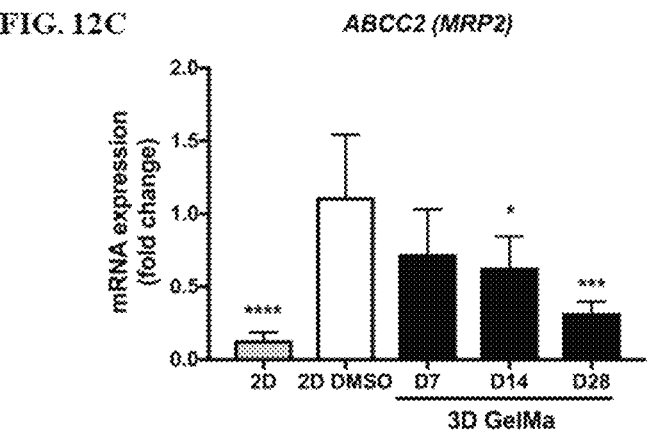
Figures 16A, 16B, 16C, 16D, 16E, 16F:
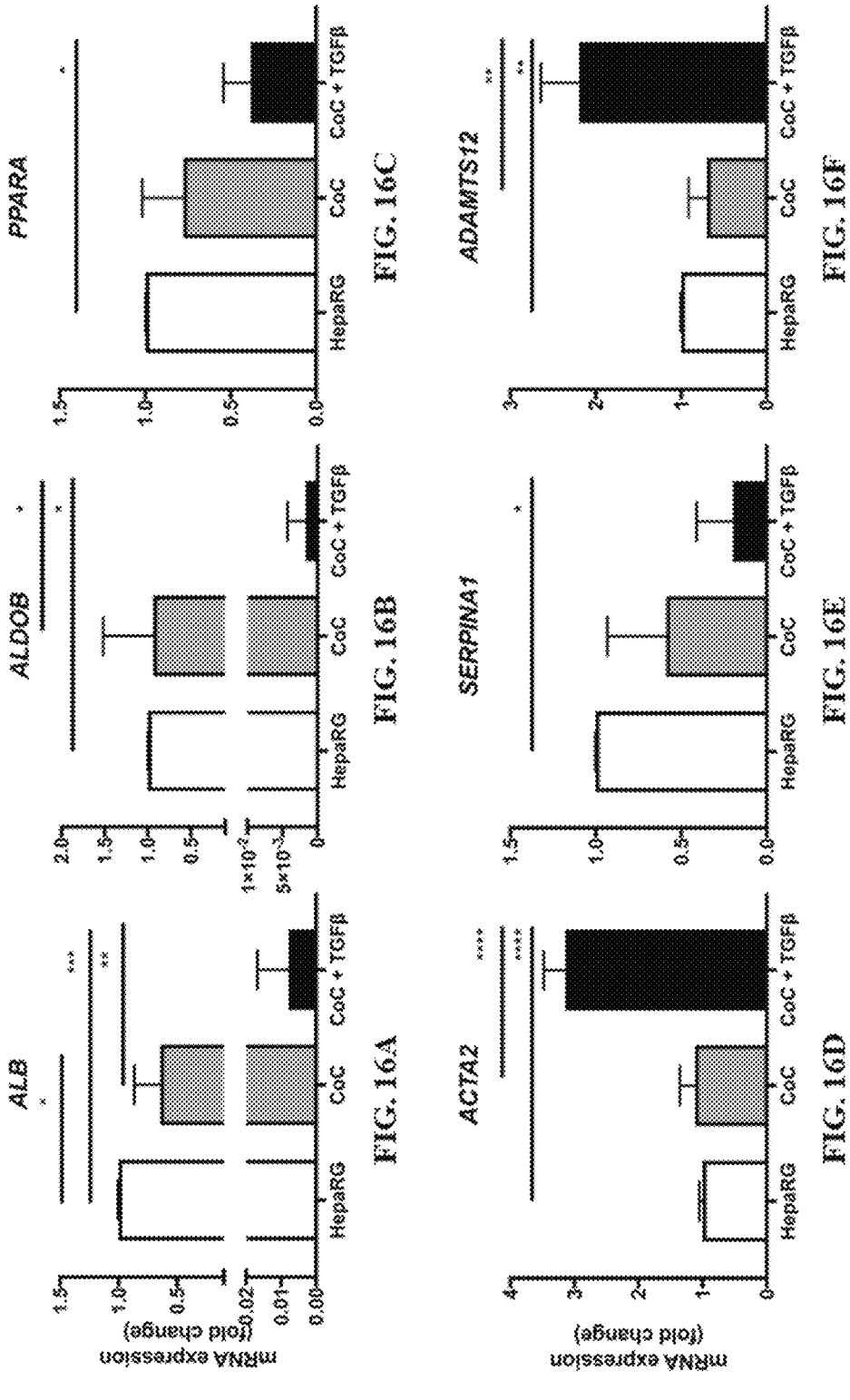
Figures 19A, 19B, 19C, 19D:
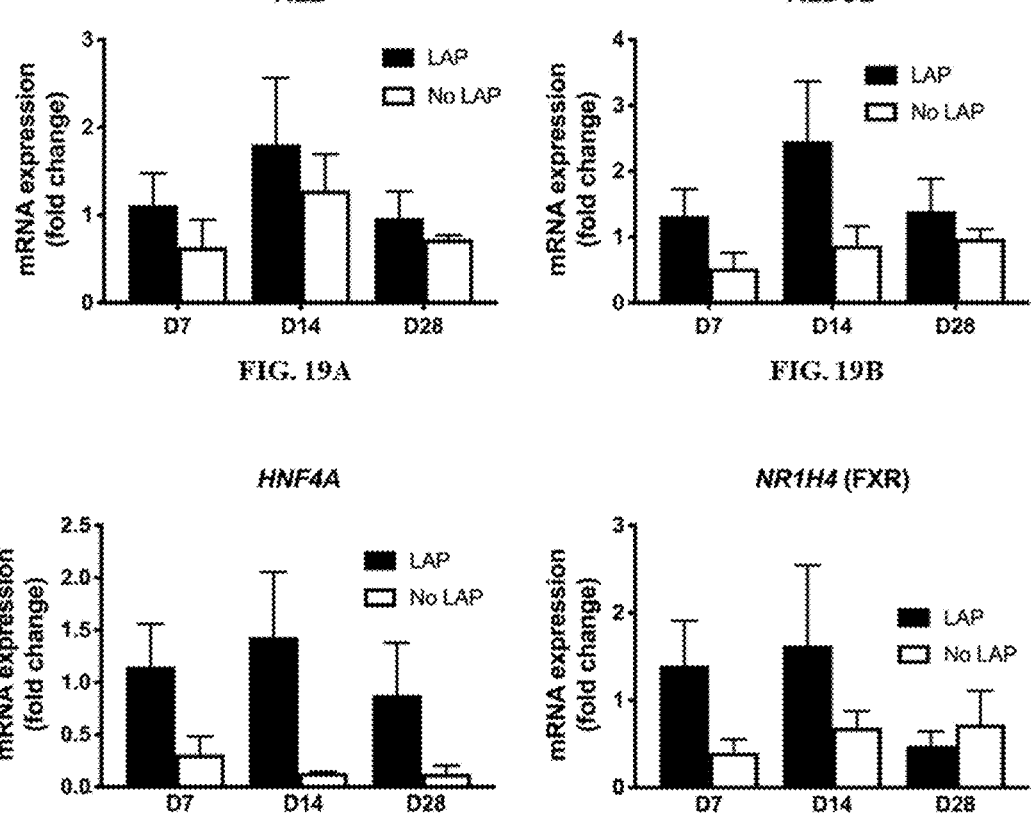
FIGS. 19A-19D illustrate the mRNA expression of genes encoding for proteins responsible for various hepatic functions in HepaRG cells at day 7 (D7), day 14 (D14), and day 28 (D28) in 3D GelMa culture according to the method of the invention (LAP—black bars) and in HepaRG cells embedded in a GelMa matrix without a first culture in a low-attachment plate (No LAP—white bars). Expression in HepaRG cells is expressed in relative quantity normalized to expression at day 7 in 3D GelMa culture according to the method of the invention. 19A is a histogram showing the mRNA expression of ALB (coding for albumin). 19B is a histogram showing the mRNA expression of ALDOB (coding for aldolase). 19C is a histogram showing the mRNA expression of HNF4A. 19D is a histogram showing the mRNA expression of NR1H4 (coding for the FXR protein).

The mRNA expression levels of Phase II and Phase III enzymes were also assessed in HepaRG cells both in 3D GelMa culture and in 2D-DMSO culture. As seen with the phase I enzymes, the mRNA expression of the Phase II and Phase III enzymes in HepaRG cells in 3D GelMa culture were lower than, equal to or greater than those in HepaRG cells in 2D DMSO culture, depending on the enzymes (data not shown). As mentioned above, the phase II MRP2 transporter was located exclusively at the apico/canicular area showing a good polarization of the HepaRG cells in the 3D GelMa culture throughout the entire culture time. Furthermore, the expression of CDH1 encoding E-cadherin (FIG. 12A), CDH2 encoding N-cadherin (FIG. 12B) and ABCC2 encoding MRP2 (FIG. 12C) were quantified using RT-qPCR in HepaRG cells both in 3D GelMa culture and in 2D-DMSO culture, and in undifferentiated HepaRG cells in 2D culture (without DMSO). As shown on FIG. 12, N-cadherin (encoded by CDH2) was less expressed in HepaRG cells in 3D GelMa cultures as compared to HepaRG cells in 2D-DMSO cultures while E-cadherin (encoded by CDH1) was expressed at the same level in HepaRG cells in GelMa cultures and in HepaRG cells in 2D-DMSO cultures, thus confirming an epithelial state of HepaRG cells.

The data on Huh7 and HepaRG cells showed a stable hepatic differentiation, notably close or even higher than that of HepaRG cells cultured in 2D with DMSO according to the gold standard culture method. From the start of the 3D GelMa culture, the differentiation increased until day 15 of the culture. The differentiation was optimal at day 15 and stayed at a high level until day 28, allowing long-term and chronic exposures of drugs and environmental products, in absence of DMSO.

In conclusion, the data presented above demonstrate that HepaRG cells in 3D bioprinted GelMa display long-term survival and a highly differentiate state with a proliferating capability. The proliferative and differentiated properties of the HepaRG cells may be of great interest to enable genotoxic and mutagen studies of hepatic drugs and environmental products that need to be metabolized by the liver to give genotoxic and/or mutagenic DNA products.

Example 2

Materials and Methods

Material

Cells

The HepaRG cell line was used. Other cells used in the following experiments include human hepatic stellate cells (LX-2 cells derived from activated stellate cells (Xu et al., Gut. 2005 January; 54(1):142-51) and endothelial cells (Human umbilical vein endothelial cells or HUVECs).

Reagents

DMEM medium L-glutamine was obtained from Gibco (ThermoFisher, Waltham, MA USA). EBM™-2 Endothelial Cell Growth basal medium and EGM™-2 BulletKit™ were obtained from LONZA (Aubergenville, France).

Methods

Cell Culture

Undifferentiated HepaRG cells (Biopredic, Saint Grégoire, France) were cultured as described above (see Example 1). For control experiments in 2D culture (also referred to as 2D-DMSO), hepatic differentiation of HepaRG cells was induced in 2D culture by treatment with 2% DMSO (D4540, Sigma-Aldrich, St. Louis, MO, USA) for an additional 14 days.

LX-2 cells (provided by the Dr N. Theret, Irset, France) were cultured in DMEM comprising 4.5 g/L of both glucose and pyruvate supplemented with 10% (v/v) fetal bovine serum (EuroBio), 100 units/mL penicillin and 100 µg/mL streptomycin and 2 mM L-glutamine.

Human umbilical vein endothelial cells also referred to as HUVECs (ZHC-2402, CellWorks, Buckingham, UK) were cultured in a mix of EBM™-2 Endothelial Cell Growth basal medium and William's E medium (1:1) supplemented with 10% (v/v) fetal bovine serum Hyclone III, 100 units/ mL penicillin, 100 µg/mL streptomycin, 5 µg/mL human insulin, 2 mM L-glutamine and $5 \times 10^{-5}$ M hydrocortisone hemisuccinate. hFGF-B (human fibroblast growth factor-basic), VEGF (vascular endothelial growth factor), ascorbic acid, hEGF (human epidermal growth factor), GA-1000 (gentamicin sulfate-amphotericin) and heparin issued from the EGM™-2 BulletKit™ were added to the medium at concentrations recommended by the supplier.

HepaRG cells and/or LX-2 cells were included in a GelMa matrix as described hereinabove (see Example 1).

For coculture constructs, the bioprinted 3D structure comprising HepaRG cells and LX-2 cells was cultured during a week, before being put in a low attachment plate containing $1 \times 10^6$ HUVECs per mL of medium.

Results

Culture of Human Hepatic Stellate Cells in a GelMa Matrix

Micro-engineered cocultures with HepaRG, LX-2 and HUVECs were developed, with the aim of obtaining an in vitro model for evaluating the fibrotic process in vitro.

First, the culture of LX-2 cells alone in 3D GelMa culture was assessed, with or without treatment with TGFβ-1, a classical pro-fibrotic cytokine (Czaja et al., J Cell Biol. 1989 June; 108(6):2477-82). From day 2 of culture, cells were treated with vehicle (controls) or TGFβ-1 (5 ng/mL every 48 h) for two weeks (activation) or for one week followed by an additional week without TGFβ-1 (reversion) (FIG. 13A). LX-2 is a cell line derived from human hepatic stellate cells. As shown on FIG. 13, surprisingly, the LX-2 cells remained round in the GelMa matrix while, in a collagen 1 matrix, they adopted a more elongated phenotype suggesting a transition to a myofibrobroblastic phenotype (FIG. 13B-C). In 3D GelMa culture, the LX-2 cells displayed a good viability until at least 14 days of culture (FIG. 13D). Then, the mRNA expression of ACTA2, ADAMTS12, LPL, COL1A1, MMP2, TGFβ-1 and TIMP1 was assessed in LX-2 cells in 3D GelMa culture, stimulated or not by TGFβ-1 (FIGS. 14A-G, respectively). In 3D GelMa culture, expression of ACTA2, the major control of stellate cell activation, was clearly down-regulated as compared to LX-2 cells cultivated on a 2D support. After TGFβ-1 treatment, the mRNA expression of the ACTA2, COL1A1, MMP2 and TIMP1, encoding enzymes or components involved in extracellular matrix (ECM) homeostasis, were clearly increased in a time-dependent manner. These inductions were reversible and, following TGFβ-1 removal at day 7, the mRNA expression of the markers at day 16 decreased and returned to a level equivalent to that observed in the untreated control.

These results indicate that 3D GelMa provide suitable culture conditions for human hepatic stellate cells.

SHG microscopy was used to visualize fibrillar collagen, mostly collagen-1 and -3. Briefly, SHG relies on the non-linear optical interactions with non-centromeric fibrillar structures, such as collagen type I, allowing their detection and quantification in 3D tissues. Very few collagen fibrils or no collagen fibrils at all could be observed after induction of the LX-2 cells by TGFβ-1 (see FIG. 18H). No collagen deposition could be observed in HepaRG cells in 3D GelMa culture when the HepaRG cells were cultured alone in GelMa culture, either with or without TGFβ-1 treatment (see FIGS. 18A & E). These results indicate that the culture of human hepatocyte cells or human hepatic stellate cells alone does not allow a faithful hepatic model. For example, such culture is not suitable for the study of liver fibrosis.

Coculture of HepaRG Cells, Human Hepatic Stellate Cells and Human Endothelial Cells Then, HepaRG cells, LX-2 cells and HUVECs were cocultured together (FIG. 15A) within a suitable structure with large channels allowing solute/gas exchanges with the medium where the LX-2 were bioprinted inside the channels and the HUVECs were allowed to adhere and colonize the entire surface of the GelMa matrix (FIG. 15B).

As controls, HepaRG cells were bioprinted either alone or with HUVECs alone (HepaRG+HUVECs). The green fluorescent protein (GFP) allowed to visualize the homogeneous seeding of fluorescent HUVECs at the surface of the GelMa matrix, including into the channels, 4 days after seeding (FIG. 15C).

The mRNA expression of hepatic genes (ALB, ALDOB, PPARA and SERPINA1) and of myofibroblastic transition genes and extracellular matrix remodeling genes (ACTA2, ADAMTS12, COL1A1, COL3A1, MMP2, MMP9 and TIMP1) was assessed at day 21 (i) in HepaRG alone in 3D GelMa culture, (ii) in HepaRG in 3D GelMa culture with LX-2 cells and HUVECs (CoC) and (iii) in HepaRG in 3D GelMa culture with LX-2 cells and HUVECs (CoC) activated with TGFβ-1 treatment for 7 days (FIGS. 16A-K). When stimulated by TGFβ-1, a significant loss of hepatic functionality was observed through a decrease in hepatic gene mRNA expression (see expression of ALB, ALDOB, PPARA and SERPINA1, FIGS. 16A-C & E, respectively) and albumin secretion (see FIG. 17B) and an increase of genes involved in ECM homeostasis (see expression of ACTA2, ADAMTS12, COL1A1, COL3A1, MMP2, MMP9 and TIMP1, FIGS. 16D & F-K, respectively). Nevertheless, no specific release of LDH (a cell death marker) in the medium was observed (see FIG. 17B), and urea secretion remained stable over the 21 days of culture with or without TGFβ-1 treatment (data not shown). The albumin secretion of the HepaRG cells in coculture with the LX-2 cells and HUVECs (CoC) was also assessed and compared to that of HepaRG cells cultured alone (HepaRG) and bioprinted in GelMa matrix under the same conditions. The data showed that the albumin expression/secretion capacities over time of the HepaRG cells were the same in the two cultures, indicating that the coculture did not alter or modify the high functionality of the HepaRG cells in 3D GelMa culture (FIG. 17A).

Basal expression of COL1A1 was significantly higher in HepaRG+LX-2+HUVECs (CoC) than in HepaRG alone or in HepaRG+HUVECs, at a level close to that of LX-2 in GelMa alone (FIG. 17C). When activated by TGFβ-1, a significant increase in COL1A1 expression was observed in all three conditions, correlated with pro-collagen 1a1 secretion in medium (FIG. 17D). Without TGFβ-1 stimulation, almost no pro-collagen 1a1 could be detected in HepaRG or HepaRG+HUVECs, whereas TGFβ-1 treatment significatively induces its secretion.

In HepaRG+LX-2+HUVECs (CoC), a high basal secretion was measured at day 21 and no significant increase after TGFβ-1 activation could be detected. The level of pro-collagen 1a1 secretion in HepaRG+LX-2+HUVECs was close to that of TGFβ-1 activated HepaRG or HepaRG+HUVECs.

The deposition of the fibrillar collagen in the HepaRG-LX-2-Huvex cocultures was assessed at day 21 with SHG microscopy (FIG. 18). As negative control, as mentioned above, no deposition of collagen was observed when HepaRG cells were culture alone in 3D GelMa. Strikingly, SHG microscopy allowed to detect collagen fibrils within the matrix in cocultures of HepaRG+LX-2+HUVECs (CoC), stimulated or not by TGFβ (see FIGS. 18C & G). No collagen deposition could be observed either in HepaRG cultured alone (see FIGS. 18A & E) or in HepaRG+HU-VECs (see FIGS. 18B & F), and, unexpectedly, activated or not by TGFβ-1. Interestingly, no collagen fibrils were ever observed after induction of the LX-2 cells by TGFβ-1 in 3D GelMa when LX-2 cells were cultured alone (see FIG. 18H).

In conclusion, the data presented above demonstrate that HepaRG cultured in 3D GelMa in the presence of other types of cells, such as human hepatic stellate cells and human endothelial cells allows the development of complex multicellular hepatic models, that may be used for example as a fibrosis model, for studying collagen synthesis and deposition.

---

The invention claimed is:

1. A method of obtaining 3D cell structures comprising differentiated human hepatic cells, said method comprising:
   a) culturing stem cell-derived or immortalized human hepatic progenitors in a non-adherent culture vessel for a duration ranging from 12 h to 24 h;
   b) transferring the stem cell-derived or immortalized human hepatic progenitors to a culture medium comprising methacrylated gelatin (GelMa), thereby embedding the stem cell-derived or immortalized human hepatic progenitors in a GelMa matrix; and
   c) covering the GelMa matrix with culture medium and culturing the stem cell-derived or immortalized human hepatic progenitors embedded in the GelMa matrix;

wherein the stem cell-derived or immortalized human hepatic progenitors differentiate into human hepatic cells and cluster into 3D cell structures after being embedded in the GelMa matrix, thereby obtaining 3D cell structures comprising differentiated human hepatic cells.

2. The method according to claim 1, wherein at step a) the non-adherent culture vessel is a low or ultra-low attachment culture vessel.

3. The method according to claim 1, wherein at step b) the stem cell-derived or immortalized human hepatic progenitors are transferred to a culture medium comprising methacrylated gelatin (GelMa) at a final concentration ranging from about 1% (w/v) to about 20% (w/v).

4. The method according to claim 1, wherein at step c) the stem cell-derived or immortalized human hepatic progenitors embedded in the GelMa matrix are cultured for at least seven days.

5. The method according to claim 1, wherein the culture medium comprises insulin and a glucocorticoid.

6. The method according to claim 1, further comprising:

d) incubating the 3D cell structures comprising differentiated human hepatic cells embedded in the GelMa matrix with a collagenase or an enzyme mixture with collagenolytic activity, thereby isolating the 3D cell structures comprising differentiated human hepatic cells from the GelMa matrix.

7. The method according to claim 1, wherein the differentiated human hepatic cells are human hepatocytes or hepatocyte-like cells.

8. The method according to claim 1, wherein the stem cell-derived or immortalized human hepatic progenitors are hepatocellular carcinoma-derived and/or transformed human hepatic progenitors.

9. The method according to claim 1, wherein the stem cell-derived or immortalized human hepatic progenitors are undifferentiated HepaRG cells.

10. A method for engineering an artificial liver model or an artificial liver organ comprising differentiated human hepatic cells, the method comprising culturing stem cell-derived or immortalized human hepatic progenitors according to the method of claim 1 with at least another type of cells, wherein the stem cell-derived or immortalized human hepatic progenitors embedded in the GelMa matrix are contacted with the at least another type of cells.

11. The method according to claim 10, wherein said at least another type of cells is embedded in a matrix.

12. The method according to claim 10, wherein said at least another type of cells is another type of hepatic cells.

13. The method according to claim 10, wherein the stem cell-derived or immortalized human hepatic progenitors are cultured with stellate cells and/or endothelial cells.

14. An in vitro method for assessing the metabolism, toxicity and/or therapeutic effects of a compound, the method comprising:

a) obtaining 3D cell structures comprising differentiated human hepatic cells according to the method of claim 1;

b) contacting the 3D cell structures comprising differentiated human hepatic cells with a compound; and c) assessing the metabolism, toxicity and/or therapeutic effects of the compound on the 3D cell structures comprising differentiated human hepatic cells.

15. The in vitro method according to claim 14 wherein the differentiated human hepatic cells are human hepatocytes or hepatocyte-like cells.

* * * * *

SEQUENCE LISTING

```
<160> NUMBER OF SEQ ID NOS: 56

<210> SEQ ID NO 1
<211> LENGTH: 23
<212> TYPE: DNA
<213> ORGANISM: Artificial Sequence
<220> FEATURE:
<223> OTHER INFORMATION: primer

<400> SEQUENCE: 1
tgcttgaatg tgctgatgac agg                                    23

<210> SEQ ID NO 2
<211> LENGTH: 25
<212> TYPE: DNA
<213> ORGANISM: Artificial Sequence
<220> FEATURE:
<223> OTHER INFORMATION: primer

<400> SEQUENCE: 2
aaggcaagtc agcaggcatc tcatc                                  25

<210> SEQ ID NO 3
<211> LENGTH: 20
<212> TYPE: DNA
<213> ORGANISM: Artificial Sequence
<220> FEATURE:
<223> OTHER INFORMATION: primer

<400> SEQUENCE: 3
gtccatccag cctcgctatc                                        20

<210> SEQ ID NO 4
<211> LENGTH: 20
<212> TYPE: DNA
<213> ORGANISM: Artificial Sequence
<220> FEATURE:
<223> OTHER INFORMATION: primer

<400> SEQUENCE: 4
accagtccat tctgctgaca                                        20

<210> SEQ ID NO 5
<211> LENGTH: 19
<212> TYPE: DNA
<213> ORGANISM: Artificial Sequence
<220> FEATURE:
<223> OTHER INFORMATION: primer

<400> SEQUENCE: 5
```

-continued cgggaatgca gttgaggat                                              19

<210> SEQ ID NO 6
<211> LENGTH: 19
<212> TYPE: DNA
<213> ORGANISM: Artificial Sequence
<220> FEATURE:
<223> OTHER INFORMATION: primer

<400> SEQUENCE: 6
aggatggtgt aagcgatgg                                             19

<210> SEQ ID NO 7
<211> LENGTH: 20
<212> TYPE: DNA
<213> ORGANISM: Artificial Sequence
<220> FEATURE:
<223> OTHER INFORMATION: primer

<400> SEQUENCE: 7
gtgcatgaag gacagcctct                                            20

<210> SEQ ID NO 8
<211> LENGTH: 20
<212> TYPE: DNA
<213> ORGANISM: Artificial Sequence
<220> FEATURE:
<223> OTHER INFORMATION: primer

<400> SEQUENCE: 8
atgccatctt catccacctt                                            20

<210> SEQ ID NO 9
<211> LENGTH: 20
<212> TYPE: DNA
<213> ORGANISM: Artificial Sequence
<220> FEATURE:
<223> OTHER INFORMATION: primer

<400> SEQUENCE: 9
gagcaggtcc gaggttactg                                            20

<210> SEQ ID NO 10
<211> LENGTH: 20
<212> TYPE: DNA
<213> ORGANISM: Artificial Sequence
<220> FEATURE:
<223> OTHER INFORMATION: primer

<400> SEQUENCE: 10
gctcactatc agctcgcaca                                            20

<210> SEQ ID NO 11
<211> LENGTH: 20
<212> TYPE: DNA
<213> ORGANISM: Artificial Sequence
<220> FEATURE:
<223> OTHER INFORMATION: primer

<400> SEQUENCE: 11
gacattggcg ttctcatcca                                            20

<210> SEQ ID NO 12
<211> LENGTH: 20
<212> TYPE: DNA

```
<213> ORGANISM: Artificial Sequence
<220> FEATURE:
<223> OTHER INFORMATION: primer

<400> SEQUENCE: 12
agaagctatg ggtcaaccca                                                20

<210> SEQ ID NO 13
<211> LENGTH: 21
<212> TYPE: DNA
<213> ORGANISM: Artificial Sequence
<220> FEATURE:
<223> OTHER INFORMATION: primer

<400> SEQUENCE: 13
tggagacctt ccgacactcc t                                              21

<210> SEQ ID NO 14
<211> LENGTH: 20
<212> TYPE: DNA
<213> ORGANISM: Artificial Sequence
<220> FEATURE:
<223> OTHER INFORMATION: primer

<400> SEQUENCE: 14
cgttgtgtcc cttgttgtgc                                                20

<210> SEQ ID NO 15
<211> LENGTH: 24
<212> TYPE: DNA
<213> ORGANISM: Artificial Sequence
<220> FEATURE:
<223> OTHER INFORMATION: primer

<400> SEQUENCE: 15
ttcctactgc ttccgtctat caaa                                           24

<210> SEQ ID NO 16
<211> LENGTH: 20
<212> TYPE: DNA
<213> ORGANISM: Artificial Sequence
<220> FEATURE:
<223> OTHER INFORMATION: primer

<400> SEQUENCE: 16
gtgcagaatc ccacagctca                                                20

<210> SEQ ID NO 17
<211> LENGTH: 20
<212> TYPE: DNA
<213> ORGANISM: Artificial Sequence
<220> FEATURE:
<223> OTHER INFORMATION: primer

<400> SEQUENCE: 17
gtgaaggaag ccctgattga                                                20

<210> SEQ ID NO 18
<211> LENGTH: 20
<212> TYPE: DNA
<213> ORGANISM: Artificial Sequence
<220> FEATURE:
<223> OTHER INFORMATION: primer

<400> SEQUENCE: 18
tcctcttgaa cacggtcctc                                                20
```

```
<210> SEQ ID NO 19
<211> LENGTH: 20
<212> TYPE: DNA
<213> ORGANISM: Artificial Sequence
<220> FEATURE:
<223> OTHER INFORMATION: primer

<400> SEQUENCE: 19
ggacagagac gacaagcaca                                          20

<210> SEQ ID NO 20
<211> LENGTH: 21
<212> TYPE: DNA
<213> ORGANISM: Artificial Sequence
<220> FEATURE:
<223> OTHER INFORMATION: primer

<400> SEQUENCE: 20
aatggacatg aacaaccctc a                                        21

<210> SEQ ID NO 21
<211> LENGTH: 20
<212> TYPE: DNA
<213> ORGANISM: Artificial Sequence
<220> FEATURE:
<223> OTHER INFORMATION: primer

<400> SEQUENCE: 21
ttgaagcctc tcgttgaccc                                          20

<210> SEQ ID NO 22
<211> LENGTH: 19
<212> TYPE: DNA
<213> ORGANISM: Artificial Sequence
<220> FEATURE:
<223> OTHER INFORMATION: primer

<400> SEQUENCE: 22
cgtggtggga tacagccaa                                           19

<210> SEQ ID NO 23
<211> LENGTH: 24
<212> TYPE: DNA
<213> ORGANISM: Artificial Sequence
<220> FEATURE:
<223> OTHER INFORMATION: primer

<400> SEQUENCE: 23
cttcatccaa tggactgcat aaat                                     24

<210> SEQ ID NO 24
<211> LENGTH: 28
<212> TYPE: DNA
<213> ORGANISM: Artificial Sequence
<220> FEATURE:
<223> OTHER INFORMATION: primer

<400> SEQUENCE: 24
tcccaagtat aacactctac acagacaa                                 28

<210> SEQ ID NO 25
<211> LENGTH: 19
<212> TYPE: DNA
<213> ORGANISM: Artificial Sequence
<220> FEATURE:
```

-continued

<223> OTHER INFORMATION: primer

<400> SEQUENCE: 25
ggaggatcaa aggggatga                                              19

<210> SEQ ID NO 26
<211> LENGTH: 19
<212> TYPE: DNA
<213> ORGANISM: Artificial Sequence
<220> FEATURE:
<223> OTHER INFORMATION: primer

<400> SEQUENCE: 26
cagttgcccc cgtttttac                                              19

<210> SEQ ID NO 27
<211> LENGTH: 20
<212> TYPE: DNA
<213> ORGANISM: Artificial Sequence
<220> FEATURE:
<223> OTHER INFORMATION: primer

<400> SEQUENCE: 27
gtggacctga cctgccgtct                                             20

<210> SEQ ID NO 28
<211> LENGTH: 20
<212> TYPE: DNA
<213> ORGANISM: Artificial Sequence
<220> FEATURE:
<223> OTHER INFORMATION: primer

<400> SEQUENCE: 28
ggaggagtgg gtgtcgctgt                                             20

<210> SEQ ID NO 29
<211> LENGTH: 20
<212> TYPE: DNA
<213> ORGANISM: Artificial Sequence
<220> FEATURE:
<223> OTHER INFORMATION: primer

<400> SEQUENCE: 29
aacctgttgc aggagatgct                                             20

<210> SEQ ID NO 30
<211> LENGTH: 20
<212> TYPE: DNA
<213> ORGANISM: Artificial Sequence
<220> FEATURE:
<223> OTHER INFORMATION: primer

<400> SEQUENCE: 30
ttgccttgtt cccatttttc                                             20

<210> SEQ ID NO 31
<211> LENGTH: 22
<212> TYPE: DNA
<213> ORGANISM: Artificial Sequence
<220> FEATURE:
<223> OTHER INFORMATION: primer

<400> SEQUENCE: 31
tgagcaagtt tgaaacgcac at                                          22

-continued

```
<210> SEQ ID NO 32
<211> LENGTH: 21
<212> TYPE: DNA
<213> ORGANISM: Artificial Sequence
<220> FEATURE:
<223> OTHER INFORMATION: primer

<400> SEQUENCE: 32
agctcttctc ctgccgtctc t                                      21

<210> SEQ ID NO 33
<211> LENGTH: 20
<212> TYPE: DNA
<213> ORGANISM: Artificial Sequence
<220> FEATURE:
<223> OTHER INFORMATION: primer

<400> SEQUENCE: 33
ccaggacata cacccctttg                                        20

<210> SEQ ID NO 34
<211> LENGTH: 20
<212> TYPE: DNA
<213> ORGANISM: Artificial Sequence
<220> FEATURE:
<223> OTHER INFORMATION: primer

<400> SEQUENCE: 34
ctacctgtga tgccgaacaa                                        20

<210> SEQ ID NO 35
<211> LENGTH: 22
<212> TYPE: DNA
<213> ORGANISM: Artificial Sequence
<220> FEATURE:
<223> OTHER INFORMATION: primer

<400> SEQUENCE: 35
caccgtgaag gtgcctatga tg                                     22

<210> SEQ ID NO 36
<211> LENGTH: 22
<212> TYPE: DNA
<213> ORGANISM: Artificial Sequence
<220> FEATURE:
<223> OTHER INFORMATION: primer

<400> SEQUENCE: 36
ggcattgccc aggtatttca tc                                     22

<210> SEQ ID NO 37
<211> LENGTH: 20
<212> TYPE: DNA
<213> ORGANISM: Artificial Sequence
<220> FEATURE:
<223> OTHER INFORMATION: primer

<400> SEQUENCE: 37
gcctttttgt ccatcccttt                                        20

<210> SEQ ID NO 38
<211> LENGTH: 21
<212> TYPE: DNA
<213> ORGANISM: Artificial Sequence
<220> FEATURE:
<223> OTHER INFORMATION: primer
```

```
<400> SEQUENCE: 38
gcttgcattg tttttgtgtc a                                                    21

<210> SEQ ID NO 39
<211> LENGTH: 22
<212> TYPE: DNA
<213> ORGANISM: Artificial Sequence
<220> FEATURE:
<223> OTHER INFORMATION: primer

<400> SEQUENCE: 39
ccaaactttt cctccctgaa cc                                                   22

<210> SEQ ID NO 40
<211> LENGTH: 23
<212> TYPE: DNA
<213> ORGANISM: Artificial Sequence
<220> FEATURE:
<223> OTHER INFORMATION: primer

<400> SEQUENCE: 40
gtgatgctga gaagtttcgt tga                                                  23

<210> SEQ ID NO 41
<211> LENGTH: 21
<212> TYPE: DNA
<213> ORGANISM: Artificial Sequence
<220> FEATURE:
<223> OTHER INFORMATION: primer

<400> SEQUENCE: 41
tattccttcg ttactactgc t                                                    21

<210> SEQ ID NO 42
<211> LENGTH: 20
<212> TYPE: DNA
<213> ORGANISM: Artificial Sequence
<220> FEATURE:
<223> OTHER INFORMATION: primer

<400> SEQUENCE: 42
aagtccagag ctacataaca                                                      20

<210> SEQ ID NO 43
<211> LENGTH: 20
<212> TYPE: DNA
<213> ORGANISM: Artificial Sequence
<220> FEATURE:
<223> OTHER INFORMATION: primer

<400> SEQUENCE: 43
cacgacgtgg ctgtccttct                                                      20

<210> SEQ ID NO 44
<211> LENGTH: 26
<212> TYPE: DNA
<213> ORGANISM: Artificial Sequence
<220> FEATURE:
<223> OTHER INFORMATION: primer

<400> SEQUENCE: 44
ccgaatcttc attgatgtta caactg                                               26

<210> SEQ ID NO 45
<211> LENGTH: 19
```

-continued

```
<212> TYPE: DNA
<213> ORGANISM: Artificial Sequence
<220> FEATURE:
<223> OTHER INFORMATION: primer

<400> SEQUENCE: 45
cctcaagggc tccaacgag                                              19

<210> SEQ ID NO 46
<211> LENGTH: 20
<212> TYPE: DNA
<213> ORGANISM: Artificial Sequence
<220> FEATURE:
<223> OTHER INFORMATION: primer

<400> SEQUENCE: 46
tcaatcactg tcttgcccca                                             20

<210> SEQ ID NO 47
<211> LENGTH: 20
<212> TYPE: DNA
<213> ORGANISM: Artificial Sequence
<220> FEATURE:
<223> OTHER INFORMATION: primer

<400> SEQUENCE: 47
ggggagctgg ctacttctcg                                             20

<210> SEQ ID NO 48
<211> LENGTH: 20
<212> TYPE: DNA
<213> ORGANISM: Artificial Sequence
<220> FEATURE:
<223> OTHER INFORMATION: primer

<400> SEQUENCE: 48
tgaggtcctt gaccattagg                                             20

<210> SEQ ID NO 49
<211> LENGTH: 21
<212> TYPE: DNA
<213> ORGANISM: Artificial Sequence
<220> FEATURE:
<223> OTHER INFORMATION: primer

<400> SEQUENCE: 49
tcattcccgg agtagcagag t                                           21

<210> SEQ ID NO 50
<211> LENGTH: 19
<212> TYPE: DNA
<213> ORGANISM: Artificial Sequence
<220> FEATURE:
<223> OTHER INFORMATION: primer

<400> SEQUENCE: 50
ggccacaagt tttggcacc                                              19

<210> SEQ ID NO 51
<211> LENGTH: 20
<212> TYPE: DNA
<213> ORGANISM: Artificial Sequence
<220> FEATURE:
<223> OTHER INFORMATION: primer

<400> SEQUENCE: 51
```

-continued

```
caaggaccgg tttatttggc                                          20

<210> SEQ ID NO 52
<211> LENGTH: 21
<212> TYPE: DNA
<213> ORGANISM: Artificial Sequence
<220> FEATURE:
<223> OTHER INFORMATION: primer

<400> SEQUENCE: 52
attccctgcg aagaacacag g                                        21

<210> SEQ ID NO 53
<211> LENGTH: 19
<212> TYPE: DNA
<213> ORGANISM: Artificial Sequence
<220> FEATURE:
<223> OTHER INFORMATION: primer

<400> SEQUENCE: 53
cacccacaga cggccttct                                           19

<210> SEQ ID NO 54
<211> LENGTH: 22
<212> TYPE: DNA
<213> ORGANISM: Artificial Sequence
<220> FEATURE:
<223> OTHER INFORMATION: primer

<400> SEQUENCE: 54
cttctggtgt ccccacgaac tt                                       22

<210> SEQ ID NO 55
<211> LENGTH: 19
<212> TYPE: DNA
<213> ORGANISM: Artificial Sequence
<220> FEATURE:
<223> OTHER INFORMATION: primer

<400> SEQUENCE: 55 cttcgccct agcaacgag                                            19

<210> SEQ ID NO 56
<211> LENGTH: 20
<212> TYPE: DNA
<213> ORGANISM: Artificial Sequence
<220> FEATURE:
<223> OTHER INFORMATION: primer

<400> SEQUENCE: 56
tgagggtcat gccgtgtttc                                          20
```